United States Patent
Maddocks

(10) Patent No.: US 12,220,402 B2
(45) Date of Patent: Feb. 11, 2025

(54) FORMULATIONS FOR PERSONALIZED METHODS OF TREATMENT

(71) Applicant: Faeth Therapeutics, Inc., Austin, TX (US)

(72) Inventor: Oliver D. K. Maddocks, Glasgow (GB)

(73) Assignee: Faeth Therapeutics, Inc., Austin, TX (US)

(*) Notice: Subject to any disclaimer, the term of this patent is extended or adjusted under 35 U.S.C. 154(b) by 569 days.

(21) Appl. No.: 17/337,077

(22) Filed: Jun. 2, 2021

(65) Prior Publication Data
US 2022/0117943 A1    Apr. 21, 2022

Related U.S. Application Data

(60) Provisional application No. 63/034,137, filed on Jun. 3, 2020.

(51) Int. Cl.
| | |
|---|---|
| *A61K 31/4172* | (2006.01) |
| *A23L 33/175* | (2016.01) |
| *A61K 31/198* | (2006.01) |
| *A61K 45/06* | (2006.01) |

(52) U.S. Cl.
CPC ........ *A61K 31/4172* (2013.01); *A23L 33/175* (2016.08); *A61K 31/198* (2013.01); *A61K 45/06* (2013.01)

(58) Field of Classification Search
CPC .. A61K 31/4172; A61K 31/198; A61K 45/06; A23L 33/175
See application file for complete search history.

(56) References Cited

U.S. PATENT DOCUMENTS

| | | | |
|---|---|---|---|
| 3,832,465 A | * | 8/1974 | Ghadimi ............... A61K 38/04 |
| | | | 514/21.91 |
| 4,734,401 A | | 3/1988 | Blouin |
| 4,988,724 A | | 1/1991 | Ajani et al. |

(Continued)

FOREIGN PATENT DOCUMENTS

| | | |
|---|---|---|
| EP | 4190173 A1 | 6/2023 |
| JP | 2005289938 A | 10/2005 |

(Continued)

OTHER PUBLICATIONS

International Search Report and Written Opinion issued in PCT/US2021/035476 on Oct. 12, 2021.

(Continued)

*Primary Examiner* — Andrew D Kosar
*Assistant Examiner* — John D McAnany
(74) *Attorney, Agent, or Firm* — Cooley LLP

(57) ABSTRACT

Disclosed herein are formulations and methods of administering formulations to starve cells of nutrients, such as amino acids. The formulations can be substantially devoid of one or more non-essential amino acids. A formulation disclosed herein can be given to a subject to treat a disease, for example, cancer. Removing a particular amino acid or a combination of amino acids from the diet of a subject can lead to improved treatment of various diseases, including cancer. Reduction of amino acid levels in a subject reduces the production of proteins, metabolites, lipids, or nucleic acid that can promote cancer growth and metastasis.

15 Claims, 13 Drawing Sheets

(56) References Cited

U.S. PATENT DOCUMENTS

| | | | |
|---|---|---|---|
| 6,218,420 B1 * | 4/2001 | Dioguardi | A61P 43/00 514/567 |
| 6,713,501 B1 | 3/2004 | Walser | |
| 10,973,251 B1 | 4/2021 | Li et al. | |
| 11,241,407 B2 | 2/2022 | Li et al. | |
| 12,042,477 B2 | 7/2024 | Maddocks et al. | |
| 2003/0129262 A1 | 7/2003 | Epner et al. | |
| 2006/0280840 A1 | 12/2006 | Robertson | |
| 2007/0270355 A1 | 11/2007 | Garcia et al. | |
| 2007/0286909 A1 | 12/2007 | Smith et al. | |
| 2008/0317886 A1 | 12/2008 | Sparkman | |
| 2011/0118528 A1 | 5/2011 | Longo et al. | |
| 2011/0153221 A1 | 6/2011 | Stefanon et al. | |
| 2013/0123363 A1 | 5/2013 | Uesugi et al. | |
| 2014/0087970 A1 | 3/2014 | Possemato et al. | |
| 2014/0100357 A1 | 4/2014 | Miao et al. | |
| 2014/0170259 A1 | 6/2014 | Poels et al. | |
| 2014/0363417 A1 | 12/2014 | Cheng et al. | |
| 2015/0315561 A1 | 11/2015 | Schabbauer et al. | |
| 2017/0143025 A1 | 5/2017 | Rason et al. | |
| 2020/0230092 A1 | 7/2020 | Maddocks et al. | |
| 2022/0054444 A1 | 2/2022 | Maddocks | |
| 2022/0193447 A1 | 6/2022 | Maddocks et al. | |
| 2022/0400730 A1 | 12/2022 | Li et al. | |
| 2023/0277492 A1 | 9/2023 | Maddocks et al. | |

FOREIGN PATENT DOCUMENTS

| | | | |
|---|---|---|---|
| JP | 2014512803 A | 5/2014 | |
| WO | WO-9802441 A2 | 1/1998 | |
| WO | WO-0114387 A1 | 3/2001 | |
| WO | WO-2006043090 A1 | 4/2006 | |
| WO | WO-2009077766 A1 | 6/2009 | |
| WO | WO-2010075007 A3 | 11/2010 | |
| WO | WO-2011092469 A1 | 8/2011 | |
| WO | WO-2011143579 A2 | 11/2011 | |
| WO | WO-2012116229 A2 | 8/2012 | |
| WO | WO-2014049566 A2 | 4/2014 | |
| WO | WO-2015075483 A1 | 5/2015 | |
| WO | WO-2016130918 A1 | 8/2016 | |
| WO | WO-2017053328 A1 | 3/2017 | |
| WO | WO-2017144877 A1 * | 8/2017 | A61K 31/198 |
| WO | WO-2018071873 A2 | 4/2018 | |
| WO | WO-2019092455 A1 | 5/2019 | |
| WO | WO-2019118549 A1 | 6/2019 | |
| WO | WO-2019211605 A1 * | 11/2019 | A23L 33/175 |
| WO | WO-2021016132 A1 | 1/2021 | |
| WO | WO-2021247724 A1 | 12/2021 | |
| WO | WO-2021247923 A1 | 12/2021 | |
| WO | WO-2022015951 A2 | 1/2022 | |
| WO | WO-2022132981 A1 | 6/2022 | |
| WO | WO-2023130140 A2 | 7/2023 | |

OTHER PUBLICATIONS

Adams et al., "The c-myc oncogene driven by immunoglobulin enhancers induces lymphoid malignancy in transgenic mice" Nature (1985) 318:533-538.
Amelio et al., "Serine and glycine metabolism in cancer" Trends Biochem Sci. Apr. 2014; 39(4):191-198.
Anonymous. ClinicalTrials.gov Archive. NCT02337894 on Jan. 13, 2015.Retrived from the Internet: https://clinicaltrails.gov/archive/NCT. Retrieved on Apr. 2, 2017. 5 pages.
Badgley et al., "Absract A41: Leveraging metabolic dependencies in cancer: Cystein addiction in pancreatic cancer cells" Mol Cancer Research (2016) 14(1_Supp): A41, 4 pages.
Barker et al., "Crypt stem cells as the cells-of-origin of intestinal cancer" Nature (2009) 457:608-611.
Bartlett, David L., et al., "Effect of growth hormone and protein intake on tumor growth and host cachexia", Surgery, 1995, vol. 117, No. 3, pp. 260-267.
Bassiri et al., "Translational development of difluoromethylornithine (DFMO) for the treatment of neuroblastoma" Transl Pediatr. Jul. 2015; 4(3):226-238.
Bertino et al., "Targeting tumors that lack methylthioadenosine phosphorylase (MTAP) activity: current strategies" Cancer Biol Ther. Apr. 1, 2011; 11(7):627-632.
Blau et al., eds., "Laboratory Guide to the Methods in Biochemical Genetics" (2008) Berlin Heidelberg, Germany: Springer Verlag. p. 74. 59 pages.
Bunz F et al., "Requirement for p53 and p21 to sustain G2 arrest after DNA damage" Science. Nov. 1998: 282:1497-1501.
CAS Registry No. 1036730-42-3, STN entry date: Jul. 28, 2008, Pidilizumab, 1 page.
CAS Registry No. 1374853-91-4, STN entry date: May 31, 2012, Pembrolizumab, 1 page.
CAS Registry No. 1380723-44-3, STN entry date: Jul. 3, 2012, Atezolizumab, 1 page.
CAS Registry No. 1428935-60-7, STN entry date: Apr. 23, 2013, Durvalumab, 1 page.
CAS Registry No. 1537032-82-8, STN entry date: Feb. 4, 2014, Avelumab, 1 page.
CAS Registry No. 1801342-60-8, STN entry date: Aug. 4, 2015, Cemiplimab, 1 page.
CAS Registry No. 477202-00-9, dated Dec. 19, 2002, 1 page.
CAS Registry No. 70052-12-9, STN entry date: Nov. 16, 1984, Eflornithine, 2 pages.
CAS Registry No. 946414-94-4, STN entry date: Sep. 7, 2007, Nivolumab, 1 page.
CAS Registry No. 96020-91-6, STN entry date: Apr. 21, 1985, Ornithine, 1 page.
Commisso et al., "Macropinocytosis of protein is an amino acid supply route in Ras-transformed cells" Nature (2013) 497:633-637.
Corsetti et al., "Protect and Counter-attack: Nutritional Supplementation with Essential Amino acid Ratios Reduces Doxorubicin-induced Cardiotoxicity in vivo and promote Cancer Cell Death in vitro" J. Cytol. Histol. (2015) 6:5, 1000354, 2 pages.
Donehower, et al. "Mice deficient for p53 are developmentally normal but susceptible to spontaneous tumours", Nature, Mar. 19, 1992, pp. 215-221, vol. 356.
Dredge, K et al., "The polyamine analog PG11047 potentiates the antitumor activity of cisplatin and bevacizumab in preclinical models of lung and prostate cancer" Cancer Chemother Pharmacol. 65, 191-195 (2009).
Erdman et al., "Dietary Reference Intakes For Water, Potassium, Sodium, Chloride, and Sulfate" Institute of Medicine, Feb. 11, 2004, 4 pages.
Extended European Search Report mailed on Sep. 18, 2023, for EP Application No. 23166882.3, 11 pages.
Faubert et al., "Stable isotope tracing to assess tumor metabolism in vivo" Nat Protoc. (2021) Nov. 16(11):5123-5145.
Fiatarone et al., "Exercise training and nutritional supplementation for physical frailty in very elderly people" N. Engl. J. Med. Jun. 23, 1994; 330(25):1769-75.
Fiatarone Singh et al., "The effect of oral nutritional supplements on habitual dietary quality and quantity in frail elders" J. Nutr. Health Aging (2000) 4(1):5-12.
Final Office Action mailed on Aug. 10, 2023, for U.S. Appl. No. 17/338,283, filed Jun. 3, 2021, 14 pages.
Final Office Action mailed on Nov. 24, 2023, for U.S. Appl. No. 18/174,706, filed Feb. 27, 2023, 13 pages.
Final Office Action mailed on Sep. 2, 2022, for U.S. Appl. No. 15/999,666, filed Aug. 20, 2018, 13 pages.
Final Office Action mailed on Sep. 22, 2021, for U.S. Appl. No. 15/999,666, filed Aug. 20, 2018, 11 pages.
Finkelstein et al., "Methionine metabolism in mammals. The methionine-sparing effect of cystine" J Biol Chem. 263(24):11750-11754 (1998).
Geck et al., "Nonessential amino acid metabolism in breast cancer" Advances in Biological Regulation (2016) 62:11-17.
Gravel et al., "Serine deprivation enhances antineoplastic activity of biguanides" Cancer Res. Dec. 15, 2014; 74(24):7521-7533.
Harenza et al., "Transcriptomic profiling of 39 commonly-used neuroblastoma cell lines" Sci Data. Mar. 28, 2017: 4:170033. 8 pages.

(56) References Cited

OTHER PUBLICATIONS

Hingorani et al., "Trp53R172H and KrasG12D cooperate to promote chromosomal instability and widely metastatic pancreatic ductal adenocarcinoma in mice" Cancer Cell (2005) 7:469-483.
Hirakawa et al., "Comparative utilization of a crystalline amino acid diet and a methionine-fortified casein diet by young rats and mice" Nutr Res (1984) 4(5):891-895.
Hogarty et al., "ODC1 is a critical determinant of MYCN oncogenesis and a therapeutic target in neuroblastoma" Cancer Res. Dec. 1, 2008; 68(23):9735-9745.
Holbert et al., "Polyamines in cancer: integrating organismal metabolism and antitumour immunity" Nat Rev Cancer.Aug. 2022; 22(8):467-480.
Hui et al., "Glucose feeds the TCA cycle via circulating lactate" Nature. Nov. 2, 2017; 551(7678):115-118.
Hui et al., "Quantitative Fluxomics of Circulating Metabolites" Cell Metab. Oct. 6, 2020; 32(4):676-688. e4.
Institute of Medicine, "Dietary Reference Intakes for Energy, Carbohydrate, Fiber, Fat, Fatty Acids, Cholesterol, Protein and Amino Acids" Chapters 6, 7, and 8, Sep. 2002, 323 pages.
International Search Report and Written Opinion issued in PCT/2021/35780 on Oct. 1, 2021. 11 pages.
International Search Report and Written Opinion mailed on Apr. 11, 2022, for PCT/US2021/063639, filed on Dec. 15, 2021, 8 pages.
International Search Report and Written Opinion mailed on Jun. 26, 2023, for PCT/US2023/60025, filed on Jan. 3, 2023, 9 pages.
International Search Report and Written Opinion, PCT/GB2017/050458, mailed Jul. 18, 2017,20 pages.
Kocak et al., "Hox-C9 activates the intrinsic pathway of apoptosis and is associated with spontaneous regression in neuroblastoma" Cell Death Dis. Apr. 11, 2013; 4(4):e586. 11 pages.
Kshattry S. et al. "Abstract 367: Assessing the therapeutic efficacy of Cyst(e)inase to induce oxidative stress mediated cytotoxicity in pancreatic cancer cells" Experimental and Molecular Therapeutics, 4 pages, 2016.
Labadie et al., "Reimagining IDO Pathway Inhibition in Cancer Immunotherapy via Downstream Focus on the Tryptophan-Kynurenine-Aryl Hydrocarbon Axis" Clin Cancer Res. Mar. 1, 2019; 25(5):1462-1471.
Labuschagne CF et al., "Serine, but not glycine, supports one-carbon metabolism and proliferation of cancer cells" Cell Reports 7. 1248-1258, May 22, 2014.
Lancha et al., "Effect of aspartate, asparagine, and carnitine supplementation in the diet on metabolism of skeletal muscle during a moderate exercise" Physiol Behav. Feb. 1995; 57(2):367-71.
Lewis et al., "A subset analysis of a phase II trial evaluating the use of DFMO as maintenance therapy for high-risk neuroblastoma" Int J Cancer. Dec. 1, 2020; 147(11):3152-3159.
Liberzon et al., "Molecular signatures database (MSigDB) 3.0" Bioinformatics. Jun. 15, 2011; 27(12):1739-1740.
Locasale, "Serine, glycine and one-carbon units: cancer metabolism in full circle" Nat Rev Cancer. Aug. 2013; 13(8):572-583.
Logiudice et al., "Alpha-Difluoromethylornithine, an Irreversible Inhibitor of Polyamine Biosynthesis, as a Therapeutic Strategy against Hyperproliferative and Infectious Diseases" Med Sci (Basel). Feb. 8, 2018; 6(1):12. 17 pages.
Lopez-Lazaro M,Selective amino acid restriction therapy(SAART);a non-pharmacological strategy against all types of cancer cells. Oncoscience 2015;2(10):857-866.
Maddocks et al., "Serine metabolism supports the methionine cycle and DNR/RNA methylation through de novo ATP synthesis in cancer cells" Molecular Cell. (2016) 61:210-221.
Maddocks et al., "Serine starvation induces stress and p53-dependent metabolic remodelling in cancer cells" Nature, Dec. 2013; 493(7433): 542-546.
McCormack et al. "Oral nutritional supplement fortified with beta-alanine improves physical working capacity in older adults: a randomized, placebo-controlled study." Experimental gerontology 48(9) 2013:933-939.

Miyo, M. et al., "Metabolic Adaptation to Nutritional Stress in Human Colorectal Cancer" Scientific Reports (2016) vol. 6, No. 1, 38415, 13 pages.
Morton et al., "Mutant p53 drives metastasis and overcomes growth arrest/senescence in pancreatic cancer" PNAS USA (2010) 107:246-251.
Moser et al., "A dominant mutation that predisposes to multiple intestinal neoplasia in the mouse" Science (1990) 322-324.
NAS. IOM. Food and Nutrition Board, "Dietary Reference Intakes: RDA and AI for Vitamins and Elements" (2017) 3 pages.
Non-Final Office Action mailed on Jan. 5, 2023, for U.S. Appl. No. 17/338,283, filed Jun. 3, 2021, 14 pages.
Non-Final Office Action mailed on Jul. 7, 2023, for U.S. Appl. No. 18/174,706, filed Feb. 27, 2023, 13 pages.
Non-Final Office Action mailed on Mar. 18, 2021, for U.S. Appl. No. 15/999,666, filed Aug. 20, 2018, 8 pages.
Non-Final Office Action mailed on May 10, 2023, for U.S. Appl. No. 15/999,666, filed Aug. 20, 2018, 12 pages.
Notice of Allowance mailed on Jan. 4, 2024, for U.S. Appl. No. 15/999,666, filed Aug. 20, 2018, 12 pages.
Okada, Kenzo, et al., "Tumor glutamine level is negatively correlated with tumor weight in tumor-bearing rats administered a glutamine antagonist and a new imbalanced amino acid solution", Journal of Clinical Biochemistry and Nutrition, 1992, vol. 12, No. 3, pp. 183-191.
Paddon-Jones et al., "Amino acid ingestion improves muscle protein synthesis in the young and elderly" Am J Physiol Endocrinol Metab. Mar. 2004; 286(3):E321-E328.
Paddon-Jones et al., "Differential stimulation of muscle protein synthesis in elderly humans following isocaloric ingestion of amino acids or whey protein" Experimental Gerontology. Feb. 1, 2006; 41(2):215-219.
Partial European Search Report mailed on Sep. 20, 2023, for EP Application No. EP 23151551.1, 23 pages.
PCT/US2021/035780 International Preliminary Report on Patentability (Chapter I) dated Dec. 6, 2022. 9 Pages.
Polet et al., "Reducing the serine availability complements the inhibition of the glutamine metabolism to block leukemia cell growth" Oncotarget, Jan. 2016; 7(2):1765-1776.
Possemato et al., "Functional genomics reveal that the serine synthesis pathway is essential in breast cancer" Nature Aug. 18, 2011; 476(7360):346-350.
Ran et al., "Genome engineering using the CRISPR-Cas9 system" Nat Protoc. Nov. 2013; 8(11):2281-2308.
Rose WC et al., "Growth on diets devoid of glycine, serine, and cystine, and low in choline" J Biol Chem. (1952) 194:321-328.
Rounbehler et al., "Targeting ornithine decarboxylase impairs development of MYCN-amplified neuroblastoma" Cancer Res. Jan. 15, 2009; 69(2):547-553.
Sahu et al., "Proline Starvation Induces Unresolved ER Stress and Hinders mTORC1-Dependent Tumorigenesis" Cell Metabolism (2016) 24:753-761.
Search Report, Intellectual Property Office, United Kingdom Application No. GB1609441.9, Mar. 1, 2017,5 pages.
Sholler et al., "A Phase I Trial of DFMO Targeting Polyamine Addiction in Patients with Relapsed/Refractory Neuroblastoma" PLoS One. May 27, 2015;10(5):e0127246. 20 pages.
Sholler et al., "Maintenance DFMO Increases Survival in High Risk Neuroblastoma" Sci Rep. Sep. 27, 2018; 8(1):14445. 9 pages.
Snezhkina, A.V. et al., "The Dysregulation of Polyamine Metabolism in Colorectal Cancer Is Associated with Overexpression of c-Myc and C/EBPβ rather than Enterotoxigenic Bacteroides fragilis Infection" Oxid Med Cell Longev. (2016) Article ID 2353560, 11 pages.
Soldin et al., "Pediatric reference ranges" 3rd ed., Washington: AACC Press, (1999) pp. 11-20.
Solerte et al., "Metabolic effects of orally administered amino acid mixture in elderly subjects with poorly controlled type 2 diabetes mellitus" Am J Cardiol. Apr. 22, 2004; 93(8A):23A-29A.
Su et al., "Metabolite Spectral Accuracy on Orbitraps" Anal Chem. Jun. 6, 2017; 89(11):5940-5948.
Su et al., "Multiple intestinal neoplasia caused by a mutation in the murine homolog of the APC gene" Science (1992) 256:668-670.

(56) References Cited

OTHER PUBLICATIONS

Tang et al., "Cystine Deprivation Triggers Programmed Necrosis in VHL-Deficient Renal Cell Carcinomas" Cancer Res. Apr. 1, 2016; 76(7):1892-1903.
Trumbo et al., "Dietary reference intakes for energy, carbohydrate, fiber, fat, fatty acids, cholesterol, protein and amino acids" J Am Diet Assoc. Nov. 2002; 102(11):1621-1630.
Uniprot P01137, Sep. 13, 2023, 14 pages.
Uniprot P14784, Sep. 13, 2023, 7 pages.
Uniprot P16410, Sep. 13, 2023, 11 pages.
Uniprot P25942, Sep. 13, 2023, 8 pages.
Uniprot P43489, Sep. 13, 2023, 6 pages.
Uniprot Q07011, Sep. 13, 2023, 6 pages.
Uniprot Q15116, Sep. 13, 2023, 9 pages.
Uniprot Q495A1, Sep. 13, 2023, 5 pages.
Uniprot Q5ZPR3, Sep. 13, 2023, 9 pages.
Uniprot Q8TDQ0, Sep. 13, 2023, 9 pages.
Uniprot Q9H7M9, Sep. 13, 2023, 7 pages.
Uniprot Q9NZQ7, Sep. 13, 2023, 9 pages.
Uniprot Q9Y6W8, Sep. 13, 2023, 4 pages.
Vigneron AM et al. Cytoplasmic ASPP1 inhibits apoptosis through the control of YAP. Genes & Development.2010;24:2430-2439.
Walpole et al., "The weight of nations: an estimation of adult human biomass" BMC Public Health. Jun. 18, 2012; 12:439. 6 pages.
Wang et al., "Peak Annotation and Verification Engine for Untargeted LC-MS Metabolomics" Anal Chem. Feb. 5, 2019; 91(3):1838-1846.
Weiss et al. "Targeted Expression of MYCN Causes Neuroblastoma in Transgenic Mice", The EMBO Journal (1997), 16(11): 2985-2995.
Wernerman, J., "Clinical use of glutamine supplementation" J Nutr. Oct. 2008; 138(10):2040S-2044S.
Wu et al., "Dietary protein intake and human health" Food Funct. Mar. 2016; 7(3):1251-1265.
Ying et al., "Oncogenic Kras maintains pancreatic tumors through regulation of anabolic glucose metabolism" Cell (2012) 149:656-670.
Zhang et al., "Application of Holistic Liquid Chromatography-High Resolution Mass Spectrometry Based Urinary Metabolomics for Prostate Cancer Detection and Biomarker Discovery" PLoS One (2013) 8(6):e65880, 10 pages.
Zhang et al., "Polyamine pathway activity promotes cysteine essentiality in cancer cells" Nature Metabolism (2020) 2:1062-1076, 27 pages.
Zhang W. et al., "Stromal control of cystine metabolism promotes cancer cell survival in chronic lymphocytic leukaemia" Nature Cell Biology, 14(3):276-286 2012.
Extended European Search Report mailed on Feb. 1, 2024, for EP Application No. 23151551.1, 27 pages.
Fu et al., "Specific amino acid dependency regulates invasiveness and viability of androgen-independent prostate cancer cells" Nutr Cancer. (2003) 45(1):60-73.
Ge et al., "Activation of caspases and cleavage of Bid are required for tyrosine and phenylalanine deficiency-induced apoptosis of human A375 melanoma cells" Arch Biochem Biophys. Jul. 1, 2002; 403(1):50-58.
Yan et al., "Effects of complex unbalanced amino acids on tumors in mice bearing liver cancer H22" Chinese Journal of Clinical Oncology (2011) 38(3):134-137.
Bonfili et al., "Essential amino acid mixtures drive cancer cells to apoptosis through proteasome inhibition and autophagy activation" FEBS J. Jun. 2017; 284(11):1726-1737.
Extended European Search Report mailed on Jun. 12, 2024, for EP Application No. 21818131.1,10 pages.
Extended European Search Report mailed on Jun. 3, 2024, for EP Application No. 21816784.9, 10 pages.
Hamad et al., "Amino Acids Diets as Model for Investigating Cancer Induced by Acrylamide Produced during Wrong Food Cooking" SOJ Biochem (2018) 4(1): 1-14.
Tajan et al., "Dietary Approaches to Cancer Therapy" Cancer Cell. Jun. 8, 2020; 37(6):767-785.
Butler et al., "Amino Acid Depletion Therapies: Starving Cancer Cells to Death," Trends in Endocrinology and Metabolism Jun. 2021; 32(6):367-381.
Casero Jr. et al., "Polyamine metabolism and cancer: treatments, challenges and opportunities," Nature Reviews Cancer. Nov. 2018; 18(11):681-695.
Cavuoto et al., "A review of methionine dependency and the role of methionine restriction in cancer growth control and life-span extension" Cancer Treatment Reviews Oct. 2012; 38(6):726-736.
Doxsee et al., "Sulfasalazine-Induced Cystine Starvation: Potential Use for Prostate Cancer Therapy" Prostate Feb. 1, 2007; 67(2):162-171.
Non-Final Office Action mailed on Feb. 23, 2024, for U.S. Appl. No. 17/338,283, filed Jun. 3, 2021, 13 pages.
Notice of Allowance mailed on Apr. 12, 2024, for U.S. Appl. No. 15/999,666, filed Aug. 20, 2018, 11 pages.
Notice of Allowance mailed on May 9, 2024, for U.S. Appl. No. 15/999,666, filed Aug. 20, 2018, 9 pages.
Tajan et al., "Serine synthesis pathway inhibition cooperates with dietary serine and glycine limitation for cancer therapy" Nat Commun. Jan. 14, 2021; 12(1):366. 16 pages.
Yan et al., "Effects of complex unbalanced amino acids on tumors in mice bearing liver cancer H22" Chinese Journal of Clinical Oncology (2011) 38(3):134-137 (with full English Translation). 8 total pages.
Non-Final Office Action for U.S. Appl. No. 18/174,706 mailed Jul. 18, 2024, 20 pages.
Notice of Allowance for U.S. Appl. No. 17/338,283 mailed Aug. 13, 2024, 6 pages.
Notice of Allowance for U.S. Appl. No. 17/338,283 mailed Jul. 17, 2024, 9 pages.

\* cited by examiner

PANEL C

FORMULATIONS FOR PERSONALIZED METHODS OF TREATMENT

CROSS-REFERENCE

This application claims the benefit of U.S. Provisional Application No. 63/034,137, filed Jun. 3, 2020, which is incorporated by reference herein in its entirety.

BACKGROUND

Current therapies for the treatment for cancer or other pathologies can be ineffective due to patient-specific factors. Thus, personalized methods and formulations can be developed for therapy of various diseases, including cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, disclosed herein is a composition comprising in a unit dosage form: a) a non-essential amino acid or a salt thereof, wherein the non-essential amino acid or the salt thereof is not part of a polypeptide; b) a first essential amino acid or a first salt thereof and a second essential amino acid or a second salt thereof, wherein the first essential amino acid or the first salt thereof and the second essential amino acid or the second salt thereof are present in the composition in an equal amount, wherein the first essential amino acid and the first salt thereof and the second essential amino acid and the second salt thereof are not part of a polypeptide; and c) a pharmaceutically acceptable excipient. In some embodiments, disclosed herein is a composition comprising in a powder form: a) an essential amino acid, wherein the essential amino acid is not part of polypeptide; b) a non-essential amino acid, wherein the non-essential amino acid is not part of a polypeptide; and c) a pharmaceutically acceptable excipient, wherein the composition does not comprise serine or glycine, wherein if, in a study of a tumor volume change in a subject, then the tumor volume in a subject administered the composition is reduced by at least about 20% as compared to a subject that is not administered the composition.

In some embodiments, disclosed herein is a composition comprising in a unit dosage form: a) a non-essential amino acid or a salt thereof, wherein the non-essential amino acid or the salt thereof is not part of a polypeptide, b) a first essential amino acid or a first salt thereof and a second essential amino acid or a second salt thereof, wherein the first essential amino acid or the first salt thereof and the second essential amino acid or the second salt thereof are present in the composition in an equal amount, wherein the first essential amino acid and the first salt thereof and the second essential amino acid and the second salt thereof are not part of a polypeptide; and c) a pharmaceutically acceptable excipient, wherein if, in a study of a tumor volume change in a subject, then the tumor volume in a subject administered the composition is reduced by at least about 20% as compared to a subject administered a placebo.

In some embodiments, disclosed herein is a composition comprising in a powder form: a) an essential amino acid, wherein the essential amino acid is not part of polypeptide; b) a non-essential amino acid, wherein the non-essential is not part of a polypeptide; and c) a pharmaceutically acceptable excipient, wherein the composition does not comprise serine or glycine, and wherein if, in a study of a tumor volume change in a subject, then the tumor volume in a subject administered the composition is reduced by at least about 20% as compared to a subject administered a placebo. In some embodiments, disclosed herein is a method of reducing a tumor volume in a subject, the method comprising administering to the subject a therapeutically-effective amount of a composition, wherein the composition is devoid of at least one non-essential amino acid for at least one month.

In some embodiments, disclosed herein is a method of treating a cancer in a subject in need thereof, wherein the subject is on a modified diet, wherein the modified diet provides at most about 50% of a daily caloric content from carbohydrates, the method comprising administering to the subject a therapeutically-effective amount of a dietary product, wherein the dietary product is devoid of at least one non-essential amino acid. In some embodiments, disclosed herein is method of reducing an average serum amino acid level of at least one non-essential amino acid in a subject in need thereof, the method comprising: a) administering to the subject a therapeutically-effective amount of a dietary product that is devoid of the at least one non-essential amino acid for a first period of time; wherein the subject is on a modified diet that provides from at least about 1% to at most about 40% of a daily caloric content from carbohydrates during the first period of time; and b) not administering the dietary product to the subject for a second period of time, wherein the subject is on a normal diet that provides at least about 45% of a daily caloric content from carbohydrates during the second period of time.

DETAILED DESCRIPTION

Figure 1:
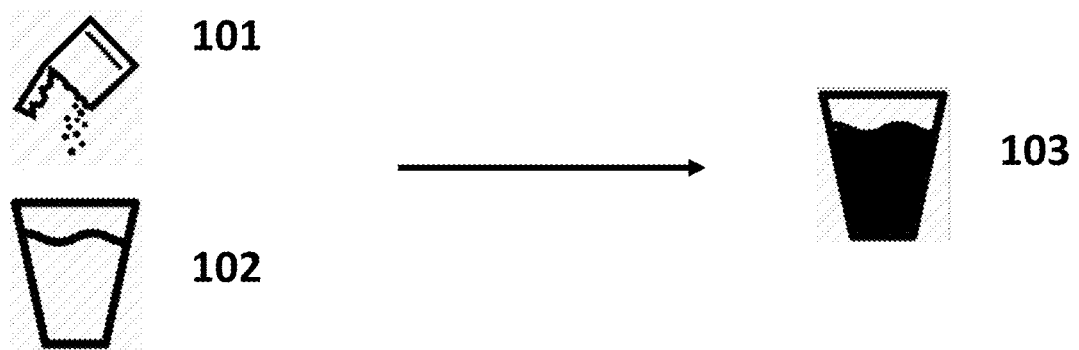
FIG. 1 illustrates adding a sachet containing a composition disclosed herein into a glass of water, and a subject drinking the mixture of the composition.
Figure 1:
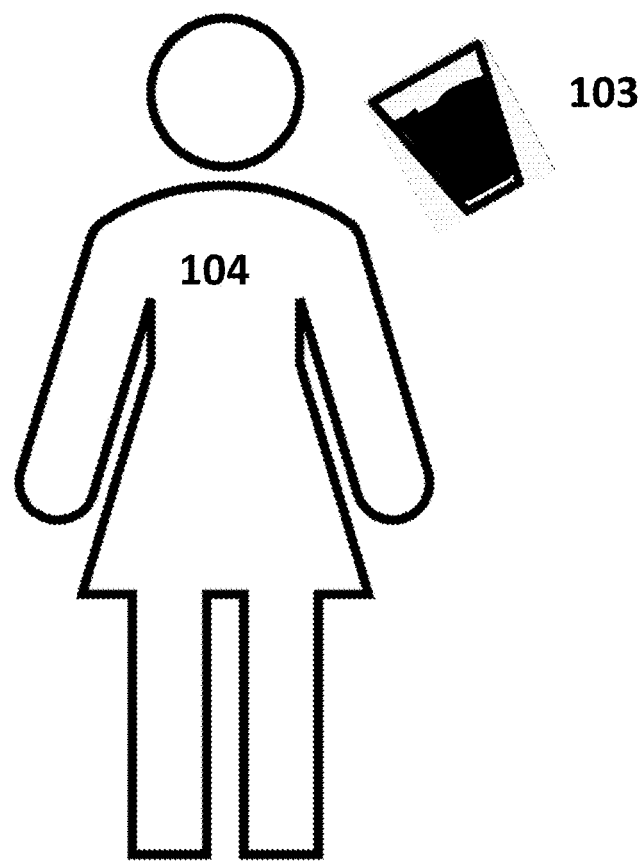

Described herein are compositions and dietary products comprising essential and non-essential amino acids. A composition disclosed herein can be given to a subject to treat a disease, for example, cancer. As shown in FIG. 1, a composition disclosed herein can be provided as a powder in a sachet (101). The powder from the sachet can be added to, for example, water (102) to create a liquid beverage for consumption by the subject. The subject (104) drinks the mixture of the composition prepared in water (103).

Removing a particular amino acid or a combination of amino acids from the diet of a subject can lead to improved treatment of various diseases, including cancer. Reduction of amino acid levels in a subject reduces the production of proteins, metabolites, lipids, or nucleic acid that can promote cancer growth and metastasis.

In some embodiments, a composition disclosed herein is a pharmaceutical composition. In some embodiments, a composition disclosed herein is a medical food. In some embodiments, a composition disclosed herein is a food supplement. In some embodiments, a composition disclosed herein is a nutritional supplement. In some embodiments, a composition disclosed herein is a nutrient supplement. In some embodiments, a composition disclosed herein is a dietary product. In some embodiments, a composition disclosed herein is a drug.

In some embodiments, a composition disclosed herein can be used with at least one therapeutic agent, such as a drug, antibody, or enzyme. In some embodiments, a composition disclosed herein can make a therapeutic agent more effective in treating a condition.

In some embodiments, a composition disclosed herein is a food which is formulated to be consumed or administered enterally under the supervision of a physician and which is intended for the specific dietary management of a disease or condition for which distinctive nutritional requirements, based on recognized scientific principles, are established by medical evaluation.

Amino Acids

A composition of the disclosure comprises at least ten amino acids or salts thereof. In some embodiments, a composition of the disclosure comprises 10, 11, 12, 13, 14, 15, 16, 17, 18, or 19 amino acids or a salt of any amino acid thereof. In some embodiments, a composition of the disclosure comprises 10 amino acids or a salt of any amino acid thereof. In some embodiments, a composition of the disclosure comprises 14 amino acids or a salt of any amino acid thereof. In some embodiments, a composition of the disclosure comprises 18 amino acids or a salt of any amino acid thereof. A salt of an amino acid disclosed herein can be a pharmaceutically acceptable salt.

In some embodiments, a composition of the disclosure comprises 1, 2, 3, 4, 5, 6, 7, 8, or 9 essential amino acids or a salt of any amino acid thereof. In some embodiments, a composition of the disclosure comprises 7, 8, or 9 essential amino acids or a salt of any amino acid thereof. In some embodiments, a composition of the disclosure comprises 8 essential amino acids or a salt of any amino acid thereof. In some embodiments, a composition of the disclosure comprises 9 essential amino acids or a salt of any amino acid thereof. A salt of an amino acid disclosed herein can be a pharmaceutically acceptable salt.

In some embodiments, a composition of the disclosure comprises 1, 2, 3, 4, 5, 6, 7, 8, 9, 10, or 11 non-essential amino acids or a salt of any amino acid thereof. In some embodiments, a composition of the disclosure comprises 7, 8, 9, 10, or 11 non-essential amino acids or a salt of any amino acid thereof. In some embodiments, a composition of the disclosure comprises 7 non-essential amino acids or a salt of any amino acid thereof. In some embodiments, a composition of the disclosure comprises 8 non-essential amino acids or a salt of any amino acid thereof. In some embodiments, a composition of the disclosure comprises 9 non-essential amino acids or a salt of any amino acid thereof. A salt of an amino acid disclosed herein can be a pharmaceutically acceptable salt.

A composition of the disclosure can comprise essential amino acids or salts thereof and non-essential amino acids or a salt of any amino acid thereof. In some embodiments, a composition of the disclosure comprises 1, 2, 3, 4, 5, 6, 7, 8, or 9 essential amino acids or a salt of any amino acid thereof and 1, 2, 3, 4, 5, 6, 7, 8, 9, 10, or 11 non-essential amino acids or a salt of any amino acid thereof. In some embodiments, a composition of the disclosure comprises 7, 8, or 9 essential amino acids or a salt of any amino acid thereof and 6, 7, 8, or 9 non-essential amino acids or a salt of any amino acid thereof. In some embodiments, a composition of the disclosure comprises 8 or 9 essential amino acids or a salt of any amino acid thereof and 8 or 9 non-essential amino acids or a salt of any amino acid thereof. In some embodiments, a composition of the disclosure comprises 9 essential amino acids or a salt of any amino acid thereof and 7 non-essential amino acids or a salt of any amino acid thereof. In some embodiments, a composition of the disclosure comprises 9 essential amino acids or a salt of any amino acid thereof and 8 non-essential amino acids or a salt of any amino acid thereof. In some embodiments, a composition of the disclosure comprises 9 essential amino acids or a salt of any amino acid thereof and 9 non-essential amino acids or a salt of any amino acid thereof. A salt of an amino acid disclosed herein can be a pharmaceutically acceptable salt.

In some embodiments, a composition of the disclosure comprises histidine, isoleucine, leucine, lysine, methionine, cysteine, phenylalanine, tyrosine, taurine, threonine, tryptophan, valine, arginine, glutamine, alanine, aspartic acid, asparagine, glutamic acid or proline. In some embodiments, a composition of the disclosure comprises L-histidine, L-isoleucine, L-leucine, L-lysine, L-methionine, L-cysteine, L-phenylalanine, L-tyrosine, L-threonine, L-tryptophan, L-valine, L-arginine, L-glutamine, L-alanine, L-aspartic acid, L-asparagine, L-glutamic acid, or L-proline. Any composition of the disclosure can include cysteine in place of cystine, or cystine in place of cysteine.

In some embodiments, a composition comprises histidine or a salt thereof, such as L-histidine or L-histidine hydrochloride. In some embodiments, a composition of the disclosure comprises isoleucine or a salt thereof, such as L-isoleucine, L-isoleucine methyl ester hydrochloride, or L-isoleucine ethyl ester hydrochloride. A salt of an amino acid disclosed herein can be a pharmaceutically acceptable salt. In some embodiments, a composition of the disclosure comprises leucine or a salt thereof, such as L-leucine, L-leucine methyl ester hydrochloride, or L-leucine ethyl ester hydrochloride. A salt of an amino acid disclosed herein can be a pharmaceutically acceptable salt. In some embodiments, a composition of the disclosure comprises lysine or a salt thereof, such as L-lysine, L-lysine hydrochloride, or L-lysine dihydrochloride. A salt of an amino acid disclosed herein can be a pharmaceutically acceptable salt. In some embodiments, a composition of the disclosure comprises methionine or a salt thereof, such as L-methionine, L-methionine methyl ester hydrochloride, or L-methionine hydrochloride. A salt of an amino acid disclosed herein can be a pharmaceutically acceptable salt.

In some embodiments, a composition of the disclosure comprises cysteine or a salt thereof, such as L-cysteine, L-cysteine hydrochloride, L-cysteine methyl ester hydrochloride, or L-cysteine ethyl ester hydrochloride. Any composition of the disclosure can include cysteine in place of cystine, or cystine in place of cysteine. In some embodiments, a composition discloses cystine or a salt thereof, such as L-cystine. A salt of an amino acid disclosed herein can be a pharmaceutically acceptable salt. In some embodiments, a composition of the disclosure comprises phenylalanine or a salt thereof, such as L-phenylalanine, DL-phenylalanine, or L-phenylalanine methyl ester hydrochloride. In some embodiments, a composition of the disclosure comprises tyrosine or a salt thereof, such as L-tyrosine or L-tyrosine hydrochloride. In some embodiments, a composition of the disclosure comprises threonine or a salt thereof, such as L-threonine or L-threonine methyl ester hydrochloride. In some embodiments, a composition of the disclosure comprises L-tryptophan. In some embodiments, a composition of the disclosure comprises valine or a salt thereof, such as L-valine, L-valine methyl ester hydrochloride, or L-valine ethyl ester hydrochloride. A salt of an amino acid disclosed herein can be a pharmaceutically acceptable salt.

In some embodiments, a composition of the disclosure comprises arginine or a salt thereof, such as L-arginine or L-arginine hydrochloride. In some embodiments, a composition of the disclosure comprises glutamine or a salt thereof, such as L-glutamine or L-glutamine hydrochloride. In some embodiments, a composition of the disclosure comprises alanine or a salt thereof, such as L-alanine or β-alanine. In some embodiments, a composition of the disclosure comprises aspartic acid or a salt thereof, such as L-aspartic acid, D-aspartic acid, L- or D-aspartic acid potassium salt, L- or D-aspartic acid hydrochloride salt; L- or D-aspartic acid magnesium salt, or L- or D-aspartic acid calcium salt. In some embodiments, a composition of the disclosure comprises L-asparagine. In some embodiments, a composition of the disclosure comprises glutamic acid or a salt thereof, such as L-glutamic acid or L-glutamic acid hydrochloride. In some embodiments, a composition of the disclosure comprises proline or a salt thereof, such as L-proline, L-proline hydrochloride, L-proline methyl ester hydrochloride, or L-proline ethyl ester hydrochloride. A salt of an amino acid disclosed herein can be a pharmaceutically acceptable salt.

In some embodiments, a composition of the disclosure does not comprise proline, a hydrate thereof, or a salt thereof. In some embodiments, a composition of the disclosure does not comprise serine, a hydrate thereof, or a salt thereof. In some embodiments, a composition of the disclosure does not comprise glycine, a hydrate thereof, or a salt thereof. In some embodiments, a composition of the disclosure does not comprise cysteine, a hydrate thereof, or a salt thereof. In some embodiments, a composition of the disclosure does not comprise glutamine, a hydrate thereof, or a salt thereof. In some embodiments, a composition of the disclosure does not comprise glutamic acid, a hydrate thereof, or a salt thereof.

In some embodiments, a composition of the disclosure does not comprise (a) serine, a hydrate thereof, or a salt thereof; and (b) glycine, a hydrate thereof, or a salt thereof. In some embodiments, a composition of the disclosure does not comprise (a) serine, a hydrate thereof, or a salt thereof; (b) glycine, a hydrate thereof, or a salt thereof; and (c) proline, a hydrate thereof, or a salt thereof. In some embodiments, a composition of the disclosure does not comprise (a) serine, a hydrate thereof, or a salt thereof; (b) glycine, a hydrate thereof, or a salt thereof; and (c) cysteine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) proline, a hydrate thereof, or a salt thereof; and (d) cysteine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) proline, a hydrate thereof, or a salt thereof; and (d) arginine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) proline, a hydrate thereof, or a salt thereof and (d) tyrosine, a hydrate thereof, or a salt thereof. In some embodiments, a composition of the disclosure does not comprise (a) serine, a hydrate thereof, or a salt thereof; (b) glycine, a hydrate thereof, or a salt thereof (c) cysteine, a hydrate thereof, or a salt thereof; and (d) arginine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) cysteine, a hydrate thereof, or a salt thereof and (d) tyrosine, a hydrate thereof, or a salt thereof.

In some embodiments, a composition of the disclosure does not comprise (a) serine, a hydrate thereof, or a salt thereof; (b) glycine, a hydrate thereof, or a salt thereof (c) proline, a hydrate thereof, or a salt thereof; (d) cysteine, a hydrate thereof, or a salt thereof; and (e) arginine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) proline, a hydrate thereof, or a salt thereof; (d) cysteine, a hydrate thereof, or a salt thereof and (e) tyrosine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) proline, a hydrate thereof, or a salt thereof; (d) cysteine, a hydrate thereof, or a salt thereof (e) tyrosine, a hydrate thereof, or a salt thereof; and (f) arginine, a hydrate thereof, or a salt thereof. In some embodiments, a composition of the disclosure does not comprise (a) serine, a hydrate thereof, or a salt thereof; (b) glycine, a hydrate thereof, or a salt thereof; (c) cysteine, a hydrate thereof, or a salt thereof (d) glutamine, a hydrate thereof, or a salt thereof and (e) glutamic acid, a salt thereof, a hydrate thereof, or a salt thereof. In some embodiments, a composition of the disclosure is further devoid of glutamine, a hydrate thereof, or a salt thereof. In some embodiments, a composition of the disclosure is further devoid of glutamate, a hydrate thereof, or a salt thereof.

In some embodiments, a composition can comprise at least 2, 3, 4, 5, 6, 7, 8, 9, 10, 11, 12, 13, 14, or 15 of: a) histidine or a salt thereof from about 2% to about 6% (w/w); b) isoleucine or a salt thereof from about 2% to about 6% (w/w); c) leucine or a salt thereof from about 6% to about 11% (w/w); d) lysine or a salt thereof from about 5% to about 9% (w/w); e) methionine or a salt thereof from about 2% to about 4% (w/w); f) cysteine or a salt thereof from about 1% to about 3% (w/w); g) phenylalanine or a salt thereof from about 3% to about 6% (w/w); h) tyrosine or a salt thereof from about 1% to about 3% (w/w); i) threonine or a salt thereof from about 3% to about 5% (w/w); j) tryptophan or a salt thereof from about 1% to about 3% (w/w); k) valine or a salt thereof from about 5% to about 9% (w/w); l) arginine or a salt thereof from about 5% to about 9% (w/w); m) glutamine or a salt thereof from about 5% to about 11% (w/w); n) alanine or a salt thereof from about 2% to about 7% (w/w); o) aspartic acid or a salt thereof from about 6% to about 10% (w/w); p) asparagine or a salt thereof from about 3% to about 7% (w/w); q) glutamic acid or a salt thereof from about 8% to about 14% (w/w); or r) proline or a salt thereof from about 6% to about 12% (w/w). In some embodiments, a composition can comprise in a unit dosage form: a) histidine or a salt thereof from about 2% to about 6% (w/w); b) isoleucine or a salt thereof from about 2% to about 6% (w/w); c) leucine or a salt thereof from about 6% to about 11% (w/w); d) lysine or a salt thereof from about 5% to about 9% (w/w); e) methionine or a salt thereof from about 2% to about 4% (w/w); f) cysteine or a salt thereof from about 1% to about 3% (w/w); g) phenylalanine or a salt thereof from about 3% to about 6% (w/w); h) tyrosine or a salt thereof from about 1% to about 3% (w/w); i) threonine or a salt thereof from about 3% to about 5% (w/w); j) tryptophan or a salt thereof from about 1% to about 3% (w/w); k) valine or a salt thereof from about 5% to about 9% (w/w); l) arginine or a salt thereof from about 5% to about 9% (w/w); m) glutamine or a salt thereof from about 5% to about 11% (w/w); n) alanine or a salt thereof from about 2% to about 7% (w/w); o) aspartic acid or a salt thereof from about 6% to about 10% (w/w); p) asparagine or a salt thereof from about 3% to about 7% (w/w); q) glutamic acid or a salt thereof from about 8% to about 14% (w/w); and r) proline or a salt thereof from about 6% to about 12% (w/w). Any composition of the disclosure can include cysteine in place of cystine, or cystine in place of cysteine.

In some embodiments, a composition of the disclosure can comprise at least 1, 2, 3, 4, 5, 6, 7, 8, 9, or 10 of: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); or m) glutamine or a salt thereof from about 7% to about 11% (w/w). In some embodiments, a composition can comprise in a unit dosage form: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); and m) glutamine or a salt thereof from about 7% to about 11% (w/w). Any composition of the disclosure can include cysteine in place of cystine, or cystine in place of cysteine.

In some embodiments, a composition can comprise at least 2, 3, 4, 5, 6, 7, 8, 9, 10, 11, 12, 13, 14, or 15 of: a) histidine or a salt thereof from about 2% to about 5% (w/w); b) isoleucine or a salt thereof from about 2% to about 5% (w/w); c) leucine or a salt thereof from about 6% to about 10% (w/w); d) lysine or a salt thereof from about 5% to about 8% (w/w); e) methionine or a salt thereof from about 2% to about 4% (w/w); f) cysteine or a salt thereof from about 1% to about 3% (w/w); g) phenylalanine or a salt thereof from about 3% to about 5% (w/w); h) tyrosine or a salt thereof from about 1% to about 3% (w/w); i) threonine or a salt thereof from about 3% to about 5% (w/w); j) tryptophan or a salt thereof from about 1% to about 3% (w/w); k) valine or a salt thereof from about 5% to about 9% (w/w); l) arginine or a salt thereof from about 5% to about 9% (w/w); m) glutamine or a salt thereof from about 7% to about 11% (w/w); n) alanine or a salt thereof from about 4% to about 7% (w/w); o) aspartic acid or a salt thereof from about 6% to about 10% (w/w); p) asparagine or a salt thereof from about 3% to about 6% (w/w); q) glutamic acid or a salt thereof from about 8% to about 14% (w/w); and r) proline or a salt thereof from about 6% to about 10% (w/w). In some embodiments, a composition can comprise in a unit dosage form: a) histidine or a salt thereof from about 2% to about 5% (w/w); b) isoleucine or a salt thereof from about 2% to about 5% (w/w); c) leucine or a salt thereof from about 6% to about 10% (w/w); d) lysine or a salt thereof from about 5% to about 8% (w/w); e) methionine or a salt thereof from about 2% to about 4% (w/w); f) cysteine or a salt thereof from about 1% to about 3% (w/w); g) phenylalanine or a salt thereof from about 3% to about 5% (w/w); h) tyrosine or a salt thereof from about 1% to about 3% (w/w); i) threonine or a salt thereof from about 3% to about 5% (w/w); j) tryptophan or a salt thereof from about 1% to about 3%

(w/w); k) valine or a salt thereof from about 5% to about 9% (w/w); l) arginine or a salt thereof from about 5% to about 9% (w/w); m) glutamine or a salt thereof from about 7% to about 11% (w/w); n) alanine or a salt thereof from about 4% to about 7% (w/w); o) aspartic acid or a salt thereof from about 6% to about 10% (w/w); p) asparagine or a salt thereof from about 3% to about 6% (w/w); q) glutamic acid or a salt thereof from about 8% to about 14% (w/w); and r) proline or a salt thereof from about 6% to about 10% (w/w). Any composition of the disclosure can include cysteine in place of cystine, or cystine in place of cysteine.

In some embodiments, a composition of the disclosure can comprise at least 2, 3, 4, 5, 6, 7, 8, 9, or 10 of: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); or m) glutamine or a salt thereof from about 7% to about 11% (w/w). In some embodiments, a composition can comprise in a unit dosage form: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); and m) glutamine or a salt thereof from about 7% to about 11% (w/w). Any composition of the disclosure can include cysteine in place of cystine, or cystine in place of cysteine.

In some embodiments, a composition can comprise at least 2, 3, 4, 5, 6, 7, 8, 9, 10, 11, 12, 13, 14, or 15 of: a) histidine, a hydrate thereof, or a salt thereof from about 3% to about 7% (w/w); b) isoleucine, a hydrate thereof, or a salt thereof from about 3% to about 6% (w/w); c) leucine, a hydrate thereof, or a salt thereof from about 7% to about 11% (w/w); d) lysine, a hydrate thereof, or a salt thereof from about 5% to about 9% (w/w); e) methionine, a hydrate thereof, or a salt thereof from about 2% to about 4% (w/w); f) cysteine, a hydrate thereof, or a salt thereof from about 1% to about 3% (w/w); g) phenylalanine, a hydrate thereof, or a salt thereof from about 3% to about 7% (w/w); h) tyrosine, a hydrate thereof, or a salt thereof from about 1% to about 3% (w/w); i) threonine, a hydrate thereof, or a salt thereof from about 2% to about 5% (w/w); j) tryptophan, a hydrate thereof, or a salt thereof from about 1% to about 3% (w/w); k) valine, a hydrate thereof, or a salt thereof from about 5% to about 9% (w/w); l) arginine, a hydrate thereof, or a salt thereof from about 5% to about 9% (w/w); m) glutamine, a hydrate thereof, or a salt thereof from about 7% to about 11% (w/w); n) alanine, a hydrate thereof, or a salt thereof from about 3% to about 7% (w/w); o) aspartic acid, a hydrate thereof, or a salt thereof from about 6% to about 10% (w/w); p) asparagine, a hydrate thereof, or a salt thereof from about 3% to about 6% (w/w); q) glutamic acid, a hydrate thereof, or a salt thereof from about 8% to about 14% (w/w); r) serine, a hydrate thereof, or a salt thereof from about 2% to about 5% (w/w); and s) glycine, a hydrate thereof, or a salt thereof from about 3% to about 7% (w/w). Any composition of the disclosure can include cysteine in place of cystine, or cystine in place of cysteine.

In some embodiments, a composition can comprise at least 2, 3, 4, 5, 6, 7, 8, 9, 10, 11, 12, 13, 14, or 15 of: a) histidine, a hydrate thereof, or a salt thereof from about 3% to about 7% (w/w); b) isoleucine, a hydrate thereof, or a salt thereof from about 4% to about 8% (w/w); c) leucine, a hydrate thereof, or a salt thereof from about 9% to about 13% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 4% (w/w); g) phenylalanine, a hydrate thereof, or a salt thereof from about 5% to about 9% (w/w); h) tyrosine, a hydrate thereof, or a salt thereof from about 1% to about 5% (w/w); i) threonine, a hydrate thereof, or a salt thereof from about 4% to about 8% (w/w); j) tryptophan, a hydrate thereof, or a salt thereof from about 1% to about 4% (w/w); k) valine, a hydrate thereof, or a salt thereof from about 5% to about 10% (w/w); l) arginine, a hydrate thereof, or a salt thereof from about 1% to about 10% (w/w); m) glutamine, a hydrate thereof, or a salt thereof from about 1% to about 5% (w/w); n) alanine, a hydrate thereof, or a salt thereof from about 4% to about 8% (w/w); o) aspartic acid, a hydrate thereof, acid or a salt thereof from about 4% to about 12% (w/w); p) asparagine, a hydrate thereof, or a salt thereof from about 4% to about 8% (w/w); or q) glutamic acid, a hydrate thereof, or a salt thereof from about 5% to about 15% (w/w). In some embodiments, a composition can comprise in a unit dosage form: a) histidine, a hydrate thereof, or a salt thereof from about 3% to about 7% (w/w); b) isoleucine, a hydrate thereof, or a salt thereof from about 4% to about 8% (w/w); c) leucine, a hydrate thereof, or a salt thereof from about 9% to about 13% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 4% (w/w); g) phenylalanine, a hydrate thereof, or a salt thereof from about 5% to about 9% (w/w); h) tyrosine, a hydrate thereof, or a salt thereof from about 1% to about 5% (w/w); i) threonine, a hydrate thereof, or a salt thereof from about 4% to about 8% (w/w); j) tryptophan, a hydrate thereof, or a salt thereof from about 1% to about 4% (w/w); k) valine, a hydrate thereof, or a salt thereof from about 5% to about 10% (w/w); l) arginine, a hydrate thereof, or a salt thereof from about 1% to about 10% (w/w); m) glutamine, a hydrate thereof, or a salt thereof from about 1% to about 5% (w/w); n) alanine, a hydrate thereof, or a salt thereof from about 4% to about 8% (w/w); o) aspartic acid, a hydrate thereof, acid or a salt thereof from about 4% to about 12% (w/w); p) asparagine, a hydrate thereof, or a salt thereof from about 4% to about 8% (w/w); and q) glutamic acid, a hydrate thereof, or a salt thereof from about 5% to about 15% (w/w). Any composition of the disclosure can include cysteine in place of cystine, or cystine in place of cysteine.

In some embodiments, a composition can comprise at least 2, 3, 4, 5, 6, 7, 8, 9, 10, 11, 12, 13, 14, or 15 of: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 9% to about 12% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 3% (w/w); g) phenylalanine, a hydrate thereof, or a salt thereof from about 6% to about 8% (w/w); h) tyrosine, a hydrate thereof, or a salt thereof from about 1% to about 4% (w/w); i) threonine, a hydrate thereof, or a salt thereof from about 4% to about 7% (w/w); j) tryptophan, a hydrate thereof, or a salt thereof from about 1% to about 3% (w/w); k) valine, a hydrate thereof, or a salt thereof from about 4% to about 9% (w/w); l) arginine, a hydrate thereof, or a salt thereof from about 7% to about 11% (w/w); m) glutamine, a hydrate thereof, or a salt thereof from about 2% to about 4% (w/w); n) alanine, a hydrate thereof, or a salt thereof from about 4% to about 7% (w/w); o) aspartic acid, a hydrate thereof, or a salt thereof from about 8% to about 11% (w/w); p) asparagine, a hydrate thereof, or a salt thereof from about 4% to about 7% (w/w); or q) glutamic acid, a hydrate thereof, or a salt thereof from about 4% to about 8% (w/w). In some embodiments, a composition can comprise in a unit dosage form: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 9% to about 12% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 3% (w/w); g) phenylalanine, a hydrate thereof, or a salt thereof from about 6% to about 8% (w/w); h) tyrosine, a hydrate thereof, or a salt thereof from about 1% to about 4% (w/w); i) threonine, a hydrate thereof, or a salt thereof from about 4% to about 7% (w/w); j) tryptophan, a hydrate thereof, or a salt thereof from about 1% to about 3% (w/w); k) valine, a hydrate thereof, or a salt thereof from about 4% to about 9% (w/w); l) arginine, a hydrate thereof, or a salt thereof from about 7% to about 11% (w/w); m) glutamine, a hydrate thereof, or a salt thereof from about 2% to about 4% (w/w); n) alanine, a hydrate thereof, or a salt thereof from about 4% to about 7% (w/w); o) aspartic acid, a hydrate thereof, or a salt thereof from about 8% to about 11% (w/w); p) asparagine, a hydrate thereof, or a salt thereof from about 4% to about 7% (w/w); and q) glutamic acid, a hydrate thereof, or a salt thereof from about 4% to about 8% (w/w). Any composition of the disclosure can include cysteine in place of cystine, or cystine in place of cysteine.

In some embodiments, a composition can comprise at least 2, 3, 4, 5, 6, 7, 8, 9, 10, 11, 12, 13, 14, or 15 of: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 11% to about 13% (w/w); d) lysine, a hydrate thereof, or a salt thereof from about 8% to about 10% (w/w); e) methionine, a hydrate thereof, or a salt thereof from about 2% to about 4% (w/w); f) phenylalanine, a hydrate thereof, or a salt thereof from about 6% to about 8% (w/w); g) tyrosine, a hydrate thereof, or a salt thereof from about 1% to about 3% (w/w); h) threonine, a hydrate thereof, or a salt thereof from about 3% to about 5% (w/w); i) tryptophan, a hydrate thereof, or a salt thereof from about 1% to about 3% (w/w); j) valine, a hydrate thereof, or a salt thereof from about 8% to about 10% (w/w); k) arginine, a hydrate thereof, or a salt thereof from about 7% to about 9% (w/w); l) alanine, a hydrate thereof, or a salt thereof from about 3% to about 5% (w/w); m) aspartic acid, a hydrate thereof, or a salt thereof from about 4% to about 6% (w/w); n) asparagine, a hydrate thereof, or a salt thereof from about 4% to about 7% (w/w); or o) proline, a hydrate thereof, or a salt thereof from about 14% to about 17% (w/w). In some embodiments, a composition can comprise in a unit dosage form: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 11% to about 13% (w/w); d) lysine, a hydrate thereof, or a salt thereof from about 8% to about 10% (w/w); e) methionine, a hydrate thereof, or a salt thereof from about 2% to about 4% (w/w); f) phenylalanine, a hydrate thereof, or a salt thereof from about 6% to about 8% (w/w); g) tyrosine, a hydrate thereof, or a salt thereof from about 1% to about 3% (w/w); h) threonine, a hydrate thereof, or a salt thereof from about 3% to about 5% (w/w); i) tryptophan, a hydrate thereof, or a salt thereof from about 1% to about 3% (w/w); j) valine, a hydrate thereof, or a salt thereof from about 8% to about 10% (w/w); k) arginine, a hydrate thereof, or a salt thereof from about 7% to about 9% (w/w); l) alanine, a hydrate thereof, or a salt thereof from about 3% to about 5% (w/w); m) aspartic acid, a hydrate thereof, or a salt thereof from about 4% to about 6% (w/w); n) asparagine, a hydrate thereof, or a salt thereof from about 4% to about 7% (w/w); and o) proline, a hydrate thereof, or a salt thereof from about 14% to about 17% (w/w). Any composition of the disclosure can include cysteine in place of cystine, or cystine in place of cysteine.

Pharmaceutically-acceptable salts.

Any molecular component of the pharmaceutical compositions described herein (e.g., an amino acid) can be provided as a pharmaceutically-acceptable salt. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a trimethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pyridazine salt, a pyrimidine salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Vitamins

A composition of the disclosure can comprise one or more essential vitamins. In some embodiments, a composition of the disclosure can comprise vitamin A, vitamin C, vitamin D, vitamin E, vitamin K, and vitamin B. In some embodiments, a composition of the disclosure can comprise thiamine (vitamin B1), riboflavin (vitamin B2), niacin (vitamin B3), pantothenic acid (vitamin B5), pyridoxine (vitamin B6), biotin (vitamin B7), folate (vitamin B9), or cobalamin (vitamin B12). In some embodiments, a composition of the disclosure can comprise a fat-soluble vitamin, such as vitamin A, vitamin D, vitamin E, or vitamin K. In some embodiments, a composition of the disclosure can comprise a water-soluble vitamin, such as vitamin C and vitamin B. In some embodiments, a composition of the disclosure can comprise a water-soluble vitamin, such as vitamin B, such as thiamine (vitamin B1), riboflavin (vitamin B2), niacin (vitamin B3), pantothenic acid (vitamin B5), pyridoxine (vitamin B6), biotin (vitamin B7), folate (vitamin B9), or cobalamin (vitamin B12).

In some embodiments, a composition of the disclosure can comprise vitamin A, vitamin B, vitamin C, vitamin D, and vitamin E. In some embodiments, a composition of the disclosure can comprise vitamin A, vitamin C, vitamin D, vitamin E, thiamine (vitamin B1), riboflavin (vitamin B2), niacin (vitamin B3), pantothenic acid (vitamin B5), pyridoxine (vitamin B6), biotin (vitamin B7), folate (vitamin B9), and cobalamin (vitamin B12).

A composition of the disclosure can comprise the recommended dietary allowance of vitamins in a male adult. In some embodiments, a composition of the disclosure comprises the recommended dietary allowance of vitamins in a male adult: vitamin A, 900 µg; vitamin C, 90 mg; vitamin D, 15 µg; vitamin E, 15 mg; vitamin K, 120 µg; thiamine, 1.2 mg; riboflavin, 1.3 mg; niacin, 16 mg; pantothenic acid, 5 mg; pyridoxine, 1.3 mg; biotin, 30 µg; folate, 400 µg; and choline, 550 mg. A composition of the disclosure can comprise the recommended dietary allowance of vitamins in a female adult. In some embodiments, a composition of the disclosure comprises the recommended dietary allowance of vitamins in a female adult: vitamin A, 700 µg; vitamin C, 75 mg; vitamin D, 15 µg; vitamin E, 15 mg; vitamin K, 90 µg; thiamine, 1.1 mg; riboflavin, 1.1 mg; niacin, 14 mg; pantothenic acid, 5 mg; pyridoxine, 1.3 mg; biotin, 30 µg; folate, 400 µg; and choline, 425 mg.

A composition of the disclosure can comprise about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of any of the recommended dietary allowance of vitamins in a male or female adult. In some embodiments, a composition of the disclosure can comprise about 20%, about 30%, about 40%, about 50%, or about 60% of any of the recommended dietary allowance of vitamins in a male or female adult. In some embodiments, a composition of the disclosure can comprise about 30% of any of the recommended dietary allowance of vitamins in a male or female adult. In some embodiments, a composition of the disclosure can comprise about 50% of any of the recommended dietary allowance of vitamins in a male or female adult.

Minerals

A composition of the disclosure can comprise one or more minerals or elements. In some embodiments, a composition of the disclosure can comprise calcium, chromium, copper, fluoride, iodide, iron, magnesium, manganese, molybdenum, phosphorous, selenium, zinc, potassium, sodium, or chloride.

A composition of the disclosure can comprise the recommended daily allowance of elements or minerals in a male adult. In some embodiments, a composition of the disclosure comprises a recommended daily allowance of elements or minerals in a male adult: calcium, 1000 mg; chromium, 35 µg; copper, 900 µg; fluoride, 4 mg; iodide, 150 µg; iron, 8 mg; magnesium, 400 mg; manganese, 2.3 mg; molybdenum, 45 µg; phosphorous, 700 mg; selenium, 55 µg; zinc, 11 mg;

potassium, 3400 mg; sodium, 1500 mg; or chloride, 2.3 g. A composition of the disclosure can comprise the recommended daily allowance of elements or minerals in a female adult. In some embodiments, a composition of the disclosure comprises a recommended daily allowance of elements or minerals in a female adult: calcium, 1000 mg; chromium, 25 µg; copper, 900 µg; fluoride, 3 mg; iodide, 150 µg; iron, 18 mg; magnesium, 310 mg; manganese, 1.8 mg; molybdenum, 45 µg; phosphorous, 700 mg; selenium, 55 µg; zinc, 8 mg; potassium, 2600 mg; sodium, 1500 mg; or chloride, 2.3 g.

A composition of the disclosure can comprise about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of any of the recommended dietary allowance of elements or minerals in a male or female adult. In some embodiments, a composition of the disclosure can comprise about 20%, about 30%, about 40%, about 50%, or about 60% of any of the recommended dietary allowance of elements or minerals in a male or female adult. In some embodiments, a composition of the disclosure can comprise about 30% of any of the recommended dietary allowance of elements or minerals in a male or female adult. In some embodiments, a composition of the disclosure can comprise about 50% of any of the recommended dietary allowance of elements or minerals in a male or female adult.

Lipids

A composition of the disclosure can comprise fat. In some embodiments, a pharmaceutical composition of the disclosure can comprise saturated fat, trans fat, polyunsaturated fat, or monounsaturated fat. In some embodiments, a composition of the disclosure can comprise saturated fat, trans fat, polyunsaturated fat, and monounsaturated fat.

In some embodiments, a composition of the disclosure can comprise about 1 g, about 2 g, about 3 g, about 4 g, about 5 g, about 6 g, about 7 g, about 8 g, about 9 g, or about 10 g of combined fat content. In some embodiments, a composition of the disclosure can comprise about 5 g of combined fat content.

In some embodiments, a composition of the disclosure comprises cholesterol. In some embodiments, a composition of the disclosure comprises about 100 mg/serving of cholesterol. In some embodiments, a composition of the disclosure comprises about 50 mg/serving of cholesterol.

Carbohydrates

In some embodiments, a composition of the disclosure comprises a carbohydrate, such as a sugar, starch, or complex carbohydrate. In some embodiments, a composition of the disclosure comprises a sugar, such as corn syrup, fructose, galactose, glucose, high fructose corn syrup, lactose, maltose, or sucrose. In some embodiments, a composition of the disclosure comprises a sugar alcohol. In some embodiments, a composition of the disclosure comprises a starch. In some embodiments, a composition of the disclosure comprises a resistant starch, such as oats, rice, legumes, raw potato starch, green bananas, or Hi-Maize® flour.

In some embodiments, a composition of the disclosure comprises a complex carbohydrate, such as fiber. In some embodiments, a composition of the disclosure comprises a soluble fiber. In some embodiments, a composition of the disclosure comprises soluble fiber obtained from a food source, such as oatmeal, flax seed, barley, dried peas, apples, or carrots. In some embodiments, a composition of the disclosure comprises a insoluble fiber. In some embodiments, a composition of the disclosure comprises insoluble fiber obtained from a food source, such as seeds, nuts, dark green leafy vegetables, or wheat bran. In some embodiments, a composition of the disclosure comprises fiber, such as inulin, methylcellulose, psyllium, or wheat dextrin.

Pharmaceutical Excipients

A composition of the disclosure can comprise at least one pharmaceutical excipient, such as an anti-adherent, a binder, coating, colorant, disintegrant, flavorant, preservative, sorbent, sweetener, or vehicle. In some embodiment, a composition of the disclosure comprises a colorant and a flavorant. In some embodiment, a composition of the disclosure comprises a colorant, flavorant, and sweetener. In some embodiment, a composition of the disclosure comprises a flavorant, sweetener, and a preservative.

A. Anti-Adherent

A composition of the disclosure can comprise an anti-adherent. In some embodiments, a composition of the disclosure can comprise an anti-adherent, such as magnesium stearate.

B. Binding Agent

A composition of the disclosure can comprise at least one binding agent to hold the composition together. In some embodiments, a composition of the disclosure can comprise a binding agent, such as a saccharide, protein, or synthetic polymer. In some embodiments, a composition of the disclosure can comprise a disaccharide (e.g., sucrose or lactose), a polysaccharide or polysaccharide derivative (e.g., starch, cellulose, modified cellulose, cellulose ether), or a sugar alcohol (e.g., xylitol, sorbitol, or mannitol). In some embodiments, a composition of the disclosure can comprise a protein binder, such as gelatin. In some embodiments, a composition of the disclosure can comprise a synthetic polymer binder, such as polyvinylpyrrolidone (PVP) or polyethylene glycol (PEG).

C. Preservatives

A composition of the disclosure can comprise at least one preservative. In some embodiments, a composition of the disclosure can comprise an antioxidant or an antimicrobial. Antioxidant agents delay or prevent the deterioration of the composition by oxidative mechanisms. Antimicrobial agents inhibit the growth of spoilage or pathogenic microorganisms in the composition.

In some embodiments, an antioxidant agent is added to the composition to delay or prevent autooxidation of unsaturated fatty acids or enzyme-catalyzed oxidation. In some embodiments, a composition of the disclosure comprises at least one of ascorbic acid, butylated hydroxyanisole (BHA), butylated hydroxytoluene (BHT), citric acid, a sulfite, tertiary butylhydroquinone (TBHQ), or a tocopherol. In some embodiments, a composition of the disclosure comprises ascorbic acid. In some embodiments, a composition of the disclosure comprises BHT. In some embodiments, a composition of the disclosure comprises citric acid.

In some embodiments, a composition of the disclosure comprises about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of an antioxidant agent. In some embodiments, a composition of the disclosure comprises up to about 100 mg/kg, up to about 200 mg/kg, up to about 300 mg/kg, up to about 400 mg/kg, up to about 500 mg/kg, up to about 600 mg/kg, up to about 700 mg/kg, up to about 800 mg/kg, up to about 900 mg/kg, or up to about 1000 mg/kg of an antioxidant agent.

In some embodiments, an antimicrobial agent is added to the composition to delay or prevent growth of spoilage or pathogenic microorganisms in the composition. In some embodiments, a composition of the disclosure comprises at least one of acetic acid, benzoic acid, natamycin, nisin, a nitrate, a nitrite, propionic acid, sorbic acid, a sulfite, or sulfur dioxide.

In some embodiments, a composition of the disclosure comprises about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of an antimicrobial agent. In some embodiments, a composition of the disclosure comprises up to about 100 mg/kg, up to about 200 mg/kg, up to about 300 mg/kg, up to about 400 mg/kg, up to about 500 mg/kg, up to about 600 mg/kg, up to about 700 mg/kg, up to about 800 mg/kg, up to about 900 mg/kg, or up to about 1000 mg/kg of an antimicrobial agent.

D. Colorants

A composition of the disclosure can comprise at least one colorant. In some embodiments, a composition of the disclosure comprises a natural colorant or a synthetic colorant.

In some embodiments, a composition of the disclosure comprises a natural colorant. In some embodiments, a composition of the disclosure comprises an anthocyanin. In some embodiments, a composition of the disclosure comprises an anthocyanin, such as pelargonidin-3-glucoside obtained from strawberries (Fragaria species) or malvidin-3-glucoside obtained from grapes (*Vitis* species). In some embodiments, a composition of the disclosure comprises a betacyanin. In some embodiments, a composition of the disclosure comprises a betacyanin, such as betanin obtained from beet root (*Beta vulgaris*). In some embodiments, a composition of the disclosure comprises a carotenoid. In some embodiments, a composition of the disclosure comprises a carotenoid, such as bixin obtained from annatto (*Bixa Orellana*); crocin obtained from saffron (*Crocus sativus*); capsanthin obtained from paprika (*Capsicum annuum*); beta-carotene obtained from carrot (*Daucus carota*); or canthaxanthin obtained from mushrooms (*Cantharellus cinnabarinus*). In some embodiments, a composition of the disclosure comprises a phenolic. In some embodiments, a composition of the disclosure comprises a phenolic, such as curcumin obtained from turmeric (*Cuycuma longa*).

In some embodiments, a composition of the disclosure comprises a synthetic colorant. In some embodiments, a composition of the disclosure comprises allura red AC, brilliant blue FCF, erythrosine, fast green FCF, indico carmine, sunset yellow FCF, or tartrazine. In some embodiments, a composition of the disclosure comprises FD&C red no. 40, FD&C blue no. 1, FD&C red no. 3, FD&C green no. 3, FD&C blue no. 2, FD&C yellow no. 6, or FD&C yellow no. 5. In some embodiments, a composition of the disclosure comprises E133, E127, E132, E110, or E102.

E. Flavorants

A composition of the disclosure can comprise at least one flavoring agent. In some embodiments, a composition of the disclosure can comprise a natural flavoring substance, a nature-identical flavoring substance, or an artificial flavoring substance. In some embodiments, a composition of the disclosure can comprise a natural flavoring substance, such as a spice, fruit juice, or vegetable juice. In some embodiments, a composition of the disclosure can comprise a nature-identical flavoring substance, such as vanillin.

In some embodiments, a composition of the disclosure can comprise an artificial flavoring substance, such as allylpyrazine, methoxypyrazine, 2-iso-butyl-3-methoxypyrazine, acetyl-L-pyrazine, 2-acetoxy pyrazine, aldehydes, alcohols, esters, ketones, pyrazines, phenolics, or terpenoids.

F. Sweetener

A composition of the disclosure can comprise at least one sweetener. In some embodiments, a composition of the disclosure comprises sucrose, glucose, fructose, corn syrup, high-fructose corn syrup, or a sugar alcohol. In some embodiments, a composition of the disclosure comprises a sugar alcohol, such as sorbitol, mannitol, or xylitol. In some embodiments, a composition of the disclosure comprises fructose.

In some embodiments, a composition of the disclosure comprises a synthetic sweetener. In some embodiments, a composition of the disclosure comprises saccharin, a cyclamate, aspartame, or acesulfame K. In some embodiments, a composition of the disclosure comprises aspartame.

In some embodiments, a composition of the disclosure can comprise a sweetener in an amount of about 0.5 g/serving, about 1 g/serving, about 1.5 g/serving, about 2 g/serving, about 2.5 g/serving, about 3 g/serving, about 3.5 g/serving, about 4 g/serving, about 4.5 g/serving, about 5 g/serving, about 5.5 g/serving, about 6 g/serving, about 6.5 g/serving, about 7 g/serving, about 7.5 g/serving, about 8 g/serving, about 8.5 g/serving, about 9 g/serving, about 9.5 g/serving, or about 10 g/serving. In some embodiments, a composition of the disclosure can comprise about 1 g/serving of a sweetener. In some embodiments, a composition of the disclosure can comprise about 2.5 g/serving of a sweetener. In some embodiments, a composition of the disclosure can comprise about 5 g/serving of a sweetener.

G. Processing Agents

A composition of the disclosure can comprise at least one processing additive. In some embodiments, a composition of the disclosure can comprise an anticaking agent, a bleaching agent, a chelating agent, a clarifying agent, conditioning agent, emulsifying agent, a humectant, a pH control agent, a stabilizing agent, or a thickening agent. In some embodiments, a composition of the disclosure can comprise an anticaking agent such as sodium aluminosilicate, a chelating agent such as ethylenediaminetetraacetic acid (EDTA), a conditioning agent such as potassium bromate, or a pH control agent such as citric acid or lactic acid. In some embodiments, a composition of the disclosure can comprise a humectant such as glycerol, or a stabilizing and thickening agent such as pectin, gelatin, carrageenan, or guar gum.

Formulations

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Dosing

A composition described herein can be given to supplement a meal consumed by a subject. A composition described herein can be given as a meal replacement. A composition described herein can be given immediately before or immediately after a meal. A composition described here can be given within about 5 minutes, about 10 minutes, about 15 minutes, about 20 minutes, about 25 minutes, about 30 minutes, about 40 minutes, about one hour, about 2 hours, about 3 hours, about 4 hours, about 5 hours, or about 6 hours before or after a meal.

A composition described herein can be in unit dosage forms suitable for single administration of precise dosages. In unit dosage form, the formulation is divided into unit doses containing appropriate quantities of the composition. In some embodiments, the unit dosage can be in the form of a package containing discrete quantities of the formulation. In some embodiments, formulations of the disclosure can be presented in unit dosage form in single-serving sachet. In some embodiments, formulations of the disclosure can be presented in a single-dose non-reclosable container. In some embodiments, a formulation of the disclosure can be presented in a reclosable container, and the subject can obtain a single-dose serving of the formulation using a scoop or spoon designed to distribute a single-dose serving. In some embodiments, a formulation of the disclosure can be presented in a reclosable container, and the subject can obtain a single-dose serving of the formulation using a scoop or spoon designed to distribute a half-dose serving (i.e., two scoops to distribute one serving).

A composition described herein can be present in a unit dose serving in a range from about 1 g to about 2 g, from about 2 g to about 3 g, from about 3 g to about 4 g, from about 4 g to about 5 g, from about 5 g to about 6 g, from about 6 g to about 7 g, from about 7 g to about 8 g, from about 8 g to about 9 g, from about 9 g to about 10 g, from about 10 g to about 11 g, from about 11 g to about 12 g, from about 12 g to about 13 g, from about 13 g to about 14 g, from about 14 g to about 15 g, from about 15 g to about 16 g, from about 16 g to about 17 g, from about 17 g to about 18 g, from about 18 g to about 19 g, from about 19 g to about 20 g, from about 20 g to about 21 g, from about 21 g to about 22 g, from about 22 g to about 23 g, from about 23 g to about 24 g, or from about 24 g to about 25 g.

A composition described herein can be present in a unit dose serving in an amount of about 1 g, about 2 g, about 3 g, about 4 g, about 5 g, about 6 g, about 7 g, about 8 g, about 9 g, about 10 g, about 11 g, about 12 g, about 13 g, about 14 g, about 15 g, about 16 g, about 17 g, about 18 g, about 19 g, about 20 g, about 21 g, about 22 g, about 23 g, about 24 g, or about 25 g. In some embodiments, a composition described herein is present in a unit dose serving in an amount of about 10 g, 12 g, 15 g, 20 g, or 24 g.

In some embodiments, a composition described herein is present in a unit dose serving in an amount of about 12 g. In some embodiments, a composition described herein is present in a unit dose serving in a sachet in an amount of about 12 g. In some embodiments, a composition described herein is present in a unit dose serving in an amount of about 15 g. In some embodiments, a composition described herein is present in a unit dose serving in a sachet in an amount of about 15 g. In some embodiments, a composition described herein is present in a unit dose serving in an amount of about 24 g. In some embodiments, a composition described herein is present in a unit dose serving in a sachet in an amount of about 24 g.

In some embodiments, a dose of a composition of the disclosure can be expressed in terms of an amount of the drug divided by the mass of the subject, for example, grams of drug per kilograms of subject body mass. In some embodiments, a therapeutically-effective amount of a composition of the disclosure is from about 0.1 g/kg/day to about 0.2 g/kg/day, from about 0.2 g/kg/day to about 0.3 g/kg/day, from about 0.3 g/kg/day to about 0.4 g/kg/day, from about 0.4 g/kg/day to about 0.5 g/kg/day, from about 0.5 g/kg/day to about 0.6 g/kg/day, from about 0.6 g/kg/day to about 0.7 g/kg/day, from about 0.7 g/kg/day to about 0.8 g/kg/day, from about 0.8 g/kg/day to about 0.9 g/kg/day, from about 0.9 g/kg/day to about 1.0 g/kg/day, from about 1.0 g/kg/day to about 1.1 g/kg/day, from about 1.1 g/kg/day to about 1.2 g/kg/day, from about 1.2 g/kg/day to about 1.3 g/kg/day, from about 1.3 g/kg/day to about 1.4 g/kg/day, or from about 1.4 g/kg/day to about 1.5 g/kg/day. In some embodiments, a therapeutically-effective amount of a composition of the disclosure is from about 0.4 g/kg/day to about 0.5 g/kg/day. In some embodiments, a therapeutically-effective amount of a composition of the disclosure is from about 0.6 g/kg/day to about 0.7 g/kg/day. In some embodiments, a therapeutically-effective amount of a composition of the disclosure is from about 0.8 g/kg/day to about 0.9 g/kg/day.

A composition described herein can be provided to a subject to achieve an amount of protein per body weight of the subject. In some embodiments, a composition described herein can be provided to a subject to achieve a range from about 0.2 g protein/kg to about 0.4 g protein/kg, about 0.4 g protein/kg to about 0.6 g protein/kg, about 0.6 g protein/kg to about 0.8 g protein/kg, or about 0.8 g protein/kg to about 1 g protein/kg of body weight of the subject. In some embodiments, a composition described herein can be provided to a subject to achieve a range from about 0.6 g protein/kg to about 0.8 g protein/kg of body weight of the subject.

A composition described herein can be provided to a subject in one or more servings per day. In some embodiments, 1 serving, 2 servings, 3 servings, 4 servings, 5 servings, 6 servings, 7 servings, 8 servings, 9 servings, 10 servings, 11 servings, or 12 servings of a composition described herein is provided to a subject in one day. In some embodiments, 3 servings of a composition described herein is provided to a subject in one day. In some embodiments, 6 servings of a composition described herein is provided to a subject in one day. In some embodiments, 9 servings of a composition described herein is provided to a subject in one day.

Methods of Administration

A composition of the disclosure can be administered to a subject in the form of a liquid drink. In some embodiments, a drink is prepared for the subject by dissolving one or more sachets of a composition of the disclosure in a liquid without substantial nutrients. In some embodiments, a drink is prepared for the subject by dissolving one or more sachets of a composition of the disclosure in water. In some embodiments, a drink is prepared for the subject by dissolving one or more sachets of a composition of the disclosure in juice. In some embodiments, a drink is prepared for the subject by dissolving one or more sachets of a composition of the disclosure in an electrolyte drink.

In some embodiments, a drink is prepared for the subject by dissolving one or more sachets of a composition of the disclosure in water, and a flavorant is added to the mixture. In some embodiments, at least one drop of a flavorant drop, such as Mio liquid water enhancer, is added to a mixture of a pharmaceutical composition of the disclosure in water. In some embodiments, a flavorant powder, such as Squash Stix™ water enhancer, is added to a mixture of a composition of the disclosure in water.

In some embodiments, a drink is prepared for the subject by dissolving one or more sachets of a composition of the disclosure in water, and a dietary supplement gel or dietary supplement premade drink is added to the mixture. In some embodiments, a dietary supplement gel, such as Vitaflo Gel™, is added to a mixture of a composition of the disclosure in water. In some embodiments, a dietary supplement premade drink, such as Vitaflo Cooler™, is added to a mixture of a composition of the disclosure in water.

In some embodiments, a composition is prepared as a pre-made drink in a bottle or carton.

A composition of the disclosure can be administered to a subject, and the administration can be accompanied by a food-based diet low in or substantially devoid of at least one amino acid. In some embodiments, administration of a composition of the disclosure is accompanied by a food-based diet low in or substantially devoid of one amino acid. In some embodiments, administration of a composition of the disclosure is accompanied by a food-based diet low in or substantially devoid of serine. In some embodiments, administration of a composition of the disclosure is accompanied by a food-based diet low in or substantially devoid of glycine. In some embodiments, administration of a composition of the disclosure is accompanied by a food-based diet low in or substantially devoid of two amino acids or salts thereof. In some embodiments, administration of a composition of the disclosure is accompanied by a food-based diet low in or substantially devoid of serine and glycine. In some embodiments, administration of a composition of the disclosure is accompanied by a food-based diet low in or substantially devoid of three amino acids or salts thereof. In some embodiments, administration of a composition of the disclosure is accompanied by a food-based diet low in or substantially devoid of four amino acids or salts thereof. A salt of an amino acid disclosed herein can be a pharmaceutically acceptable salt.

A composition of the disclosure that is devoid of an amino acid can be administered with a diet that comprises at most about 500 mg/day, at most about 450 mg/day, at most about 400 mg/day, at most about 350 mg/day, at most about 300 mg/day, at most about 250 mg/day, at most about 200 mg/day, at most about 150 mg/day, or at most about 100 mg/day of the amino acid. In some embodiments, a composition of the disclosure that is devoid of an amino acid can be administered with a diet that comprises at most about 450 mg/day of the amino acid. In some embodiments, a composition of the disclosure that is devoid of an amino acid can be administered with a diet that comprises at most about 400 mg/day of the amino acid. In some embodiments, a composition of the disclosure that is devoid of an amino acid can be administered with a diet that comprises at most about 350 mg/day of the amino acid. In some embodiments, a composition of the disclosure that is devoid of an amino acid can be administered with a diet that comprises at most about 250 mg/day of the amino acid. In some embodiments, a composition devoid of proline is administered with a diet that comprises at most about 450 mg/day of proline. In some embodiments, a composition devoid of proline is administered with a diet that comprises at most about 350 mg/day of proline. In some embodiments, a composition devoid of proline is administered with a diet that comprises at most about 250 mg/day of proline.

A composition of the disclosure that is devoid of a first amino acid and a second amino acid can be administered with a diet that comprises at most about 500 mg/day, at most about 450 mg/day, at most about 400 mg/day, at most about 350 mg/day, at most about 300 mg/day, at most about 250 mg/day, at most about 200 mg/day, at most about 150 mg/day, or at most about 100 mg/day of the first amino acid and at most about 500 mg/day, at most about 450 mg/day, at most about 400 mg/day, at most about 350 mg/day, at most about 300 mg/day, at most about 250 mg/day, at most about 200 mg/day, at most about 150 mg/day, or at most about 100 mg/day of the second amino acid. In some embodiments, a composition of the disclosure that is devoid of a first amino acid and a second amino acid can be administered with a diet that comprises at most about 450 mg/day of the first amino acid and at most about 300 mg/day of the second amino acid. In some embodiments, a composition of the disclosure that is devoid of a first amino acid and a second amino acid can be administered with a diet that comprises at most about 450 mg/day of the first amino acid and at most about 250 mg/day of the second amino acid. In some embodiments, a composition of the disclosure that is devoid of a first amino acid and a second amino acid can be administered with a diet that comprises at most about 350 mg/day of the first amino acid and at most about 250 mg/day of the second amino acid. In some embodiments, a composition of the disclosure that is devoid of a first amino acid and a second amino acid can be administered with a diet that comprises at most about 400 mg/day of the first amino acid and at most about 250 mg/day of the second amino acid.

A composition of the disclosure can be administered to a subject that is on a diet. In some embodiments, a composition of the disclosure is administered to the subject, and the subject is on a diet that is low in protein. In some embodiments, a composition of the disclosure is administered to the subject, and the subject is on a low carbohydrate diet. In some embodiments, a composition of the disclosure is administered to the subject, and the subject is on a high-fat, and low-carbohydrate (e.g. ketogenic type diet). In some embodiments, a composition of the disclosure is administered to the subject, and the subject is on a vegetarian diet. In some embodiments, a composition of the disclosure is administered to the subject, and the subject is on a vegan diet.

In some embodiments, a composition of the disclosure is administered to a subject that is on a low protein diet that is also low in at least one non-essential amino acid. In some embodiments, a composition of the disclosure is administered to a subject that is on a low protein diet that is also low in serine and glycine. In some embodiments, a composition of the disclosure is administered to a subject that is on a low protein diet with less than about 2 g/day, about 1.75 g/day, about 1.5 g/day, about 1.25 g/day, about 1 g/day, about 0.75 g/day, or about 0.5 g/day in serine or glycine. In some embodiments, a composition of the disclosure is administered to a subject that is on a low protein diet with less than about 500 mg/day, about 450 mg/day, about 400 mg/day, about 350 mg/day, about 300 mg/day, about 250 mg/day, about 200 mg/day, about 150 mg/day, about 100 mg/day, or about 50 mg/day in serine or glycine.

In some embodiments, a composition of the disclosure is administered to a subject with a low glucose, whole-food diet.

In some embodiments, a composition of the disclosure is administered to a subject with a low protein diet. In some embodiments, a composition of the disclosure is administered to a subject with a low protein, whole food diet. In some embodiments, a composition of the disclosure is administered to a subject with a low protein, whole food diet comprising at most about 15 g protein/day, at most about 14 g protein/day, at most about 13 g protein/day, at most about 12 g protein/day, at most about 11 g protein/day, at most about 10 g protein/day, at most about 9 g protein/day, at most about 8 g protein/day, at most about 7 g protein/day, at most about 6 g protein/day, or at most about 5 g protein/day. In some embodiments, a composition of the disclosure is administered to a subject with a low protein, whole food diet comprising at most about 12 g protein/day. In some embodiments, a composition of the disclosure is administered to a subject with a low protein, whole food diet comprising at most about 11 g protein/day. In some embodiments, a composition of the disclosure is administered to a subject with a low protein, whole food diet comprising at most about 10 g protein/day. In some embodiments, a composition of the disclosure is administered to a subject with a low protein, whole food diet comprising at most about 9 g protein/day. In some embodiments, a composition of the disclosure is administered to a subject with a low protein, whole food diet comprising at most about 8 g protein/day.

In some embodiments, a composition of the disclosure is administered to a subject with a diet deriving at most about 60%, at most about 55%, at most about 50%, at most about 45%, at most about 40%, at most about 35%, at most about 30%, at most about 25%, at most about 20%, at most about 15%, at most about 10%, or at most about 5% of a daily caloric intake from carbohydrates. In some embodiments, a composition of the disclosure is administered to a subject with a diet deriving at most about 50% of a daily caloric intake from carbohydrates. In some embodiments, a composition of the disclosure is administered to a subject with a diet deriving at most about 25% of a daily calory intake from carbohydrates. In some embodiments, a composition of the disclosure is administered to a subject with a diet deriving at most about 15% of a daily calory intake from carbohydrates. In some embodiments, a composition of the disclosure is administered to a subject with a diet deriving at most about 9% of a daily calory intake from carbohydrates.

In some embodiments, a composition of the disclosure is administered to a subject with a diet deriving at most about 10%, at most about 9%, at most about 8%, at most about 7%, at most about 6%, at most about 5%, at most about 4.5%, at most about 4%, at most about 3.5%, at most about 3%, at most about 2.5%, at most about 2%, at most about 1.5%, or at most about 1% of a daily caloric intake from protein. In some embodiments, a composition of the disclosure is administered to a subject with a diet deriving at most about 3% of a daily caloric intake from protein. In some embodiments, a composition of the disclosure is administered to a subject with a diet deriving at most about 2.5% of a daily caloric intake from protein. In some embodiments, a composition of the disclosure is administered to a subject with a diet deriving at most about 2% of a daily caloric intake from protein. In some embodiments, a composition of the disclosure is administered to a subject with a diet deriving at most about 1.5% of a daily caloric intake from protein.

In some embodiments, a composition of the disclosure is administered to a subject with a diet deriving at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, or at least about 30% of a daily caloric intake from fats. In some embodiments, a composition of the disclosure is administered to a subject with a diet deriving at least about 45% of a daily caloric intake from fats. In some embodiments, a composition of the disclosure is administered to a subject with a diet deriving at least about 60% of a daily caloric intake from fats. In some embodiments, a composition of the disclosure is administered to a subject with a diet deriving at least about 80% of a daily caloric intake from fats. In some embodiments, a composition of the disclosure is administered to a subject with a diet deriving at least about 90% of a daily caloric intake from fats.

A composition of the disclosure can be administered to a subject that is administered at least one supplement. In some embodiments, a composition of the disclosure is administered to the subject with an energy supplement. In some embodiments, a composition of the disclosure is administered to the subject with an energy supplement, such as caffeine, guarana, Asian ginseng, vitamin B12, or coenzyme Q10. In some embodiments, a composition of the disclosure is administered to the subject with an energy supplement, such as caffeine, tyrosine, pyrroloquinoline quinone (PQQ), theanine, coenzyme Q10, acetyl-L-carnitine (ALCAR), alpha-lipoic acid (ALA), citicoline, creatine, citrulline, beetroot powder, Ashwagandha, or Rhoodiola rosea. In some embodiments, a composition of the disclosure is administered to the subject with coenzyme Q10.

In some embodiments, a composition of the disclosure is administered to the subject with a micronutrient supplement. In some embodiments, a composition of the disclosure is administered to the subject with a multivitamin. In some embodiments, a composition of the disclosure is administered to the subject with a vitamin supplement, such as vitamin C or vitamin D supplement. In some embodiments, a composition of the disclosure is administered to the subject with a mineral supplement, such as an iron or zinc supplement.

In some embodiments, a composition of the disclosure is administered to the subject with an energy supplement and a micronutrient supplement. In some embodiments, a composition of the disclosure is administered to a subject with coenzyme Q10 and a multivitamin. In some embodiments, a composition of the disclosure is administered to a subject with coenzyme Q10 and a mineral supplement.

In some embodiments, a composition of the disclosure is administered to a subject as a nutritionally complete product. In some embodiments, the composition is administered as a meal replacement shake or powder. In some embodiments, the composition is administered via an enteral feeding tube.

Multiple therapeutic agents can be administered in any order or simultaneously. In some embodiments, a composition of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms.

A composition disclosed herein can be administered as soon as is practical after the onset of a disease or condition is detected or suspected, and for a length of time necessary for the treatment of the disease. In some embodiments, the length of time necessary for the treatment of disease is about 12 hours, about 24 hours, about 36 hours, or about 48 hours. In some embodiments, the length of time necessary for the treatment of disease is about 1 day, about 2 days, about 3 days, about 4 days, about 5 days, about 6 days, about 7 days, about 8 days, about 9 days, about 10 days, about 11 days, about 12 days, about 13 days, about 14 days, or about 15 days. In some embodiments, the length of time necessary for the treatment of disease is about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, or about 20 weeks. In some embodiments, the length of time necessary for the treatment of disease is about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

A composition of the disclosure can be administered continuously. In some embodiments, a composition of the disclosure can be administered continuously for about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

In some embodiments, a composition of the disclosure can be administered an early stage of the disease. In some embodiments, a composition of the disclosure can be administered a later stage of the disease. In some embodiments, a composition of the disclosure can be administered during a pre-symptomatic stage of disease. In some embodiments, a composition of the disclosure can be administered during a symptomatic stage of disease. In some embodiments, a composition of the disclosure can be administered during a severe stage of disease.

A composition of the disclosure can be administered intermittently. In some embodiments, a composition of the disclosure can be administered for a first number of days with a modified diet, and a normal/habitual diet (i.e., diet typical of the subject before administration of composition) can be administered for a second number of days, and the composition/modified diet and normal/habitual diet cycle can be repeated. In some embodiments, a composition of the disclosure can be administered for 1 day with a modified diet, and a normal/habitual diet can be administered for 1 day, and the composition/modified diet and normal/habitual diet cycle can be repeated. In some embodiments, a composition of the disclosure can be administered for 1 day with a modified diet, and a normal/habitual diet can be administered for 2 days, and the composition/modified diet and normal/habitual diet cycle can be repeated. In some embodiments, a composition of the disclosure can be administered for 1 day with a modified diet, and a normal/habitual diet can be administered for 3 days, and the composition/modified diet and normal/habitual diet cycle can be repeated. In some embodiments, a composition of the disclosure can be administered for 1 day with a modified diet, and a normal/habitual diet can be administered for 4 days, and the composition/modified diet and normal/habitual diet cycle can be repeated. In some embodiments, a composition of the disclosure can be administered for 1 day with a modified diet, and a normal/habitual diet can be administered for 5 days, and the composition/modified diet and normal/habitual diet cycle can be repeated. In some embodiments, a composition of the disclosure can be administered for 1 day with a modified diet, and a normal/habitual diet can be administered for 6 days, and the composition/modified diet and normal/habitual diet cycle can be repeated.

In some embodiments, a composition of the disclosure can be administered for 2 days with a modified diet, and a normal/habitual diet (i.e., diet typical of the subject before administration of composition) can be administered for 1 day, and the composition/modified diet and normal/habitual diet cycle can be repeated. In some embodiments, a composition of the disclosure can be administered for 2 days with a modified diet, and a normal/habitual diet can be administered for 2 days, and the composition/modified diet and normal/habitual diet cycle can be repeated. In some embodiments, a composition of the disclosure can be administered for 2 days with a modified diet, and a normal/habitual diet can be administered for 3 days, and the composition/modified diet and normal/habitual diet cycle can be repeated. In some embodiments, a composition of the disclosure can be administered for 2 days with a modified diet, and a normal/habitual diet can be administered for 4 days, and the composition/modified diet and normal/habitual diet cycle can be repeated. In some embodiments, a composition of the disclosure can be administered for 2 days with a modified diet, and a normal/habitual diet can be administered for 5 days, and the composition/modified diet and normal/habitual diet cycle can be repeated.

In some embodiments, a composition of the disclosure can be administered for 3 days with a modified diet, and a normal/habitual (i.e., diet typical of the subject before administration of composition) diet can be administered for 1 day, and the composition/modified diet and normal/habitual diet cycle can be repeated. In some embodiments, a composition of the disclosure can be administered for 3 days with a modified diet, and a normal/habitual diet can be administered for 2 days, and the composition/modified diet and normal/habitual diet cycle can be repeated. In some embodiments, a composition of the disclosure can be administered for 3 days with a modified diet, and a normal/habitual diet can be administered for 3 days, and the composition/modified diet and normal/habitual diet cycle can be repeated. In some embodiments, a composition of the disclosure can be administered for 3 days with a modified diet, and a normal/habitual diet can be administered for 4 days, and the composition/modified diet and normal/habitual diet cycle can be repeated.

In some embodiments, a composition of the disclosure can be administered for 4 days with a modified diet, and a normal/habitual diet (i.e., diet typical of the subject before administration of composition) can be administered for 1 day, and the composition/modified diet and normal/habitual diet cycle can be repeated. In some embodiments, a composition of the disclosure can be administered for 4 days with a modified diet, and a normal/habitual diet can be administered for 2 days, and the composition/modified diet and normal/habitual diet cycle can be repeated. In some embodiments, a composition of the disclosure can be administered for 4 days with a modified diet, and a normal/habitual diet can be administered for 3 days, and the composition/modified diet and normal/habitual diet cycle can be repeated.

In some embodiments, a composition of the disclosure can be administered for 5 days with a modified diet, and a normal/habitual diet (i.e., diet typical of the subject before administration of composition) can be administered for 1 days, and the composition/modified diet and normal/habitual diet cycle can be repeated. In some embodiments, a composition of the disclosure can be administered for 5 days with a modified diet, and a normal/habitual diet can be administered for 2 days, and the composition/modified diet and normal/habitual diet cycle can be repeated. In some embodiments, a composition of the disclosure can be administered for 6 days with a modified diet, and a normal/habitual diet can be administered for 1 day, and the composition/modified diet and normal/habitual diet cycle can be repeated.

In some embodiments, a composition of the disclosure can be administered for a first number of days with a modified diet, and a normal/habitual diet (i.e., diet typical of the subject before administration of composition) can be administered for a second number of days, and the composition/modified diet and normal habitual diet cycle can be repeated 1, 2, 3, 4, 5, 6, 7, 8, 9, or 10 times. In some embodiments, a composition of the disclosure can be administered for a first number of days with a modified diet, and a normal/habitual diet can be administered for a second number of days, and the composition/modified diet and normal habitual diet cycle can be repeated 5 times.

In some embodiments, a composition of the disclosure can be administered for a first number of days with a modified diet, and a normal/habitual diet (i.e., diet typical of the subject before administration of composition) can be administered for a second number of days, and the composition/modified diet and normal habitual diet cycle can be repeated for about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

A composition of the disclosure can be administered 1, 2, 3, 4, 5, 6, 7, or 8 times a day, spread throughout a 24 hour period. In some embodiments, a composition of the disclosure can be administered 1 time a day. In some embodiments, a composition of the disclosure can be administered 2 times a day. In some embodiments, a composition of the disclosure can be administered 3 times a day. In some embodiments, a composition of the disclosure can be administered 4 times a day. In some embodiments, a composition of the disclosure can be administered 5 times a day. In some embodiments, a composition of the disclosure can be administered 6 times a day.

A composition described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Aqueous suspension compositions can be packaged in single-dose non-reclosable containers. Multiple-dose reclosable containers can be used, for example, in combination with or without a preservative.

In some embodiments, a composition is administered to a subject throughout a day. In some embodiments, a composition is administered to a subject with a meal. In some embodiments, a composition is administered to a subject with a snack. In some embodiments, a composition is administered to a subject without a meal. In some embodiments, a composition is administered to a subject through the day in equal intervals. In some embodiments, a first serving is administered before breakfast, a second serving is administered with breakfast, a third serving is administered with lunch, a fourth and fifth serving is administered with dinner, and a sixth serving is administered before bed.

A composition provided herein can be administered in conjunction with other therapies, for example, chemotherapy, radiation, surgery, anti-inflammatory agents, immunotherapy, biologicals, and selected vitamins. The other agents can be administered prior to, after, or concomitantly with the pharmaceutical compositions.

Methods of Use of a Composition Disclosed Herein.

The present disclosure provides methods for treating a subject. A composition disclosed herein can be used in the treatment of any disease. In some embodiments, a composition disclosed herein is used to treat cancer in a subject in need thereof. Altering the diet and nutrient of a subject can have desired health benefits and can be efficacious in the treatment of disease.

Based on the particular disease and/or need of the patient, the present disclosure provides methods for generalized-treatment recommendation for a subject as well as methods for subject-specific treatment recommendation. Methods for treatments can comprise one of the following steps: determining a level of a nutrient in a subject; detecting a presence or absence of a disease in the subject based upon the determining, and recommending to the subject at least one generalized or subject-specific treatment to ameliorate disease symptoms.

In some embodiments, a composition disclosed herein can be used to manage a disease or condition by a dietary intervention. In some embodiments, a composition disclosed herein can be used as part of a treatment plan for a particular disease or condition.

In some embodiments, the subject has cancer. Cancer is caused by uncontrollable growth of neoplastic cells, leading to invasion of adjacent and distant tissues resulting in death. Cancer cells often have underlying genetic or epigenetic abnormalities that affect both coding and regulatory regions of the genome. Genetic abnormalities in cancer cells can change protein structures, dynamic and expression levels, which in turn alter the cellular metabolism of the cancer cells. Changes in cell cycles can make cancer cells proliferate at a much higher speed than normal cells. With the increased metabolic rate and proliferation, cancer tissues have much higher nutrient demands compared to normal tissues.

Cancer cells have nutrient auxotrophy and have a much higher nutrient demand compared to normal cells. As an adaptation to fulfill the increased nutritional demand, cancer cells can upregulate the glucose and amino acid transporters on the cell membrane to obtain more nutrients from circulation. Cancer cells can also rewire metabolic pathways by enhancing glycolysis and glutaminolysis to sustain a higher rate of ATP production or energy supply. Glucose and amino acids are highly demanded nutrients in cancer cells. Some cancer cell types and tumor tissues are known to be auxotrophic to specific amino acids. Cancers' auxotrophy to different amino acids can render the cancer types vulnerable to amino acid starvation treatments.

When mammalian cells experience amino acid starvation, the cells undergo a homeostatic response to amino acid shortage. Amino acid deficiency can trigger a general amino acid control pathway that involves shifting resources and energy of cells to expression of membrane transporters, growth hormones, and metabolic enzymes for amino acid homeostasis. Up-regulation of membrane transporters can enhance amino acid uptake, and up-regulation of metabolic enzymes can enhance amino acid synthesis. The cells can also recycle proteins and organelles to regenerate non-essential amino acids by autophagy. By general amino acid control pathway and autophagy, cells attempt to maintain amino acid homeostasis. Tumor tissues can also overcome amino acid starvation by enhancing angiogenesis to obtain more nutrient supply.

When homeostasis cannot be achieved upon severe amino acid starvation, cancer cells can inhibit protein synthesis, suppress growth, or undergo programmed cell death. The cell death mechanisms of amino acid starvation can be caspase-dependent apoptosis, autophagic cell death, or ferroptotic cell death. Amino acid transporters, metabolic enzymes, autophagy-associated proteins, and amino acid starvation can be used to control cancer growth.

A method disclosed herein can monitor nutrient consumption by a subject. The nutrient consumption can be measured by taking a biological sample from a subject. The biological sample can be for example, whole blood, serum, plasma, mucosa, saliva, cheek swab, urine, stool, cells, tissue, bodily fluid, sweat, breath, lymph fluid, CNS fluid, and lesion exudates. A combination of biological samples can be used with the methods of the disclosure.

A method of composition of the disclosure can slow the proliferation of cancer cell lines, or kill cancer cells. Non-limiting examples of cancer that can be treated by a compound of the disclosure include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the methods of the disclosure can be used to treat breast cancer. In some embodiments, the methods of the disclosure can be used to colorectal cancer. In some embodiments, the methods of the disclosure can be used to treat pancreatic cancer.

Therapeutic Effects.

In some embodiments, the present disclosure provides a composition comprising in a powder form: a) an essential amino acid, wherein the essential amino acid is not part of polypeptide; b) a non-essential amino acid, wherein the non-essential is not part of a polypeptide; and c) a pharmaceutically acceptable excipient. In some embodiments, the composition does not comprise serine, glycine, and cysteine. In some embodiments, the composition does not comprise serine, glycine, and glutamic acid, glutamine, and cystine. In some embodiments, the composition does not comprise proline. In some embodiments, the composition does not comprise serine and glycine.

Administering a composition can modulate the serum amino acid level of at least one amino acid. In some embodiments, administering a composition devoid of an amino acid can decrease the serum amino acid level of the amino acid. In some embodiments, administering a composition devoid of an amino acid can decrease the serum amino acid level of the amino acid by from about 10% to about 20%, from about 20% to about 30%, from about 30% to about 40%, from about 40% to about 50%, from about 50% to about 60%, from about 60% to about 70%, from about 70% to about 80%, from about 80% to about 90%. In some embodiments, administering a composition devoid of an amino acid can decrease the serum amino acid level of the amino acid by from about 10% to about 20%. In some embodiments, administering a composition devoid of an amino acid can decrease the serum amino acid level of the amino acid by from about 20% to about 30%. In some embodiments, administering a composition devoid of an amino acid can decrease the serum amino acid level of the amino acid by about 5%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, administering a composition devoid of an amino acid can decrease the serum amino acid level of the amino acid by about 10%. In some embodiments, administering a composition devoid of an amino acid can decrease the serum amino acid level of the amino acid by about 20%. In some embodiments, administering a composition devoid of an amino acid can decrease the serum amino acid level of the amino acid by about 30%.

Administering a composition devoid of a first amino acid can reduce serum amino acids of at least 2, 3, 4, 5, 6, 7, 8, 9 or 10 amino acids. In some embodiments, administering a composition devoid of a first amino acid can reduce serum amino acids of at least the first amino acid and a second amino acid. In some embodiments, administering a composition devoid of a first amino acid can reduce serum amino acids of at least the first amino acid, a second amino acid, and a third amino acid. In some embodiments, administering a composition devoid of a first amino acid can reduce serum amino acids of at least the first amino acid, a second amino acid, a third amino acid, and a fourth amino acid. In some embodiments, administering a composition devoid of a first amino acid can reduce serum amino acids of at least the first amino acid, a second amino acid, a third amino acid, a fourth amino acid, and a fifth amino acid.

Administering a composition of the disclosure devoid of an amino acid can change the serum amino acid level of the amino acid for a prolonged period of time. In some embodiments, administering a composition of the disclosure devoid of an amino acid can reduce the serum amino acid level of the amino acid for a prolonged period of time. In some embodiments, administering a composition of the disclosure devoid of an amino acid can reduce the serum amino acid level of the amino acid for at least about 4 hours, at least about 8 hours, at least about 12 hours, at least about 16 hours, at least about 20 hours, at least about 24 hours, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In some embodiments, administering a composition of the disclosure devoid of an amino acid can reduce the serum amino acid level of the amino acid for at least about 4 hours, at least about 2 days. In some embodiments, administering a composition of the disclosure devoid of an amino acid can reduce the serum amino acid level of the amino acid for at least about 4 hours, at least about 4 days. In some embodiments, administering a composition of the disclosure devoid of an amino acid can reduce the serum amino acid level of the amino acid for at least about 4 hours, at least about 2 weeks. In some embodiments, administering a composition of the disclosure devoid of an amino acid can reduce the serum amino acid level of the amino acid for at least about 4 hours, at least about 4 weeks.

A composition of the disclosure can decrease cell proliferation in a subject. In some embodiments, administering a composition of a disclosure can decrease cell proliferation in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200% compared to a subject that is not administered the dietary composition. In some embodiments, a composition of the disclosure can decrease cell proliferation in a subject receiving a cancer therapy compared to a subject that is receiving the cancer therapy but not the composition of the disclosure. In some embodiments, administering a composition of a disclosure can decrease cell proliferation in a subject by from about 20% to about 25% compared to a subject that is not administered the dietary composition. In some embodiments, administering a composition of a disclosure can decrease cell proliferation in a subject by from about 50% to about 75% compared to a subject that is not administered the dietary composition.

In some embodiments, administering a composition of a disclosure can decrease cell proliferation in a subject by about 5%, about 10%, about 15%, about 20%, about 25%, about 30%, about 35%, about 40%, about 45%, about 50%, about 75%, about 100%, about 125%, about 150%, about 175%, or about 200% compared to a subject that is not administered the dietary composition. In some embodiments, a composition of the disclosure can decrease cell proliferation in a subject receiving a cancer therapy compared to a subject that is receiving the cancer therapy but not the composition of the disclosure. In some embodiments, administering a composition of a disclosure can decrease cell proliferation in a subject by about 20% compared to a subject that is not administered the dietary composition. In some embodiments, administering a composition of a disclosure can decrease cell proliferation in a subject by about 30% compared to a subject that is not administered the dietary composition. In some embodiments, administering a composition of a disclosure can decrease cell proliferation in a subject by about 50% compared to a subject that is not administered the dietary composition. In some embodiments, administering a composition of a disclosure can decrease cell proliferation in a subject by about 70% compared to a subject that is not administered the dietary composition.

In some embodiments, administering a composition of the disclosure can decrease a tumor volume in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200%. In some embodiments, a composition of the disclosure can decrease a tumor volume in a subject receiving a cancer therapy compared to a subject that is receiving the cancer therapy but not the composition of the disclosure. In some embodiments, administering a composition of the disclosure can decrease a tumor volume in a subject by from about 20% to about 25%. In some embodiments, administering a composition of the disclosure can decrease a tumor volume in a subject by from about 45% to about 50%.

In some embodiments, administering a composition of the disclosure can decrease a tumor volume in a subject by about 5%, about 10%, about 15%, about 20%, about 25%, about 30%, about 35%, about 40%, about 45%, about 50%, about 75%, about 100%, about 125%, about 150%, about 175%, or about 200%. In some embodiments, a composition of the disclosure can decrease a tumor volume in a subject receiving a cancer therapy compared to a subject that is receiving the cancer therapy but not the composition of the disclosure. In some embodiments, administering a composition of the disclosure can decrease a tumor volume in a subject by about 20%. In some embodiments, administering a composition of the disclosure can decrease a tumor volume in a subject by about 30%. In some embodiments, administering a composition of the disclosure can decrease a tumor volume in a subject by about 50%.

Administering a composition of the disclosure can increase overall survival of a subject. In some embodiments, administering a composition of the disclosure can increase overall survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, a composition of the disclosure can increase overall survival of a subject receiving a cancer therapy compared to a subject that is receiving the cancer therapy but not the composition of the disclosure. In some embodiments, administering a composition of the disclosure can increase overall survival of a subject by at least about 10%. In some embodiments, administering a composition of the disclosure can increase overall survival of a subject by at least about 20%. In some embodiments, administering a composition of the disclosure can increase overall survival of a subject by at least about 30%.

Administering a composition of the disclosure can increase progression free survival of a subject. In some embodiments, administering a composition of the disclosure can increase progression free survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, a composition of the disclosure can increase progression-free survival of a subject receiving a cancer therapy compared to a subject that is receiving the cancer therapy but not the composition of the disclosure. In some embodiments, administering a composition of the disclosure can increase progression free survival of a subject by at least about 10%. In some embodiments, administering a composition of the disclosure can increase progression free survival of a subject by at least about 20%. In some embodiments, administering a composition of the disclosure can increase progression free survival of a subject by at least about 30%.

Administering a composition of the disclosure can increase percentage of cancer cell death. In some embodiments, administering a composition of the disclosure can increase percentage of cancer cell death by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, a composition of the disclosure can increase percentage of cancer cell death in a subject receiving a cancer therapy compared to a subject that is receiving the cancer therapy but not the composition of the disclosure. In some embodiments, administering a composition of the disclosure can increase percentage of cancer cell death by at least about 10%. In some embodiments, administering a composition of the disclosure can increase percentage of cancer cell death by at least about 20%. In some embodiments, administering a composition of the disclosure can increase percentage of cancer cell death by at least about 30%.

Administering a composition of the disclosure can increase sensitivity to a cancer therapy in a subject. In some embodiments, administering a composition of the disclosure can increase sensitivity to a cancer therapy in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure can increase sensitivity to a cancer therapy in a subject by at least about 10%. In some embodiments, administering a composition of the disclosure can increase sensitivity to a cancer therapy in a subject by at least about 20%. In some embodiments, administering a composition of the disclosure can increase sensitivity to a cancer therapy in a subject by at least about 30%.

Administering a composition of the disclosure can increase a treatment response rate of a therapeutic agent. In some embodiments, administering a composition of the disclosure can increase a treatment response rate of a therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure can increase a treatment response rate of a therapeutic agent by at least about 10%. In some embodiments, administering a composition of the disclosure can increase a treatment response rate of a therapeutic agent by at least about 20%. In some embodiments, administering a composition of the disclosure can increase a treatment response rate of a therapeutic agent by at least about 30%.

Administering a composition of the disclosure with a therapeutic agent can increase the efficacy of the therapeutic agent in a subject compared to a subject treated only with the composition of the disclosure. In some embodiments, administering a composition of the disclosure with a therapeutic agent can increase the efficacy of the therapeutic agent in a subject by at least about at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated only with the composition of the disclosure. In some embodiments, administering a composition of the disclosure with a therapeutic agent can increase the efficacy of the therapeutic agent in a subject by at least about at least about 10% compared to a subject treated only with the composition of the disclosure. In some embodiments, administering a composition of the disclosure with a therapeutic agent can increase the efficacy of the therapeutic agent in a subject by at least about at least about 20% compared to a subject treated only with the composition of the disclosure. In some embodiments, administering a composition of the disclosure with a therapeutic agent can increase the efficacy of the therapeutic agent in a subject by at least about at least about 30% compared to a subject treated only with the composition of the disclosure.

Administering a composition of the disclosure with a therapeutic agent to a subject can decrease a dose of the therapeutic agent compared to a subject treated with the therapeutic agent alone to achieve the same outcome. In some embodiments, administering a composition of the disclosure with a therapeutic agent to a subject can decrease the required dose of the therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the therapeutic agent alone to achieve the same outcome. In some embodiments, administering a composition of the disclosure with a therapeutic agent to a subject can decrease the required dose of the therapeutic agent by at least about 10% compared to a subject treated with the therapeutic agent alone to achieve the same outcome. In some embodiments, administering a composition of the disclosure with a therapeutic agent to a subject can decrease the required dose of the therapeutic agent by at least about 20% compared to a subject treated with the therapeutic agent alone to achieve the same outcome. In some embodiments, administering a composition of the disclosure with a therapeutic agent to a subject can decrease the required dose of the therapeutic agent by at least about 30% compared to a subject treated with the therapeutic agent alone to achieve the same outcome.

Administering a composition of the disclosure with a therapeutic agent to a subject can decrease adverse events associated with an additional therapy compared to a subject treated with the additional therapy alone. In some embodiments, administering a composition of the disclosure with a therapeutic agent to a subject can decrease adverse events associated with an additional therapy by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the additional therapy alone. In some embodiments, administering a composition of the with a therapeutic agent to a subject can decrease adverse events associated with an additional therapy by at least about 10% compared to a subject treated with the additional therapy alone. In some embodiments, administering a composition of the disclosure with a therapeutic agent to a subject can decrease adverse events associated with an additional therapy by at least about 20% compared to a subject treated with the additional therapy alone. In some embodiments, administering a composition of the disclosure with a therapeutic agent to a subject can decrease adverse events associated with an additional therapy by at least about 30% compared to a subject treated with the additional therapy alone.

Kits

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

App-Based Coaching with Compositions of the Disclosure

A composition of the invention can be administered while the subject is coached on a coaching application. In some embodiments, the composition is in the form of a sachet. In some embodiments, the composition is in the form of a shake. In some embodiments, the composition contains all daily protein requirements for the subject. In some embodiments, the composition is supplemented with other dietary requirements.

In some embodiments, the coaching application can coach the subject by directing the subject to consume a precise amount of the composition. In some embodiments, the coaching application can coach the subject on the subject's food intake categories and amounts of each food. In some embodiments, the coaching application can provide a meal plan to eliminate a macronutrient category (e.g., protein) such that the composition can provide the subject's necessary macronutrients.

The coaching application can comprise educational materials. In some embodiments, the coaching application can comprise educational brochures, diet logging, biomarker feedback, or coaching with a dietitian or health professional.

EXAMPLES

Example 1: Amino Acid Formulations

Formulations of amino acids lacking 7 non-essential amino acids are prepared. Table 1 shows the ingredients of Formulation A, which contains histidine, isoleucine, leucine, lysine, methionine, phenylalanine, threonine, tryptophan, valine, cysteine, tyrosine, glutamine, and arginine. Table 1 also shows the amount of each amino acid (mg) included in a sachet containing about 12 g of the formulation.

TABLE 1

Formulation A

| | Amino acid | Percent of AA content | mg of AA in 12 g sachet |
|---|---|---|---|
| 1 | Histidine | 6.6 | 799 |
| 2 | Isoleucine | 6.6 | 799 |
| 3 | Leucine | 15.9 | 1917 |
| 4 | Lysine | 11.9 | 1438 |
| 5 | Methionine | 5.3 | 639 |
| 6 | Phenylalanine | 8.0 | 958 |
| 7 | Threonine | 8.0 | 958 |
| 8 | Tryptophan | 4.0 | 479 |
| 9 | Valine | 13.3 | 1597 |
| 10 | Cysteine | 2.1 | 250 |
| 11 | Tyrosine | 2.1 | 250 |
| 12 | Glutamine | 9.0 | 1083 |
| 13 | Arginine | 7.2 | 867 |
| 14 | Alanine | 0.0 | 0 |
| 15 | Aspartic Acid | 0.0 | 0 |
| 16 | Asparagine | 0.0 | 0 |
| 17 | Glutamic acid | 0.0 | 0 |
| 18 | Proline | 0.0 | 0 |
| 19 | Serine | 0.0 | 0 |
| 20 | Glycine | 0.0 | 0 |
| | Total | 100 | 12.035 g |

Table 2 shows the amount of each amino acid that is administered to a subject provided with 0.6 g/kg/day and 0.8 g/kg/day of protein. The amounts amino acids are presented as mg/kg/day.

TABLE 2

Formulation A; 0.6 g/kg/day and 0.8 g/kg/day protein

| | Amino acid | Percent of AA content | 0.6 g/kg/day (mg/kg/day) | 0.8 g/kg/day (mg/kg/day) |
|---|---|---|---|---|
| 1 | Histidine | 6.6 | 39.8 | 53.1 |
| 2 | Isoleucine | 6.6 | 39.8 | 53.1 |
| 3 | Leucine | 15.9 | 95.6 | 127.4 |
| 4 | Lysine | 11.9 | 71.7 | 95.6 |
| 5 | Methionine | 5.3 | 31.9 | 42.5 |
| 6 | Phenylalanine | 8.0 | 47.8 | 63.7 |
| 7 | Threonine | 8.0 | 47.8 | 63.7 |
| 8 | Tryptophan | 4.0 | 23.9 | 31.9 |
| 9 | Valine | 13.3 | 79.6 | 106.2 |
| 10 | Cysteine | 2.1 | 12.5 | 16.6 |
| 11 | Tyrosine | 2.1 | 12.5 | 16.6 |
| 12 | Glutamine | 9.0 | 54.0 | 72.0 |
| 13 | Arginine | 7.2 | 43.2 | 57.6 |
| 14 | Alanine | 0.0 | 0.0 | 0.0 |
| 15 | Aspartic Acid | 0.0 | 0.0 | 0.0 |
| 16 | Asparagine | 0.0 | 0.0 | 0.0 |
| 17 | Glutamic acid | 0.0 | 0.0 | 0.0 |
| 18 | Proline | 0.0 | 0.0 | 0.0 |
| 19 | Serine | 0.0 | 0.0 | 0 |
| 20 | Glycine | 0.0 | 0.0 | 0 |
| | Total | 100 | 600.0 | 800.0 |

Table 3 shows the amount of protein and number of sachets containing formulation A administered for patients supplemented with 0.8 g/kg/day of protein.

TABLE 3

Formulation A; Number of sachets administered to patients (0.8 g/kg/day)

| Patient weight (kg) | g of protein per day | Precise number of 12 g sachets per day | Rounded number of sachets per day |
|---|---|---|---|
| 50 | 40 | 3.33 | 3.5 |
| 60 | 48 | 4.00 | 4 |
| 70 | 56 | 4.67 | 5 |
| 80 | 64 | 5.33 | 5.5 |
| 90 | 72 | 6.00 | 6 |
| 100 | 80 | 6.67 | 7 |
| 110 | 88 | 7.33 | 7.5 |
| 120 | 96 | 8.00 | 8 |

Table 4 shows the amount of protein and number of sachets containing formulation A administered for patients supplemented with 0.6 g/kg/day of protein.

TABLE 4

Formulation A; Number of sachets administered to patients (0.6 g/kg/day)

| Patient weight (kg) | g of protein per day | Precise number of 12 g sachets per day | Rounded number of sachets per day |
|---|---|---|---|
| 50 | 30 | 2.50 | 2.5 |
| 60 | 36 | 3.00 | 3 |
| 70 | 42 | 3.50 | 2.5 |
| 80 | 48 | 4.00 | 4 |
| 90 | 54 | 4.50 | 4.5 |
| 100 | 60 | 5.00 | 5 |
| 110 | 66 | 5.50 | 5.5 |
| 120 | 72 | 6.00 | 6 |

Example 2: Amino Acid Formulation Lacking a Single Amino Acid

Formulations lacking one amino acid are prepared. Tables 5-10 show formulations lacking tyrosine, arginine, glutamic acid, glutamine, aspartic acid, or alanine.

TABLE 5

Formulation lacking tyrosine

| | Amino acid | Percent of AA content |
|---|---|---|
| 1 | Histidine | 3.3 |
| 2 | Isoleucine | 3.3 |
| 3 | Leucine | 8.0 |
| 4 | Lysine | 6.0 |
| 5 | Methionine | 2.7 |
| 6 | Phenylalanine | 4.0 |
| 7 | Threonine | 4.0 |
| 8 | Tryptophan | 2.0 |
| 9 | Valine | 6.7 |
| 10 | Cysteine | 1.9 |
| 11 | Tyrosine | 0 |
| 12 | Glutamine | 8.3 |
| 13 | Arginine | 6.6 |
| 14 | Alanine | 5.1 |
| 15 | Aspartic Acid | 7.6 |
| 16 | Asparagine | 4.4 |
| 17 | Glutamic acid | 10.2 |
| 18 | Proline | 7.6 |
| 19 | Serine | 2.8 |
| 20 | Glycine | 5.5 |
| | Total | 100.0 |

TABLE 6

Formulation lacking arginine

| | Amino acid | Percent of AA content |
|---|---|---|
| 1 | Histidine | 3.7 |
| 2 | Isoleucine | 3.7 |
| 3 | Leucine | 8.9 |
| 4 | Lysine | 6.7 |
| 5 | Methionine | 3.0 |
| 6 | Phenylalanine | 4.5 |
| 7 | Threonine | 4.5 |
| 8 | Tryptophan | 2.2 |
| 9 | Valine | 7.5 |
| 10 | Cysteine | 1.9 |
| 11 | Tyrosine | 1.9 |
| 12 | Glutamine | 8.3 |
| 13 | Arginine | 0 |
| 14 | Alanine | 5.1 |
| 15 | Aspartic Acid | 7.6 |
| 16 | Asparagine | 4.4 |
| 17 | Glutamic acid | 10.2 |
| 18 | Proline | 7.6 |
| 19 | Serine | 2.8 |
| 20 | Glycine | 5.5 |
| | Total | 100.0 |

TABLE 7

Formulation lacking glutamic acid

| | Amino acid | Percent of AA content |
|---|---|---|
| 1 | Histidine | 4.0 |
| 2 | Isoleucine | 4.0 |
| 3 | Leucine | 9.7 |
| 4 | Lysine | 7.2 |
| 5 | Methionine | 3.2 |

TABLE 7-continued

Formulation lacking glutamic acid

| | Amino acid | Percent of AA content |
|---|---|---|
| 6 | Phenylalanine | 4.8 |
| 7 | Threonine | 4.8 |
| 8 | Tryptophan | 2.4 |
| 9 | Valine | 8.0 |
| 10 | Cysteine | 1.9 |
| 11 | Tyrosine | 1.9 |
| 12 | Glutamine | 8.3 |
| 13 | Arginine | 6.6 |
| 14 | Alanine | 5.1 |
| 15 | Aspartic Acid | 7.6 |
| 16 | Asparagine | 4.4 |
| 17 | Glutamic acid | 0 |
| 18 | Proline | 7.6 |
| 19 | Serine | 2.8 |
| 20 | Glycine | 5.5 |
| | Total | 100.0 |

TABLE 8

Formulation lacking glutamine

| | Amino acid | Percent of AA content |
|---|---|---|
| 1 | Histidine | 3.9 |
| 2 | Isoleucine | 3.9 |
| 3 | Leucine | 9.3 |
| 4 | Lysine | 7.0 |
| 5 | Methionine | 3.1 |
| 6 | Phenylalanine | 4.6 |
| 7 | Threonine | 4.6 |
| 8 | Tryptophan | 2.3 |
| 9 | Valine | 7.7 |
| 10 | Cysteine | 1.9 |
| 11 | Tyrosine | 1.9 |
| 12 | Glutamine | 0 |
| 13 | Arginine | 6.6 |
| 14 | Alanine | 5.1 |
| 15 | Aspartic Acid | 7.6 |
| 16 | Asparagine | 4.4 |
| 17 | Glutamic acid | 10.2 |
| 18 | Proline | 7.6 |
| 19 | Serine | 2.8 |
| 20 | Glycine | 5.5 |
| | Total | 100.0 |

Table 9

Formulation lacking aspartic acid

| | Amino acid | Percent of AA content |
|---|---|---|
| 1 | Histidine | 3.8 |
| 2 | Isoleucine | 3.8 |
| 3 | Leucine | 9.1 |
| 4 | Lysine | 6.9 |
| 5 | Methionine | 3.0 |
| 6 | Phenylalanine | 4.6 |
| 7 | Threonine | 4.6 |
| 8 | Tryptophan | 2.3 |
| 9 | Valine | 7.6 |
| 10 | Cysteine | 1.9 |
| 11 | Tyrosine | 1.9 |
| 12 | Glutamine | 8.3 |
| 13 | Arginine | 6.6 |
| 14 | Alanine | 5.1 |
| 15 | Aspartic Acid | 0 |
| 16 | Asparagine | 4.4 |
| 17 | Glutamic acid | 10.2 |
| 18 | Proline | 7.6 |

Table 9-continued

Formulation lacking aspartic acid

| | Amino acid | Percent of AA content |
|---|---|---|
| 19 | Serine | 2.8 |
| 20 | Glycine | 5.5 |
| | Total | 100.0 |

TABLE 10

Formulation lacking alanine

| | Amino acid | Percent of AA content |
|---|---|---|
| 1 | Histidine | 3.6 |
| 2 | Isoleucine | 3.6 |
| 3 | Leucine | 8.6 |
| 4 | Lysine | 6.5 |
| 5 | Methionine | 2.9 |
| 6 | Phenylalanine | 4.3 |
| 7 | Threonine | 4.3 |
| 8 | Tryptophan | 2.2 |
| 9 | Valine | 7.2 |
| 10 | Cysteine | 1.9 |
| 11 | Tyrosine | 1.9 |
| 12 | Glutamine | 8.3 |
| 13 | Arginine | 6.6 |
| 14 | Alanine | 0 |
| 15 | Aspartic Acid | 7.6 |
| 16 | Asparagine | 4.4 |
| 17 | Glutamic acid | 10.2 |
| 18 | Proline | 7.6 |
| 19 | Serine | 2.8 |
| 20 | Glycine | 5.5 |
| | Total | 100.0 |

Table 11 shows a formulation supplemented with potassium and magnesium, and lacking asparagine. Table 12 shows a taurine and glucose-supplemented formulation, and lacking proline.

TABLE 11

Formulation lacking asparagine.

| | Amino acid | Milligrams (mg) | % of composition (w/w) |
|---|---|---|---|
| 1 | L-Histidine | 445.00 | 3.6 |
| 2 | L-Isoleucine | 650.00 | 5.2 |
| 3 | L-Leucine | 1,250.00 | 10.0 |
| 4 | L-Lysine HCl | 930.00 | 7.4 |
| 5 | L-Methionine | 330.00 | 2.6 |
| 6 | L-Phenylalanine | 650.00 | 5.2 |
| 7 | L-Threonine | 500.00 | 4 |
| 8 | L-Tryptophan | 200.00 | 1.6 |
| 9 | L-Valine | 920.00 | 7.4 |
| 10 | L-Cystine | 138.00 | 1.1 |
| 11 | L-Tyrosine | 250.00 | 2 |
| 12 | L-Glutamine | 900.00 | 7.2 |
| 13 | L-Arginine Base | 850.00 | 6.8 |
| 14 | L-Alanine | 450.00 | 3.6 |
| 15 | L-Aspartic Acid | 800.00 | 6.4 |
| 16 | L-Asparagine Hydrate | 0.00 | 0 |
| 17 | L-Glutamic Acid | 1,300.00 | 10.4 |
| 18 | L-Serine | 330.00 | 2.6 |
| 19 | Glycine | 550.00 | 4.4 |
| 20 | L-Proline | 1,000.00 | 8 |
| 21 | Taurine | 50.00 | 0.4 |
| | Total Amino Acids | 12,493.00 | |

TABLE 12

Taurine and glucose-supplemented formulation, and lacking proline

| | Amino acid | Milligrams (mg) | % of composition (w/w) | % of AA content (w/w) |
|---|---|---|---|---|
| 1 | L-Histidine HCl | 480.00 | 2.2 | 4 |
| 2 | L-Isoleucine | 650.00 | 3 | 5.4 |
| 3 | L-Leucine | 1,250.00 | 5.7 | 10.4 |
| 4 | L-Lysine HCl | 930.00 | 4.2 | 7.8 |
| 5 | L-Methionine | 330.00 | 1.5 | 2.8 |
| 6 | L-Phenylalanine | 650.00 | 3 | 5.4 |
| 7 | L-Threonine | 500.00 | 2.3 | 4.2 |
| 8 | L-Tryptophan | 200.00 | 0.9 | 1.7 |
| 9 | L-Valine | 920.00 | 4.2 | 7.7 |
| 10 | L-Cystine | 138.00 | 0.6 | 1.2 |
| 11 | L-Tyrosine | 250.00 | 1.1 | 2.1 |
| 12 | L-Glutamine | 900.00 | 4.1 | 7.5 |
| 13 | L-Arginine Base | 850.00 | 3.9 | 7.1 |
| 14 | L-Alanine | 450.00 | 2 | 3.8 |
| 15 | L-Aspartic Acid | 800.00 | 3.6 | 6.7 |
| 16 | L-Asparagine Hydrate | 450.00 | 2 | 3.8 |
| 17 | L-Glutamic Acid | 1,300.00 | 5.9 | 10.9 |
| 18 | L-Serine | 330.00 | 1.5 | 2.8 |
| 19 | Glycine | 550.00 | 2.5 | 4.6 |
| 20 | L-Proline | 0.00 | 0 | 0 |
| 21 | Taurine | 50.00 | 0.2 | 0.4 |
| | Total Amino Acids | 11,978.00 | 54.5 | 100 |
| | Other Materials | | | |
| 22 | Potassium Chloride (KCl) | 0 | 0 | — |
| 23 | Magnesium Citrate ($C_6H_6MgO_7$) | 0 | 0 | — |
| 24 | D-Glucose | 10,000.00 | 45.5 | — |
| | Total Materials | 21,978.00 | 100 | — |

Example 3: Amino Acid Formulation Lacking More than One Amino Acid

Formulations lacking two amino acids are prepared. Table 13 shows a formulation lacking serine and glycine.

TABLE 13

Formulation lacking serine and glycine

| | Amino acid | Percent of AA content |
|---|---|---|
| 1 | Histidine | 3.46 |
| 2 | Isoleucine | 3.46 |
| 3 | Leucine | 8.31 |
| 4 | Lysine | 6.23 |
| 5 | Methionine | 2.77 |
| 6 | Phenylalanine | 4.16 |
| 7 | Threonine | 4.16 |
| 8 | Tryptophan | 2.08 |
| 9 | Valine | 6.93 |
| 10 | Cysteine | 2.08 |
| 11 | Tyrosine | 2.08 |
| 12 | Glutamine | 9.00 |
| 13 | Arginine | 7.20 |
| 14 | Alanine | 5.54 |
| 15 | Aspartic Acid | 8.31 |
| 16 | Asparagine | 4.85 |
| 17 | Glutamic acid | 11.08 |
| 18 | Proline | 8.31 |
| 19 | Serine | 0 |
| 20 | Glycine | 0 |
| | Total | 100.00 |

Example 4: Formulations Lacking 3 Amino Acids

Formulations lacking three amino acids are prepared. Tables 14-17 show formulations lacking asparagine, glutamine, glutamic acid, or proline.

TABLE 14

Formulation—Asn-Gln-Glu

| | Amino acid | Percent of AA content |
|---|---|---|
| 1 | Histidine | 4.57 |
| 2 | Isoleucine | 4.57 |
| 3 | Leucine | 10.35 |
| 4 | Lysine | 7.88 |
| 5 | Methionine | 3.75 |
| 6 | Phenylalanine | 5.40 |
| 7 | Threonine | 5.40 |
| 8 | Tryptophan | 2.92 |
| 9 | Valine | 8.70 |
| 10 | Cysteine | 2.54 |
| 11 | Tyrosine | 2.54 |
| 12 | Glutamine | 0.00 |
| 13 | Arginine | 7.71 |
| 14 | Alanine | 6.03 |
| 15 | Aspartic Acid | 8.83 |
| 16 | Asparagine | 0.00 |
| 17 | Glutamic acid | 0.00 |
| 18 | Proline | 8.83 |
| 19 | Serine | 3.47 |
| 20 | Glycine | 6.50 |
| | Total | 100.00 |

TABLE 15

Formulation—Pro-Gln-Glu

| | Amino acid | Percent of AA content |
|---|---|---|
| 1 | Histidine | 4.78 |
| 2 | Isoleucine | 4.78 |
| 3 | Leucine | 10.77 |
| 4 | Lysine | 8.20 |
| 5 | Methionine | 3.93 |
| 6 | Phenylalanine | 5.64 |
| 7 | Threonine | 5.64 |
| 8 | Tryptophan | 3.07 |
| 9 | Valine | 9.06 |
| 10 | Cysteine | 2.64 |
| 11 | Tyrosine | 2.64 |
| 12 | Glutamine | 0.00 |
| 13 | Arginine | 7.89 |
| 14 | Alanine | 6.19 |
| 15 | Aspartic Acid | 9.03 |
| 16 | Asparagine | 5.48 |
| 17 | Glutamic acid | 0.00 |
| 18 | Proline | 0.00 |
| 19 | Serine | 3.59 |
| 20 | Glycine | 6.66 |
| | Total | 100.00 |

TABLE 16

Formulation lacking proline, serine, and glycine.

| | Amino acid | Percent of AA content |
|---|---|---|
| 1 | Histidine | 4.0 |
| 2 | Isoleucine | 4.0 |
| 3 | Leucine | 9.3 |
| 4 | Lysine | 7.0 |
| 5 | Methionine | 3.2 |
| 6 | Phenylalanine | 4.7 |
| 7 | Threonine | 4.7 |
| 8 | Tryptophan | 2.4 |
| 9 | Valine | 7.8 |
| 10 | Cysteine | 2.3 |
| 11 | Tyrosine | 2.3 |
| 12 | Glutamine | 9.4 |
| 13 | Arginine | 7.6 |
| 14 | Alanine | 5.9 |
| 15 | Aspartic Acid | 8.7 |
| 16 | Asparagine | 5.2 |
| 17 | Glutamic acid | 11.6 |
| 18 | Proline | 0.0 |
| 19 | Serine | 0.0 |
| 20 | Glycine | 0.0 |
| | Total | 100.00 |

Potassium and magnesium-supplemented formulations lacking serine, glycine, and proline were prepared. The contents each formulation are shown in Tables 17-22. Table 17 shows a potassium and magnesium-supplemented formulation lacking proline, serine, and glycine. Table 18 shows a potassium and magnesium-supplemented formulation lacking proline, serine, and glycine. Table 19 shows a potassium and magnesium-supplemented formulation lacking proline, serine, and glycine. Table 20 shows a potassium and magnesium-supplemented formulation lacking proline, serine, and glycine. Table 21 shows a formulation lacking cysteine, serine, and glycine. Table 22 shows a potassium and magnesium-supplemented formulation lacking serine, glycine, and cysteine.

TABLE 17

Formulation—Pro-Ser-Gly

| | Amino acid | Milligrams (mg) | % of composition (w/w) | % of AA content (w/w) |
|---|---|---|---|---|
| 1 | L-Histidine HCl | 550.00 | 5 | 5.2 |
| 2 | L-Isoleucine | 600.00 | 5.5 | 5.7 |
| 3 | L-Leucine | 1,150.00 | 10.5 | 11 |
| 4 | L-Lysine HCl | 1,100.00 | 10 | 10.5 |
| 5 | L-Methionine | 300.00 | 2.7 | 2.9 |
| 6 | L-Phenylalanine | 750.00 | 6.8 | 7.2 |
| 7 | L-Threonine | 600.00 | 5.5 | 5.7 |
| 8 | L-Tryptophan | 220.00 | 2 | 2.1 |
| 9 | L-Valine | 600.00 | 5.5 | 5.7 |
| 10 | L-Cysteine HCl | 180.00 | 1.6 | 1.7 |
| 11 | L-Tyrosine | 330.00 | 3 | 3.1 |
| 12 | L-Glutamine | 300.00 | 2.7 | 2.9 |
| 13 | L-Arginine Base | 950.00 | 8.6 | 9.1 |
| 14 | L-Alanine | 600.00 | 5.5 | 5.7 |
| 15 | L-Aspartic Acid | 1,000.00 | 9.1 | 9.5 |
| 16 | L-Asparagine Hydrate | 600.00 | 5.5 | 5.7 |
| 17 | L-Glutamic Acid | 600.00 | 5.5 | 5.7 |
| 18 | L-Serine | 0.00 | 0 | 0 |
| 19 | Glycine | 0.00 | 0 | 0 |
| 20 | L-Proline | 0.00 | 0 | 0 |
| 21 | Taurine | 50.00 | 0.5 | 0.5 |
| | Total Amino Acids | 10,480.00 | 95.3 | 100 |
| | Other Materials | | | |
| 22 | Potassium Chloride (KCl) | 318.00 | 2.9 | — |

TABLE 17-continued

Formulation—Pro-Ser-Gly

| | Amino acid | Milligrams (mg) | % of composition (w/w) | % of AA content (w/w) |
|---|---|---|---|---|
| 23 | Magnesium Citrate ($C_6H_6MgO_7$) | 203.00 | 1.8 | — |
| 24 | D-Glucose | 0.00 | 0 | — |
| | Total Materials | 11,001.00 | 100 | — |

TABLE 18

Formulation -Pro -Ser -Gly

| | Amino Acid | Milligrams (mg) | % of composition (w/w) | % of AA content (w/w) |
|---|---|---|---|---|
| 1 | L-Histidine | 445.00 | 4.3 | 4.5 |
| 2 | L-Isoleucine | 600.00 | 5.8 | 6.1 |
| 3 | L-Leucine | 1,150.00 | 11 | 11.7 |
| 4 | L-Lysine HCl | 1,100.00 | 10.5 | 11.2 |
| 5 | L-Methionine | 300.00 | 2.9 | 3 |
| 6 | L-Phenylalanine | 750.00 | 7.2 | 7.6 |
| 7 | L-Threonine | 600.00 | 5.8 | 6.1 |
| 8 | L-Tryptophan | 220.00 | 2.1 | 2.2 |
| 9 | L-Valine | 600.00 | 5.8 | 6.1 |
| 10 | L-Cystine | 138.00 | 1.3 | 1.4 |
| 11 | L-Tyrosine | 330.00 | 3.2 | 3.4 |
| 12 | L-Glutamine | 300.00 | 2.9 | 3 |
| 13 | L-Arginine Base | 950.00 | 9.1 | 9.7 |
| 14 | L-Alanine | 600.00 | 5.8 | 6.1 |
| 15 | L-Aspartic Acid | 508.70 | 4.9 | 5.2 |
| 16 | L-Asparagine Hydrate | 600.00 | 5.8 | 6.1 |
| 17 | L-Glutamic Acid | 600.00 | 5.8 | 6.1 |
| 18 | L-Serine | 0.00 | 0 | 0 |
| 19 | Glycine | 0.00 | 0 | 0 |
| 20 | L-Proline | 0.00 | 0 | 0 |
| 21 | Taurine | 50.00 | 0.5 | 0.5 |
| | Total Amino Acids | | 94.3 | 100.0 |
| | Other Materials | | | |
| 22 | Potassium Chloride (KCl) | 380.00 | 3.6 | — |
| 23 | Magnesium Citrate ($C_6H_6MgO_7$) | 211.00 | 2 | — |
| 24 | D-Glucose | 0.00 | 0 | — |
| | Total Materials | | 100 | — |

TABLE 19

Formulation -Pro -Ser -Gly

| | Amino Acid | Milligrams (mg) | % of composition (w/w) | % of AA content (w/w) |
|---|---|---|---|---|
| 1 | L-Histidine | 445.00 | 4.3 | 4.6 |
| 2 | L-Isoleucine | 600.00 | 5.8 | 6.2 |
| 3 | L-Leucine | 1,150.00 | 11.1 | 11.8 |
| 4 | L-Lysine Monohydrate | 995.00 | 9.6 | 10.2 |
| 5 | L-Methionine | 300.00 | 2.9 | 3.1 |
| 6 | L-Phenylalanine | 750.00 | 7.3 | 7.7 |
| 7 | L-Threonine | 600.00 | 5.8 | 6.2 |
| 8 | L-Tryptophan | 220.00 | 2.1 | 2.3 |
| 9 | L-Valine | 600.00 | 5.8 | 6.2 |
| 10 | L-Cystine | 138.00 | 1.3 | 1.4 |
| 11 | L-Tyrosine | 330.00 | 3.2 | 3.4 |
| 12 | L-Glutamine | 300.00 | 2.9 | 3.1 |
| 13 | L-Arginine Base | 246.00 | 2.4 | 2.5 |
| 14 | L-Alanine | 600.00 | 5.8 | 6.2 |
| 15 | L-Aspartic Acid | 508.70 | 4.9 | 5.2 |
| 16 | L-Asparagine Hydrate | 600.00 | 5.8 | 6.2 |
| 17 | L-Arginine-L-Glutamate Salt | 1,300.00 | 12.6 | 13.4 |
| 18 | L-Serine | 0.00 | 0 | 0 |
| 19 | Glycine | 0.00 | 0 | 0 |
| 20 | L-Proline | 0.00 | 0 | 0 |
| 21 | Taurine | 50.00 | 0.5 | 0.5 |
| | Total Amino Acids | 9,732.70 | 94.3 | 100 |
| | Other Materials | | | — |
| 22 | Potassium Chloride (KCl) | 380.00 | 3.7 | — |
| 23 | Magnesium Citrate ($C_6H_6Mg_o7$) | 211.00 | 2 | — |
| 24 | D-Glucose | 0.00 | 0 | — |
| | Total Materials | 10,323.70 | 100 | — |

TABLE 20

Formulation -Pro -Ser -Gly

| | Amino acid | Milligrams (mg) | % of composition (w/w) | % of AA content (w/w) |
|---|---|---|---|---|
| 1 | L-Histidine | 445.00 | 4.3 | 4.6 |
| 2 | L-Isoleucine | 600.00 | 5.8 | 6.2 |
| 3 | L-Leucine | 1,150.00 | 11.1 | 11.8 |
| 4 | L-Lysine Monohydrate | 995.00 | 9.6 | 10.2 |
| 5 | L-Methionine | 300.00 | 2.9 | 3.1 |
| 6 | L-Phenylalanine | 750.00 | 7.3 | 7.7 |
| 7 | L-Threonine | 600.00 | 5.8 | 6.2 |
| 8 | L-Tryptophan | 220.00 | 2.1 | 2.3 |
| 9 | L-Valine | 600.00 | 5.8 | 6.2 |
| 10 | L-Cystine | 138.00 | 1.3 | 1.4 |
| 11 | L-Tyrosine | 330.00 | 3.2 | 3.4 |
| 12 | L-Glutamine | 300.00 | 2.9 | 3.1 |
| 13 | L-Arginine Base | 246.00 | 2.4 | 2.5 |
| 14 | L-Alanine | 600.00 | 5.8 | 6.2 |
| 15 | L-Aspartic Acid | 508.70 | 4.9 | 5.2 |
| 16 | L-Asparagine Hydrate | 600.00 | 5.8 | 6.2 |
| 17 | L-Arginine-L-Glutamate Salt | 1,300.00 | 12.6 | 13.4 |
| 18 | L-Serine | 0.00 | 0 | 0 |
| 19 | Glycine | 0.00 | 0 | 0 |
| 20 | L-Proline | 0.00 | 0 | 0 |
| 21 | Taurine | 50.00 | 0.5 | 0.5 |
| | Total Amino Acids | 9,732.70 | 94.3 | 100 |
| | Other Materials | | — | — |
| 22 | L-Aspartic Acid Potassium Salt | 380.00 | 3.7 | — |
| 23 | L-Aspartic Acid Magnesium Salt | 211.00 | 2 | — |
| 24 | D-Glucose | 0.00 | 0 | — |
| | Total Materials | 10,323.70 | 100 | — |

TABLE 21

Formulation -Cys -Ser -Gly

|  | Amino acid | Percent of AA content |
|---|---|---|
| 1 | Histidine | 3.6 |
| 2 | Isoleucine | 3.6 |
| 3 | Leucine | 8.5 |
| 4 | Lysine | 6.4 |
| 5 | Methionine | 2.9 |
| 6 | Phenylalanine | 4.3 |
| 7 | Threonine | 4.3 |
| 8 | Tryptophan | 2.2 |
| 9 | Valine | 7.1 |
| 10 | Cysteine | 0.0 |
| 11 | Tyrosine | 2.1 |
| 12 | Glutamine | 9.1 |
| 13 | Arginine | 7.3 |
| 14 | Alanine | 5.6 |
| 15 | Aspartic Acid | 8.4 |
| 16 | Asparagine | 4.9 |
| 17 | Glutamic acid | 11.2 |
| 18 | Proline | 8.4 |
| 19 | Serine | 0.0 |
| 20 | Glycine | 0.0 |
|  | Total | 100.00 |

TABLE 22

Formulation -Cys -Ser -Gly

|  | Amino acid | Milligrams (mg) | % of composition (w/w) | % of AA content (w/w) |
|---|---|---|---|---|
| 1 | L-Histidine | 445.00 | 4.3 | 4.6 |
| 2 | L-Isoleucine | 600.00 | 5.8 | 6.2 |
| 3 | L-Leucine | 1,150.00 | 11.1 | 11.8 |
| 4 | L-Lysine Monohydrate | 995.00 | 9.6 | 10.2 |
| 5 | L-Methionine | 300.00 | 2.9 | 3.1 |
| 6 | L-Phenylalanine | 750.00 | 7.3 | 7.7 |
| 7 | L-Threonine | 600.00 | 5.8 | 6.2 |
| 8 | L-Tryptophan | 220.00 | 2.1 | 2.3 |
| 9 | L-Valine | 600.00 | 5.8 | 6.2 |
| 10 | L-Cystine | 0 | 0 | 0 |
| 11 | L-Tyrosine | 330.00 | 3.2 | 3.4 |
| 12 | L-Glutamine | 300.00 | 2.9 | 3.1 |
| 13 | L-Arginine Base | 246.00 | 2.4 | 2.5 |
| 14 | L-Alanine | 600.00 | 5.8 | 6.2 |
| 15 | L-Aspartic Acid | 508.70 | 4.9 | 5.2 |
| 16 | L-Asparagine Hydrate | 600.00 | 5.8 | 6.2 |
| 17 | L-Arginine-L-Glutamate Salt | 1,300.00 | 12.6 | 13.4 |
| 18 | L-Serine | 0.00 | 0 | 0 |
| 19 | Glycine | 0.00 | 0 | 0 |
| 20 | L-Proline | 1,000 | 9.7 | 10.3 |
| 21 | Taurine | 50.00 | 0.5 | 0.5 |
|  | Total amino acids | 9,732.70 | 94.3 | 100 |
|  | Other Materials |  |  |  |
| 22 | L-Aspartic Acid Potassium Salt | 380.00 | 3.7 |  |
| 23 | L-Aspartic Acid Magnesium Salt | 211.00 | 2.0 |  |
| 24 | D-Glucose | 0.00 | 0 |  |
|  | Total Materials | 10,323.70 | 100.0 | — |

Example 5: Amino Acid Formulations Lacking at Least 4 Amino Acids

Formulations lacking four amino acids are prepared. Table 23 shows a formulation lacking glutamine, glutamic acid, serine, and glycine. Table 24 shows a formulation lacking cysteine, proline, serine, and glycine.

TABLE 23

Formulation -Gln -Glu -Ser -Gly

|  | Amino acid | Percent of AA content |
|---|---|---|
| 1 | Histidine | 4.73 |
| 2 | Isoleucine | 4.73 |
| 3 | Leucine | 10.76 |
| 4 | Lysine | 8.18 |
| 5 | Methionine | 3.87 |
| 6 | Phenylalanine | 5.59 |
| 7 | Threonine | 5.59 |
| 8 | Tryptophan | 3.00 |
| 9 | Valine | 9.04 |
| 10 | Cysteine | 2.67 |
| 11 | Tyrosine | 2.67 |
| 12 | Glutamine | 0.00 |
| 13 | Arginine | 8.22 |
| 14 | Alanine | 6.42 |
| 15 | Aspartic Acid | 9.42 |
| 16 | Asparagine | 5.67 |
| 17 | Glutamic acid | 0.00 |
| 18 | Proline | 9.42 |
| 19 | Serine | 0.00 |
| 20 | Glycine | 0.00 |
|  | Total | 100.00 |

TABLE 24

Formulation -Cys -Pro -Ser -Gly

|  | Amino acid | Percent of AA content |
|---|---|---|
| 1 | Histidine | 4.1 |
| 2 | Isoleucine | 4.1 |
| 3 | Leucine | 9.5 |
| 4 | Lysine | 7.2 |
| 5 | Methionine | 3.3 |
| 6 | Phenylalanine | 4.9 |
| 7 | Threonine | 4.9 |
| 8 | Tryptophan | 2.5 |
| 9 | Valine | 8.0 |
| 10 | Cysteine | 0.0 |
| 11 | Tyrosine | 2.4 |
| 12 | Glutamine | 9.6 |
| 13 | Arginine | 7.7 |
| 14 | Alanine | 6.0 |
| 15 | Aspartic Acid | 8.8 |
| 16 | Asparagine | 5.3 |
| 17 | Glutamic acid | 11.7 |
| 18 | Proline | 0.0 |
| 19 | Serine | 0.0 |
| 20 | Glycine | 0.0 |
|  | Total | 100.00 |

Example 6: Amino Acid Formulations Lacking 5 Amino Acids

Formulations lacking five amino acids are prepared. Table 25-Table 27 show formulations lacking cysteine, glutamine, glutamic acid, serine, glycine, proline, or tyrosine.

TABLE 25

Formulation lacking cysteine, glutamine, glutamic acid, serine, and glycine.

| | Amino acid | Percent of AA content |
|---|---|---|
| 1 | Histidine | 4.90 |
| 2 | Isoleucine | 4.90 |
| 3 | Leucine | 11.07 |
| 4 | Lysine | 8.42 |
| 5 | Methionine | 4.02 |
| 6 | Phenylalanine | 5.78 |
| 7 | Threonine | 5.78 |
| 8 | Tryptophan | 3.14 |
| 9 | Valine | 9.31 |
| 10 | Cysteine | 0.00 |
| 11 | Tyrosine | 2.77 |
| 12 | Glutamine | 0.00 |
| 13 | Arginine | 8.38 |
| 14 | Alanine | 6.56 |
| 15 | Aspartic Acid | 9.59 |
| 16 | Asparagine | 5.80 |
| 17 | Glutamic acid | 0.00 |
| 18 | Proline | 9.59 |
| 19 | Serine | 0.00 |
| 20 | Glycine | 0.00 |
| | Total | 100.00 |

TABLE 26

Formulation lacking glutamine, glutamic acid, proline, serine, and glycine.

| | Amino acid | Percent of AA content |
|---|---|---|
| 1 | Histidine | 5.34 |
| 2 | Isoleucine | 5.34 |
| 3 | Leucine | 11.93 |
| 4 | Lysine | 9.11 |
| 5 | Methionine | 4.40 |
| 6 | Phenylalanine | 6.28 |
| 7 | Threonine | 6.28 |
| 8 | Tryptophan | 3.46 |
| 9 | Valine | 10.05 |
| 10 | Cysteine | 2.98 |
| 11 | Tyrosine | 2.98 |
| 12 | Glutamine | 0.00 |
| 13 | Arginine | 8.79 |
| 14 | Alanine | 6.90 |
| 15 | Aspartic Acid | 10.04 |
| 16 | Asparagine | 6.12 |
| 17 | Glutamic acid | 0.00 |
| 18 | Proline | 0.00 |
| 19 | Serine | 0.00 |
| 20 | Glycine | 0.00 |
| | Total | 100.00 |

TABLE 27

Formulation lacking cysteine, proline, tyrosine, serine, and glycine.

| | Amino acid | Percent of AA content |
|---|---|---|
| 1 | Histidine | 4.3 |
| 2 | Isoleucine | 4.3 |
| 3 | Leucine | 9.8 |
| 4 | Lysine | 7.4 |
| 5 | Methionine | 3.5 |
| 6 | Phenylalanine | 5.0 |
| 7 | Threonine | 5.0 |
| 8 | Tryptophan | 2.7 |
| 9 | Valine | 8.2 |
| 10 | Cysteine | 0.0 |
| 11 | Tyrosine | 0.0 |
| 12 | Glutamine | 9.7 |
| 13 | Arginine | 7.8 |
| 14 | Alanine | 6.1 |
| 15 | Aspartic Acid | 9.0 |
| 16 | Asparagine | 5.4 |
| 17 | Glutamic acid | 11.9 |
| 18 | Proline | 0.0 |
| 19 | Serine | 0.0 |
| 20 | Glycine | 0.0 |
| | Total | 100.00 |

Example 7: Amino Acid Formulations Lacking 6 Amino Acids

Formulations lacking six amino acids are prepared. Table 28 and Table 29 show formulations lacking cysteine, glutamine, glutamic acid, proline, serine, glycine, and tyrosine.

TABLE 28

Formulation lacking cysteine, glutamine, glutamic acid, proline, serine, and glycine.

| | Amino acid | Percent of AA content |
|---|---|---|
| 1 | Histidine | 5.54 |
| 2 | Isoleucine | 5.54 |
| 3 | Leucine | 12.28 |
| 4 | Lysine | 9.39 |
| 5 | Methionine | 4.58 |
| 6 | Phenylalanine | 6.50 |
| 7 | Threonine | 6.50 |
| 8 | Tryptophan | 3.61 |
| 9 | Valine | 10.36 |
| 10 | Cysteine | 0.00 |
| 11 | Tyrosine | 3.11 |
| 12 | Glutamine | 0.00 |
| 13 | Arginine | 8.98 |
| 14 | Alanine | 7.07 |
| 15 | Aspartic Acid | 10.25 |
| 16 | Asparagine | 6.28 |
| 17 | Glutamic acid | 0.00 |
| 18 | Proline | 0.00 |
| 19 | Serine | 0.00 |
| 20 | Glycine | 0.00 |
| | Total | 100.00 |

TABLE 29

Formulation lacking cysteine, tyrosine, glutamic acid, proline, serine, and glycine.

| | Amino acid | Percent of AA content |
|---|---|---|
| 1 | Histidine | 5.0 |
| 2 | Isoleucine | 5.0 |
| 3 | Leucine | 11.3 |
| 4 | Lysine | 8.6 |
| 5 | Methionine | 4.1 |
| 6 | Phenylalanine | 5.9 |
| 7 | Threonine | 5.9 |
| 8 | Tryptophan | 3.2 |
| 9 | Valine | 9.5 |
| 10 | Cysteine | 0.0 |
| 11 | Tyrosine | 0.0 |
| 12 | Glutamine | 10.5 |
| 13 | Arginine | 8.5 |
| 14 | Alanine | 6.7 |

TABLE 29-continued

Formulation lacking cysteine, tyrosine, glutamic acid, proline, serine, and glycine.

| | Amino acid | Percent of AA content |
|---|---|---|
| 15 | Aspartic Acid | 9.7 |
| 16 | Asparagine | 5.9 |
| 17 | Glutamic acid | 0.0 |
| 18 | Proline | 0.0 |
| 19 | Serine | 0.0 |
| 20 | Glycine | 0.0 |
| | Total | 100.00 |

Example 8: Amino Acid Formulation Lacking 7 Amino Acids

Formulations lacking seven amino acids are prepared. Table 30 and Table 31 show formulations lacking alanine, aspartic acid, asparagine, glutamic acid, proline, serine, glycine, or tyrosine.

TABLE 30

Formulation lacking alanine, aspartic acid, asparagine, glutamic acid, proline, serine and glycine.

| | Amino acid | Percent of AA content |
|---|---|---|
| 1 | Histidine | 6.6 |
| 2 | Isoleucine | 6.6 |
| 3 | Leucine | 13.4 |
| 4 | Lysine | 10.5 |
| 5 | Methionine | 5.6 |
| 6 | Phenylalanine | 7.6 |
| 7 | Threonine | 7.6 |
| 8 | Tryptophan | 4.7 |
| 9 | Valine | 11.4 |
| 10 | Cysteine | 3.6 |
| 11 | Tyrosine | 3.6 |
| 12 | Glutamine | 10.4 |
| 13 | Arginine | 8.4 |
| 14 | Alanine | 0.0 |
| 15 | Aspartic Acid | 0.0 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

TABLE 31

Formulation lacking cysteine, tyrosine, asparagine, glutamic acid, proline, serine, and glycine.

| | Amino acid | Percent of AA content |
|---|---|---|
| 1 | Histidine | 5.4 |
| 2 | Isoleucine | 5.4 |
| 3 | Leucine | 12.0 |
| 4 | Lysine | 9.2 |
| 5 | Methionine | 4.5 |
| 6 | Phenylalanine | 6.4 |
| 7 | Threonine | 6.4 |
| 8 | Tryptophan | 3.6 |
| 9 | Valine | 10.1 |
| 10 | Cysteine | 0.0 |
| 11 | Tyrosine | 0.0 |
| 12 | Glutamine | 10.9 |
| 13 | Arginine | 8.9 |
| 14 | Alanine | 7.0 |
| 15 | Aspartic Acid | 10.1 |

TABLE 31-continued

Formulation lacking cysteine, tyrosine, asparagine, glutamic acid, proline, serine, and glycine.

| | Amino acid | Percent of AA content |
|---|---|---|
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

Example 9: Amino Acid Formulations Lacking 8 Amino Acids

A formulation lacking eight amino acids is prepared. Table 32 shows a formulation lacking cysteine, tyrosine, arginine, asparagine, glutamic acid, proline, serine, and glycine.

TABLE 32

Formulation lacking cysteine, tyrosine, arginine, asparagine, glutamic acid, proline, serine, and glycine.

| | Amino acid | Percent of AA content |
|---|---|---|
| 1 | Histidine | 6.1 |
| 2 | Isoleucine | 6.1 |
| 3 | Leucine | 13.2 |
| 4 | Lysine | 10.1 |
| 5 | Methionine | 5.1 |
| 6 | Phenylalanine | 7.1 |
| 7 | Threonine | 7.1 |
| 8 | Tryptophan | 4.0 |
| 9 | Valine | 11.2 |
| 10 | Cysteine | 0.0 |
| 11 | Tyrosine | 0.0 |
| 12 | Glutamine | 11.7 |
| 13 | Arginine | 0.0 |
| 14 | Alanine | 7.5 |
| 15 | Aspartic Acid | 10.8 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

Example 10: Amino Acid Formulations Lacking 9 Amino Acids

Formulations lacking nine amino acids are prepared. Table 33 and Table 34 show formulations lacking cysteine, tyrosine, glutamine, arginine, asparagine, glutamic acid, proline, serine, glycine, and tyrosine.

TABLE 33

Formulation lacking cysteine, tyrosine, glutamine, arginine, asparagine, glutamic acid, proline, serine, and glycine.

| | Amino acid | Percent of AA content |
|---|---|---|
| 1 | Histidine | 7.0 |
| 2 | Isoleucine | 7.0 |
| 3 | Leucine | 14.9 |
| 4 | Lysine | 11.5 |
| 5 | Methionine | 5.9 |

TABLE 33-continued

Formulation lacking cysteine, tyrosine, glutamine, arginine, asparagine, glutamic acid, proline, serine, and glycine.

| | Amino acid | Percent of AA content |
|---|---|---|
| 6 | Phenylalanine | 8.1 |
| 7 | Threonine | 8.1 |
| 8 | Tryptophan | 4.7 |
| 9 | Valine | 12.6 |
| 10 | Cysteine | 0.0 |
| 11 | Tyrosine | 0.0 |
| 12 | Glutamine | 0.0 |
| 13 | Arginine | 0.0 |
| 14 | Alanine | 8.4 |
| 15 | Aspartic Acid | 11.9 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

TABLE 34

Formulation lacking cysteine, tyrosine, alanine, arginine, asparagine, aspartic acid, proline, serine, and glycine.

| | Amino acid | Percent of AA content |
|---|---|---|
| 1 | Histidine | 6.4 |
| 2 | Isoleucine | 6.4 |
| 3 | Leucine | 13.8 |
| 4 | Lysine | 10.6 |
| 5 | Methionine | 5.4 |
| 6 | Phenylalanine | 7.5 |
| 7 | Threonine | 7.5 |
| 8 | Tryptophan | 4.3 |
| 9 | Valine | 11.7 |
| 10 | Cysteine | 0.0 |
| 11 | Tyrosine | 0.0 |
| 12 | Glutamine | 12.0 |
| 13 | Arginine | 0.0 |
| 14 | Alanine | 0.0 |
| 15 | Aspartic acid | 0.0 |
| 16 | Asparagine | 0.0 |
| 17 | Glutamic acid | 14.5 |
| 18 | Proline | 0.0 |
| 19 | Serine | 0.0 |
| 20 | Glycine | 0.0 |
| | Total | 100.00 |

Example 11: Amino Acid Formulations Lacking 10 Amino Acids

Formulations lacking ten amino acids are prepared. Tables 35-38 show formulations lacking cysteine, tyrosine, glutamine, arginine, alanine, aspartic acid, arginine, glutamic acid, proline, serine, or glycine. The formulations lacking 10 amino acids contain one non-essential amino acid.

TABLE 35

Formulation lacking cysteine, tyrosine, glutamine, arginine, alanine, asparagine, glutamic acid, proline, serine, and glycine.

| | Amino acid | Percent of AA content |
|---|---|---|
| 1 | Histidine | 7.7 |
| 2 | Isoleucine | 7.7 |
| 3 | Leucine | 16.1 |
| 4 | Lysine | 12.5 |

TABLE 35-continued

Formulation lacking cysteine, tyrosine, glutamine, arginine, alanine, asparagine, glutamic acid, proline, serine, and glycine.

| | Amino acid | Percent of AA content |
|---|---|---|
| 5 | Methionine | 6.5 |
| 6 | Phenylalanine | 8.9 |
| 7 | Threonine | 8.9 |
| 8 | Tryptophan | 5.3 |
| 9 | Valine | 13.7 |
| 10 | Cysteine | 0.0 |
| 11 | Tyrosine | 0.0 |
| 12 | Glutamine | 0.0 |
| 13 | Arginine | 0.0 |
| 14 | Alanine | 0.0 |
| 15 | Aspartic acid | 12.8 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

TABLE 36

Formulation lacking cysteine, tyrosine, arginine, alanine, aspartic acid, asparagine, glutamic acid, proline, serine, and glycine.

| | Amino acid | Percent of AA content |
|---|---|---|
| 1 | Histidine | 7.6 |
| 2 | Isoleucine | 7.6 |
| 3 | Leucine | 16.0 |
| 4 | Lysine | 12.4 |
| 5 | Methionine | 6.4 |
| 6 | Phenylalanine | 8.8 |
| 7 | Threonine | 8.8 |
| 8 | Tryptophan | 5.2 |
| 9 | Valine | 13.6 |
| 10 | Cysteine | 0.0 |
| 11 | Tyrosine | 0.0 |
| 12 | Glutamine | 13.6 |
| 13 | Arginine | 0.0 |
| 14 | Alanine | 0.0 |
| 15 | Aspartic acid | 0.0 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

TABLE 37

Formulation lacking cysteine, tyrosine, glutamine, arginine, alanine, aspartic acid, asparagine, proline, serine, and glycine.

| | Amino acid | Percent of AA content |
|---|---|---|
| 1 | Histidine | 7.4 |
| 2 | Isoleucine | 7.4 |
| 3 | Leucine | 15.5 |
| 4 | Lysine | 12.0 |
| 5 | Methionine | 6.2 |
| 6 | Phenylalanine | 8.6 |
| 7 | Threonine | 8.6 |
| 8 | Tryptophan | 5.1 |
| 9 | Valine | 13.2 |
| 10 | Cysteine | 0.0 |
| 11 | Tyrosine | 0.0 |
| 12 | Glutamine | 0.0 |
| 13 | Arginine | 0.0 |
| 14 | Alanine | 0.0 |

TABLE 37-continued

Formulation lacking cysteine, tyrosine, glutamine, arginine, alanine, aspartic acid, asparagine, proline, serine, and glycine.

| | Amino acid | Percent of AA content |
|---|---|---|
| 15 | Aspartic Acid | 0.0 |
| 16 | Asparagine | 0.0 |
| 17 | Glutamic acid | 16.0 |
| 18 | Proline | 0.0 |
| 19 | Serine | 0.0 |
| 20 | Glycine | 0.0 |
| | Total | 100.00 |

TABLE 38

Formulation lacking cysteine, tyrosine, glutamine, arginine, aspartic acid, asparagine, glutamic acid, proline, serine, and glycine.

| | Amino acid | Percent of AA content |
|---|---|---|
| 1 | Histidine | 8.0 |
| 2 | Isoleucine | 8.0 |
| 3 | Leucine | 16.7 |
| 4 | Lysine | 13.0 |
| 5 | Methionine | 6.7 |
| 6 | Phenylalanine | 9.2 |
| 7 | Threonine | 9.2 |
| 8 | Tryptophan | 5.5 |
| 9 | Valine | 14.2 |
| 10 | Cysteine | 0.0 |
| 11 | Tyrosine | 0.0 |
| 12 | Glutamine | 0.0 |
| 13 | Arginine | 0.0 |
| 14 | Alanine | 9.4 |
| 15 | Aspartic acid | 0.0 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

Example 12: Amino Acid Formulations Lacking 11 Amino Acids

A formulation lacking eleven amino acids is prepared. Table 39 shows a formulation lacking cysteine, tyrosine, glutamine, arginine, alanine, aspartic acid, asparagine, glutamic acid, proline, serine and glycine. The formulation lacking 11 amino acids does not contain any non-essential amino acids.

TABLE 39

Formulation lacking all non-essential amino acids.

| | Amino acid | Percent of AA content |
|---|---|---|
| 1 | Histidine | 8.9 |
| 2 | Isoleucine | 8.9 |
| 3 | Leucine | 18.3 |
| 4 | Lysine | 14.2 |
| 5 | Methionine | 7.5 |
| 6 | Phenylalanine | 10.2 |
| 7 | Threonine | 10.2 |
| 8 | Tryptophan | 6.2 |
| 9 | Valine | 15.6 |
| 10 | Cysteine | 0.0 |
| 11 | Tyrosine | 0.0 |
| 12 | Glutamine | 0.0 |
| 13 | Arginine | 0.0 |

TABLE 39-continued

Formulation lacking all non-essential amino acids.

| | Amino acid | Percent of AA content |
|---|---|---|
| 14 | Alanine | 0.0 |
| 15 | Aspartic acid | 0.0 |
| 16 | Asparagine | 0.0 |
| 17 | Glutamic acid | 0.0 |
| 18 | Proline | 0.0 |
| 19 | Serine | 0.0 |
| 20 | Glycine | 0.0 |
| | Total | 100.00 |

Example 13: Nutritionally Complete Formulations

A nutritionally complete formulation is prepared in a carton containing 237 mL of the formula. Table 40 shows the ingredients in the nutritionally complete formulation.

TABLE 40

Nutritionally complete formulation

| Category | Ingredient | Amount per 1 carton (237 mL) |
|---|---|---|
| Amino acids (mg) | Histidine | 330 |
| | Isoleucine | 415 |
| | Leucine | 915 |
| | Lysine | 666 |
| | Methionine | 250 |
| | Cysteine | 165 |
| | Tyrosine | 165 |
| | Threonine | 415 |
| | Tryptophan | 165 |
| | Valine | 750 |
| | Alanine | 585 |
| | Aspartic Acid | 915 |
| | Asparagine | 500 |
| | Glutamic acid | 1250 |
| | Phenylalanine | 415 |
| | Serine | 0 |
| | Glycine | 0 |
| | Arginine | 666 |
| | Glutamine | 915 |
| | Proline | 833 |
| Carbohydrates (g) | Maltodextrin | 18 |
| | Sucrose | 16 |
| Lipids (g) | Coconut oil | 2 |
| | Flax Oil (ALA) | 2 |
| | Sunflower Oil (LA) | 8 |
| Fiber (Pre-biotic) (g) | Inulin | 5 |
| Vitamins/Co-factors | Vit A Palmitate (mcg) | 250 |
| | Beta Carotene (mcg) | 150 |
| | Vitamin C (mg) | 30 |
| | Calcium (mg) | 200 |
| | Iron (mg) | 4 |
| | Vitamin D (mcg) (2,3) | 4 |
| | Vitamin E (mg) (4) | 9 |
| | Vitamin K (mcg) | 20 |
| | Thiamin (mg) | 0.4 |
| | Riboflavin (mg) | 0.5 |
| | Niacin (mg) | 4 |
| | Vitamin B6 (mg) | 0.6 |
| | Folate (DFE) (mcg) (5) | 100 |
| | Vitamin B12 (mcg) | 2 |
| | Biotin (mcg) | 7 |
| | Pantothenic Acid (mg) | 3 |
| | Choline (mg) | 110 |
| | Carnitine (mg) | 415 |

TABLE 40-continued

Nutritionally complete formulation

| Category | Ingredient | Amount per 1 carton (237 mL) |
|---|---|---|
| Minerals | Phosphorus (mg) | 100 |
| | Iodine (mcg) | 40 |
| | Magnesium (mg) | 80 |
| | Zinc (mg) | 3 |
| | Selenium (mcg) | 11 |
| | Copper (mg) | 0.5 |
| | Manganese (mg) | 0.4 |
| | Chromium (mcg) | 8 |
| | Molybdenum (mcg) | 9 |
| | Chloride (mg) | 400 |
| Water | | 76% |

Example 14: Administration of a Composition Disclosed Herein

A 60 kg subject with cancer is allotted a target daily protein intake of 0.8 g/kg/day, or 48 g/day. The subject is prescribed four sachets (12 g each) containing formulation A per day. The subject mixes the sachets into a glass of water and optionally adds a flavorant drop, such as a concentrated fruit flavor drink. The subject drinks the mixture of the composition. FIG. 1 illustrates adding a composition contained in a sachet (101) with a glass of water (102); and a subject (104) drinking the mixture of the composition prepared in water (103).

The subject's consumption of other foods and beverages throughout the day is monitored. The subject is prescribed a detailed diet to closely control daily protein intake. The diet consists of pre-made meals and snacks that are low in protein and low in the amino acids that are excluded from the composition. Amino acid levels of the subject are measured in biological samples obtained from the subject using analytical methods, including liquid chromatography or liquid chromatography-mass spectrometry.

Example 15: Treatment of a Condition

A subject with a disease, for example, cancer comes to a medical professional for treatment. The medical professional prescribes Formulation B. Formulation B is prescribed as several sachets. The subject mixes the sachets into a glass of water and optionally adds a flavorant drop, such as MiO flavorant drops. The subject drinks the mixture of the composition. FIG. 1 illustrates adding a composition contained in a sachet (101) with a glass of water (102); and a subject (104) drinking the mixture of the composition prepared in water (103). A sample is taken from the subject to monitor the nutrient and amino acid levels in the subject. Based on the sample, a different Formulation disclosed herein in prescribed or the amount of Formulation B is adjusted.

Example 16: Study to Evaluate a Composition Disclosed Herein for Treating a Disease in a Subject A study is performed to assess the effect of a composition disclosed herein on treating a condition in a subject. Twenty subjects with cancer are entered into a double-blind, placebo controlled and randomized study. The experimental group includes ten subjects who are given the formulation of Table 6 as sachets. Parameters observed are nutrient and amino acid levels in the subject before and after administration of the Formulation. The control group includes ten subjects who are given sachets of a powdered placebo. The placebo is taken at the same time as the experimental group takes the formulation of Table 6. Parameters observed are nutrient and amino acid levels in the subject before and after administration of the placebo. Following treatment, subjects in the experimental group have a reduction in tumor cell proliferation or tumor cell volume as compared with the control group.

Example 17: Study of Amino Acid Levels in Healthy Subject Administered Amino Acid Formulation Lacking Proline Three healthy human subjects between 18-60 years old with a body mass index (BMI) between 18 and 30 that habitually consume a Western diet were allowed to consume their habitual diet (i.e., diet typical of the subject before administration of composition) for one day to establish a baseline level of serum amino acids. A Western diet can be a diet that has a daily calorie intake from about 50% from carbohydrates, about 15% from protein, and about 35% from fats.

Subjects that met the following criteria were not allowed to participate in the study: (i) subjects who had any clinically relevant history or the presence of disease (i.e., respiratory, renal, hepatic, gastrointestinal, hematological, lymphatic, neurological, cardiovascular, psychiatric, etc.); (ii) subjects who had a history of disease or illness or use a medication that specifically alters proline; (iii) subjects who had a history of fainting or becoming nauseous at the sight of needles, blood, or when giving blood; (iv) subjects who were or had been recently ill, such as subjects that recently experienced fever and/or gastrointestinal distress including vomiting and/or diarrhea; (v) subjects that were unwilling or unlikely to adhere to diet that is low in protein and lacks meat and dairy (milk, cheese) during the course of the study; (vi) subjects that habitually consumed a diet that restricts a food group (e.g. Carbohydrate, as with the ketogenic diet) or a specific ingredient (e.g. gluten); (vii) subjects that had known food allergies to dairy, wheat, nuts, or sucralose; (vii) subjects that used tobacco or nicotine in any form at the time of recruitment; (ix) subjects that consumed caffeine greater than 500 mg per day (e.g., daily intake >4 tall cups of coffee, >5 cups of tea, or >8 soft drinks); (x) subjects that were unwilling to discontinue consumption of coffee with cow's milk during the study (coffee without milk (with/without sugar or sucralose) was allowed, or coffee with coconut milk (no other forms of creamer) was allowed; (xi) subjects that were unwilling to discontinue consumption of alcohol during the study; (xii) subjects that normally exercise for >2 hours per day or engage in highly intense, strenuous, or otherwise extreme exercise; (xiii) subjects that were unwilling to adjust exercise habits to 1) less than 60 min per day for each day of study participation, and 2) only exercise after the afternoon post-prandial blood draw (i.e., no exercise before lunch time); (xiv) subjects that did not speak fluent English (due to lack of an available translator during the COVID-19 pandemic); and (xv) subjects that had participated in a clinical trial/experimental study in the past 14 days.

Each of the subjects was then fed a 1613 kcal/day low protein whole food diet for five days. The diet consisted of 9 g of protein/day and ~350 mg proline/day. 50%, 2%, and 48% of the daily caloric content was derived from carbohydrates, protein, and fat, respectively. Throughout the five day period, the diet was administered in conjunction with doses of a supplemental amino acid formulation in sachet form. Each sachet contained the components listed in Table 41. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for amino acid content via LC-MS.

Figure 2:
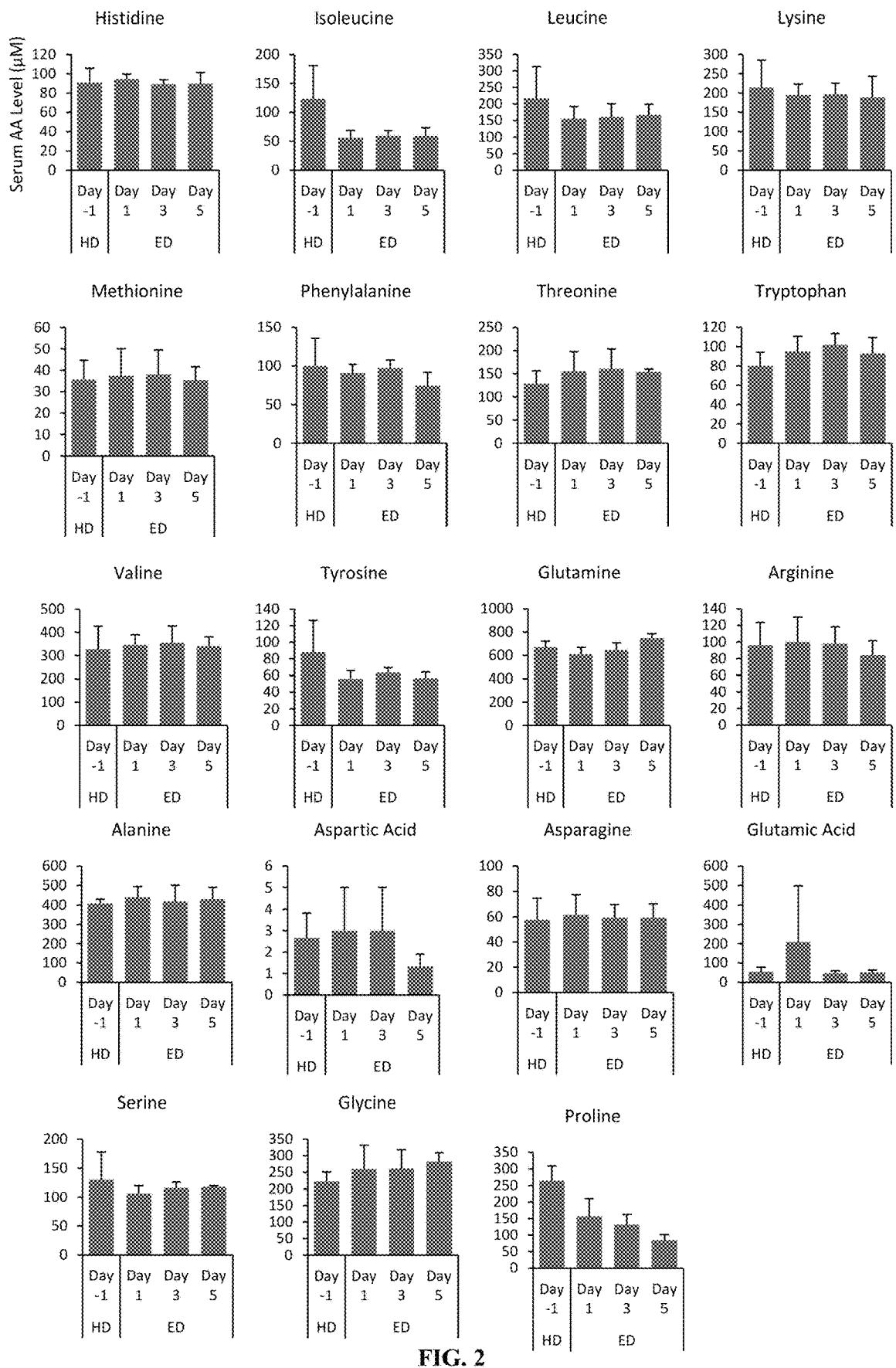
FIG. 2 provides charts illustrating serum levels of amino acids in subjects before and after administration of a diet deficient in proline as described in Example 17.
Figure 5:
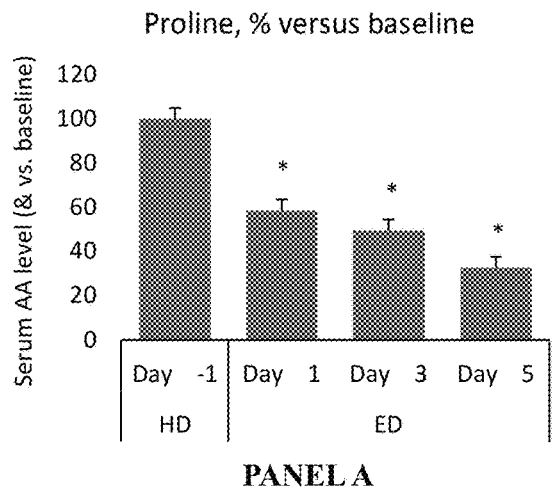
FIG. 5 provides charts illustrating serum levels of proline as a percentage of pre-diet baseline levels in subjects administered proline-deficient diets described in EXAMPLES 17 (PANEL A), 18 (PANEL B), and 19 (PANEL C).
Figure 5:
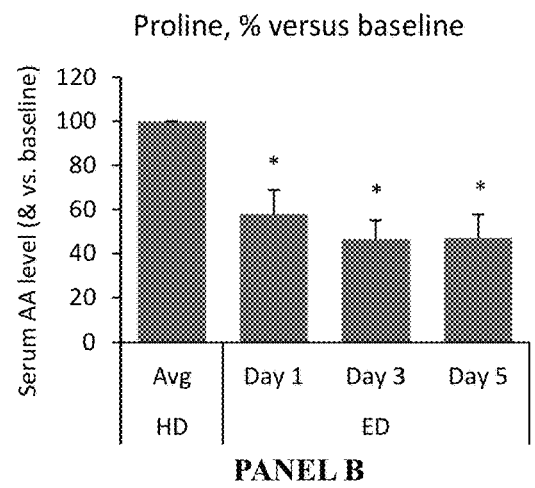
Figure 5:
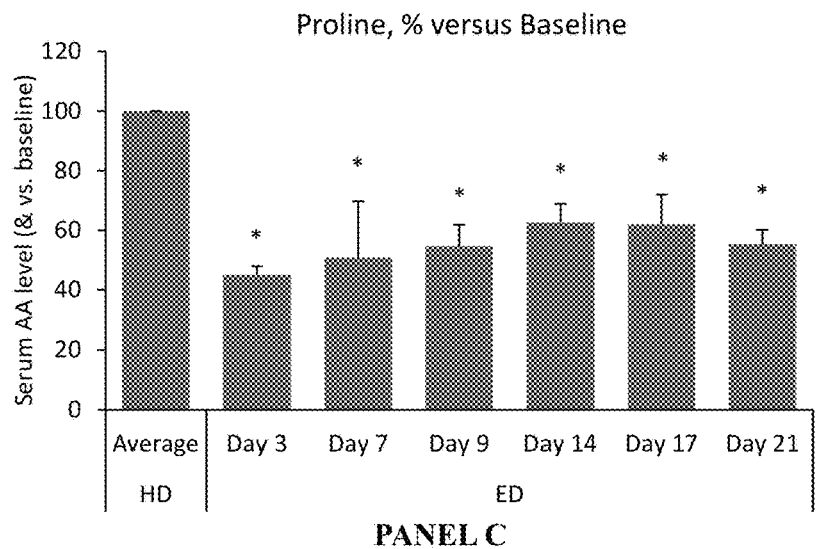

Average serum amino acid levels in the subjects as measured during consumption of their habitual diet (i.e., diet typical of the subject before administration of composition) and after commencement of the experimental diet are shown in FIG. 2 (HD=Habitual Diet; ED=Experimental Diet). FIG. 5, PANEL A illustrates serum levels of proline as a percentage of habitual diet baseline levels throughout the 5 day period (*=p<0.05 ANOVA).

TABLE 41

Formulation lacking proline.

| | Amino acid | Milligrams (mg) per sachet | % of composition (w/w) |
|---|---|---|---|
| 1 | Histidine | 459 | 3.8 |
| 2 | Isoleucine | 459 | 3.8 |
| 3 | Leucine | 1101 | 9.1 |
| 4 | Lysine | 826 | 6.9 |
| 5 | Methionine | 367 | 3 |
| 6 | Phenylalanine | 551 | 4.6 |
| 7 | Threonine | 551 | 4.6 |
| 8 | Tryptophan | 275 | 2.3 |
| 9 | Valine | 918 | 7.6 |
| 10 | Cysteine | 229 | 1.9 |
| 11 | Tyrosine | 229 | 1.9 |
| 12 | Glutamine | 994 | 8.3 |
| 13 | Arginine | 795 | 6.6 |
| 14 | Alanine | 612 | 5.1 |
| 15 | Aspartic Acid | 918 | 7.6 |
| 16 | Asparagine | 535 | 4.4 |
| 17 | Glutamic acid | 1223 | 10.2 |
| 18 | Serine | 331 | 2.8 |
| 19 | Glycine | 662 | 5.5 |
| 20 | Proline | 0 | 0 |

Example 18: Study of Amino Acid Levels in Healthy Subject Administered Amino Acid Formulation Lacking Proline Four healthy human subjects recruited according to the criteria outlined in Example 17 were allowed to consume their habitual diet (i.e., diet typical of the subject before administration of composition) for two days to establish a baseline level of serum amino acids. Each of the subjects was then fed a 1613 kcal/day low protein whole food diet for five days. The diet consisted of 9 g of protein/day and ~350 mg proline/day. 50%, 2%, and 48% of the daily caloric content was derived from carbohydrates, protein, and fat, respectively. Throughout the five day period, the diet was administered in conjunction with doses of a supplemental amino acid formulation in sachet form. Each sachet contained the components listed in Table 42. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for amino acid content via LC-MS.

Figure 3:
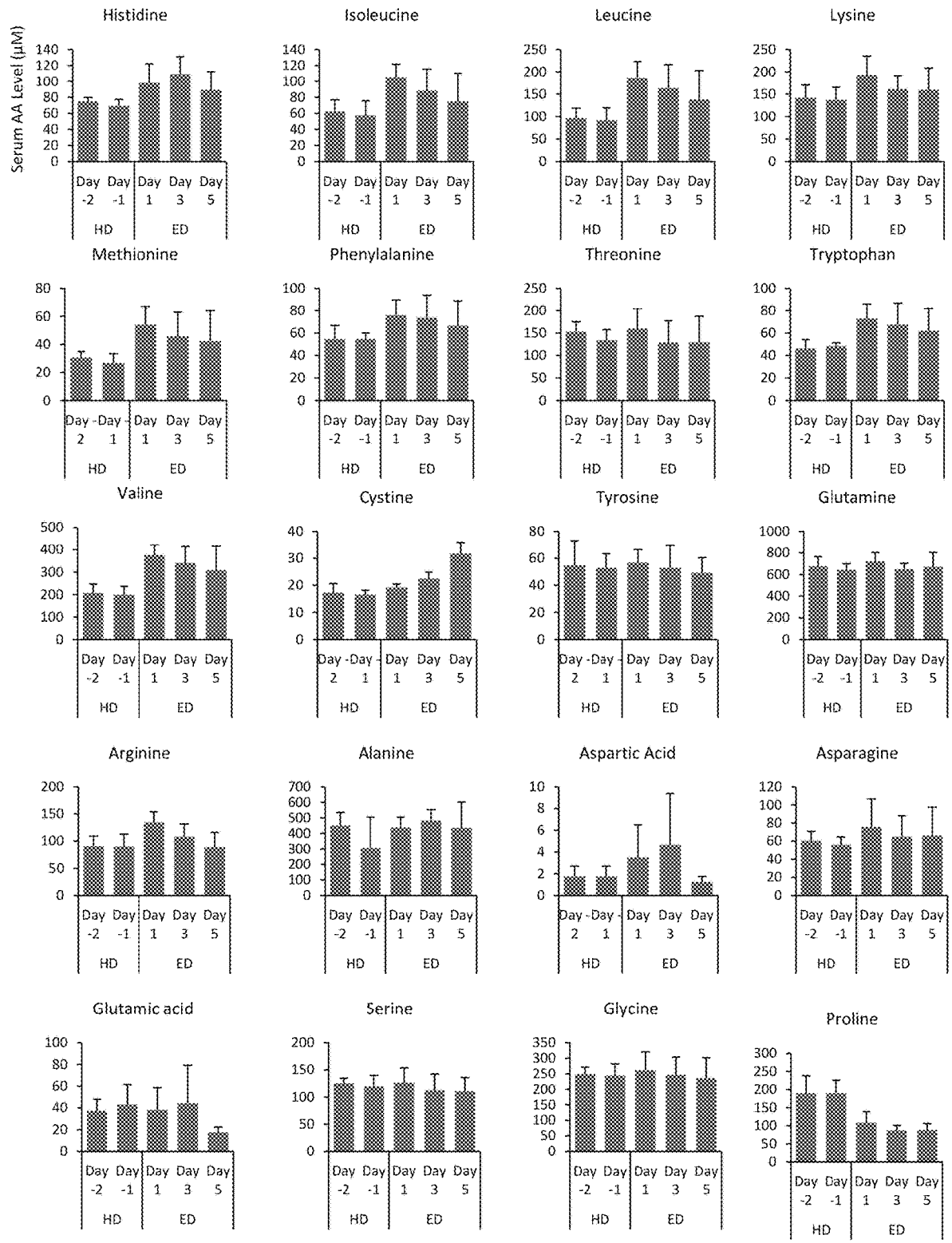
FIG. 3 provides charts illustrating serum levels of amino acids in subjects before and after administration of a diet deficient in proline as described in Example 18.

Average serum amino acid levels in the subjects as measured during consumption of their habitual diet (i.e., diet typical of the subject before administration of composition) and after commencement of the experimental diet are shown in FIG. 3 (HD=Habitual Diet; ED=Experimental Diet). FIG. 5, PANEL B illustrates serum levels of proline as a percentage of habitual diet baseline levels throughout the 5 day period (*=p<0.05 ANOVA).

TABLE 42

Formulation lacking proline.

| | Amino acid | Milligrams (mg) per sachet | % of composition (w/w) |
|---|---|---|---|
| 1 | Histidine | 480 | 4 |
| 2 | Isoleucine | 650 | 5.4 |
| 3 | Leucine | 1250 | 10.4 |
| 4 | Lysine | 930 | 7.7 |
| 5 | Methionine | 370 | 3.1 |
| 6 | Phenylalanine | 650 | 5.4 |
| 7 | Threonine | 430 | 3.6 |
| 8 | Tryptophan | 240 | 2 |
| 9 | Valine | 920 | 7.6 |
| 10 | Cysteine | 240 | 2 |
| 11 | Tyrosine | 250 | 2.1 |
| 12 | Glutamine | 900 | 7.5 |
| 13 | Arginine | 850 | 7.1 |
| 14 | Alanine | 450 | 3.7 |
| 15 | Aspartic Acid | 800 | 6.6 |
| 16 | Asparagine | 450 | 3.7 |
| 17 | Glutamic acid | 1300 | 10.8 |
| 18 | Serine | 330 | 2.7 |
| 19 | Glycine | 550 | 4.6 |
| 20 | Proline | 0 | 0 |

Example 19: Study of Amino Acid Levels in Healthy Subject Administered Taurine-Supplemented Amino Acid Formulation Lacking Proline Four healthy human subjects recruited according to the criteria outlined in Example 17 were allowed to consume their habitual diet (i.e., diet typical of the subject before administration of composition) for two days to establish a baseline level of serum amino acids. Each of the subjects was then fed a 1613 kcal/day low protein whole food diet for 21 days. The diet consisted of 9 g of protein/day and ~350 mg proline/day. 50%, 2%, and 48% of the daily caloric content was derived from carbohydrates, protein, and fat, respectively. Throughout the 21 day period, the diet was administered in conjunction with doses of a supplemental amino acid formulation in sachet form.

Each sachet contained the components listed in Table 43. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for amino acid content via LC-MS.

Figure 4:
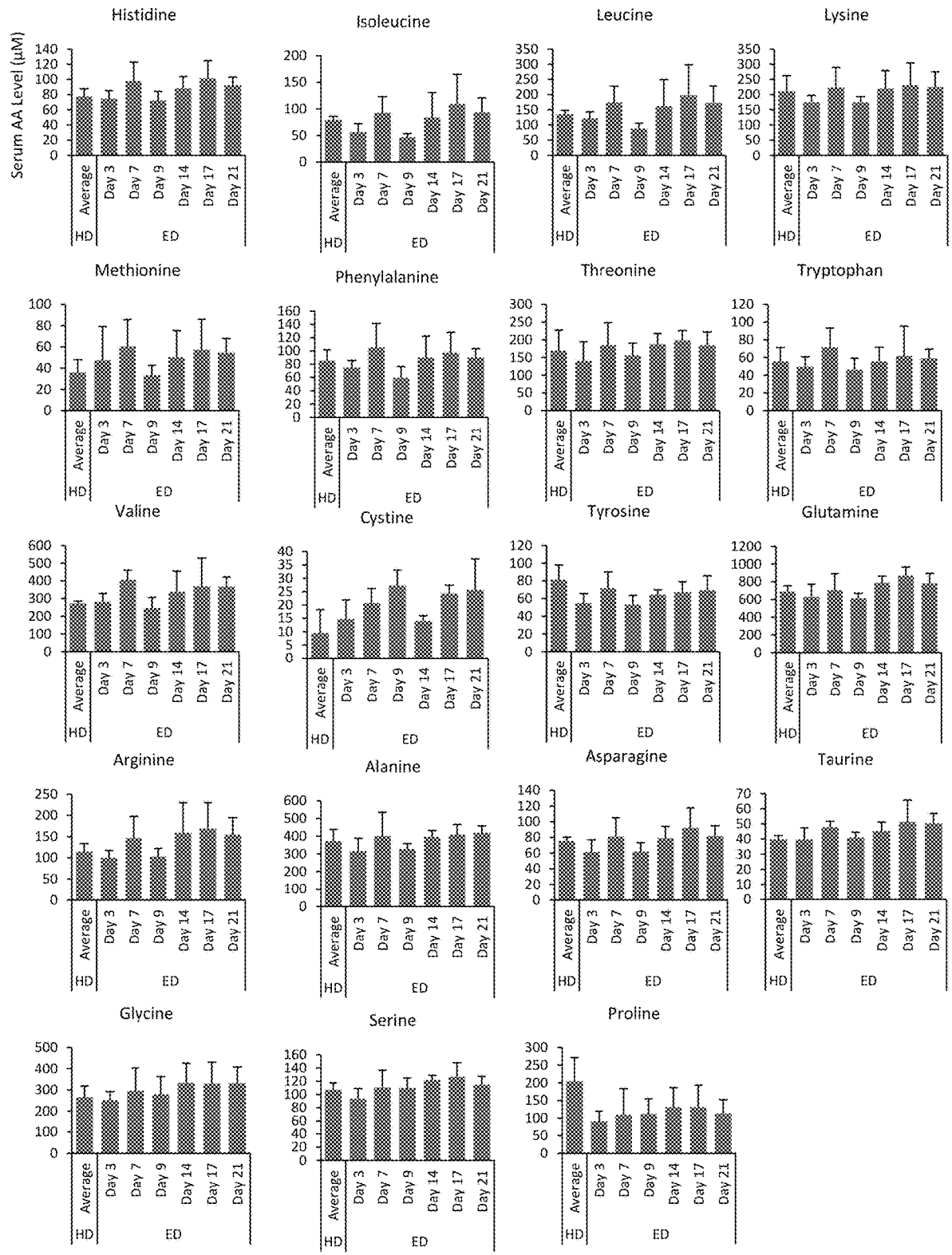
FIG. 4 provides charts illustrating serum levels of amino acids in subjects before and after administration of a diet deficient in proline as described in Example 19.

Average serum amino acid levels in the subjects as measured during consumption of their habitual diet (i.e., diet typical of the subject before administration of composition) and after commencement of the experimental diet are shown in FIG. 4 (HD=Habitual Diet; ED=Experimental Diet). FIG. 5, PANEL C illustrates serum levels of proline as a percentage of habitual diet baseline levels throughout the 21 day period (*=p<0.05 ANOVA).

TABLE 43

Taurine-supplemented formulation lacking proline.

|   | Amino acid | Milligrams (mg) per sachet | % of composition (w/w) |
|---|---|---|---|
| 1 | Histidine | 480 | 4 |
| 2 | Isoleucine | 650 | 5.4 |
| 3 | Leucine | 1250 | 10.3 |
| 4 | Lysine | 930 | 7.7 |
| 5 | Methionine | 370 | 3.1 |
| 6 | Phenylalanine | 650 | 5.4 |
| 7 | Threonine | 430 | 3.6 |
| 8 | Tryptophan | 240 | 2 |
| 9 | Valine | 920 | 7.6 |
| 10 | Cysteine | 240 | 2 |
| 11 | Tyrosine | 250 | 2.1 |
| 12 | Glutamine | 900 | 7.4 |
| 13 | Arginine | 850 | 7 |
| 14 | Alanine | 450 | 3.7 |
| 15 | Aspartic Acid | 800 | 6.6 |
| 16 | Asparagine | 450 | 3.7 |
| 17 | Glutamic acid | 1300 | 10.8 |
| 18 | Serine | 330 | 2.7 |
| 19 | Glycine | 550 | 4.5 |
| 20 | Proline | 0 | 0 |
| 21 | Taurine | 50 | 0.4 |

Example 20: Study of Amino Acid Levels in Pancreatic Cancer Patients Administered Taurine-Supplemented Amino Acid Formulation Lacking Proline Baseline levels of serum proline were determined in four human subjects diagnosed with pancreatic cancer. Each of the subjects was then fed a 1613 kcal/day low protein whole food diet for four weeks. The diet consisted of 9 g of protein/day and ~350 mg proline/day. 50%, 2%, and 48% of the daily caloric content was derived from carbohydrates, protein, and fat, respectively. Throughout the four week period, the diet was administered in conjunction with doses of a supplemental amino acid formulation in sachet form. Each sachet contained the components listed in Table 44. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for serum proline content via LC-MS.

Figure 6:
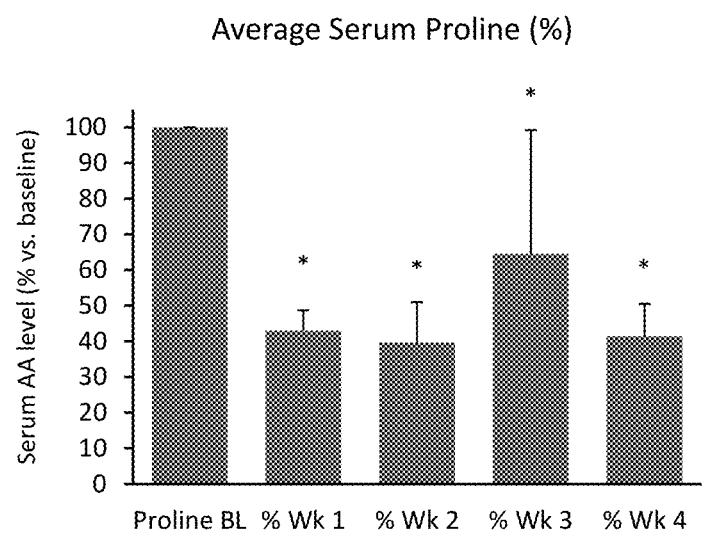
FIG. 6 is a chart illustrating serum levels of proline as a percentage of pre-diet baseline levels in pancreatic cancer patients administered a diet deficient in proline as described in Example 20.

Average serum proline levels in the subjects throughout the 4 week period as a percentage of baseline (BL) levels measured during consumption of their habitual diet are shown in FIG. 6 (*=p <0.05 ANOVA).

TABLE 44

Taurine-supplemented formulation lacking proline.

|   | Amino acid | Milligrams (mg) per sachet | % of composition (w/w) |
|---|---|---|---|
| 1 | Histidine | 480 | 4 |
| 2 | Isoleucine | 650 | 5.4 |
| 3 | Leucine | 1,250 | 10.4 |
| 4 | Lysine | 930 | 7.7 |
| 5 | Methionine | 330 | 2.7 |
| 6 | Phenylalanine | 650 | 5.4 |
| 7 | Threonine | 500 | 4.1 |
| 8 | Tryptophan | 200 | 1.7 |
| 9 | Valine | 920 | 7.6 |
| 10 | Cysteine | 210 | 1.7 |
| 11 | Tyrosine | 250 | 2.1 |
| 12 | Glutamine | 900 | 7.5 |
| 13 | Arginine | 850 | 7.1 |
| 14 | Alanine | 450 | 3.7 |
| 15 | Aspartic Acid | 800 | 6.6 |
| 16 | Asparagine | 450 | 3.7 |
| 17 | Glutamic acid | 1,300 | 10.8 |
| 18 | Proline | 0 | 0 |
| 19 | Serine | 330 | 2.7 |
| 20 | Glycine | 550 | 4.6 |
| 21 | Taurine | 50 | 0.4 |

Example 21: Study of Amino Acid Levels in Healthy Subject Administered Amino Acid Formulation Lacking Serine and Glycine A healthy human subject recruited according to the criteria outlined in Example 17 was allowed to consume their habitual diet (i.e., diet typical of the subject before administration of composition) for one day to establish a baseline level of serum amino acids. The subject was then fed a 1711 kcal/day low protein and low carbohydrate diet for five days. The diet consisted of 10 g of protein/day, ~420 mg proline/day, ~410 mg serine/day, and ~230 mg glycine/day. 9%, 2%, and 89% of the daily caloric content was derived from carbohydrates, protein, and fat, respectively. Throughout the five day period, the diet was administered in conjunction with doses of a supplemental amino acid formulation in sachet form. Each sachet contained the components listed in Table 45. The subject consumed a daily total of 0.8 grams of the supplement per kilogram subject body mass in multiple sachets spread throughout the day. Blood samples were collected from each subject 2 hours after lunch each day and analyzed for serum amino acid content via LC-MS.

Figure 7:
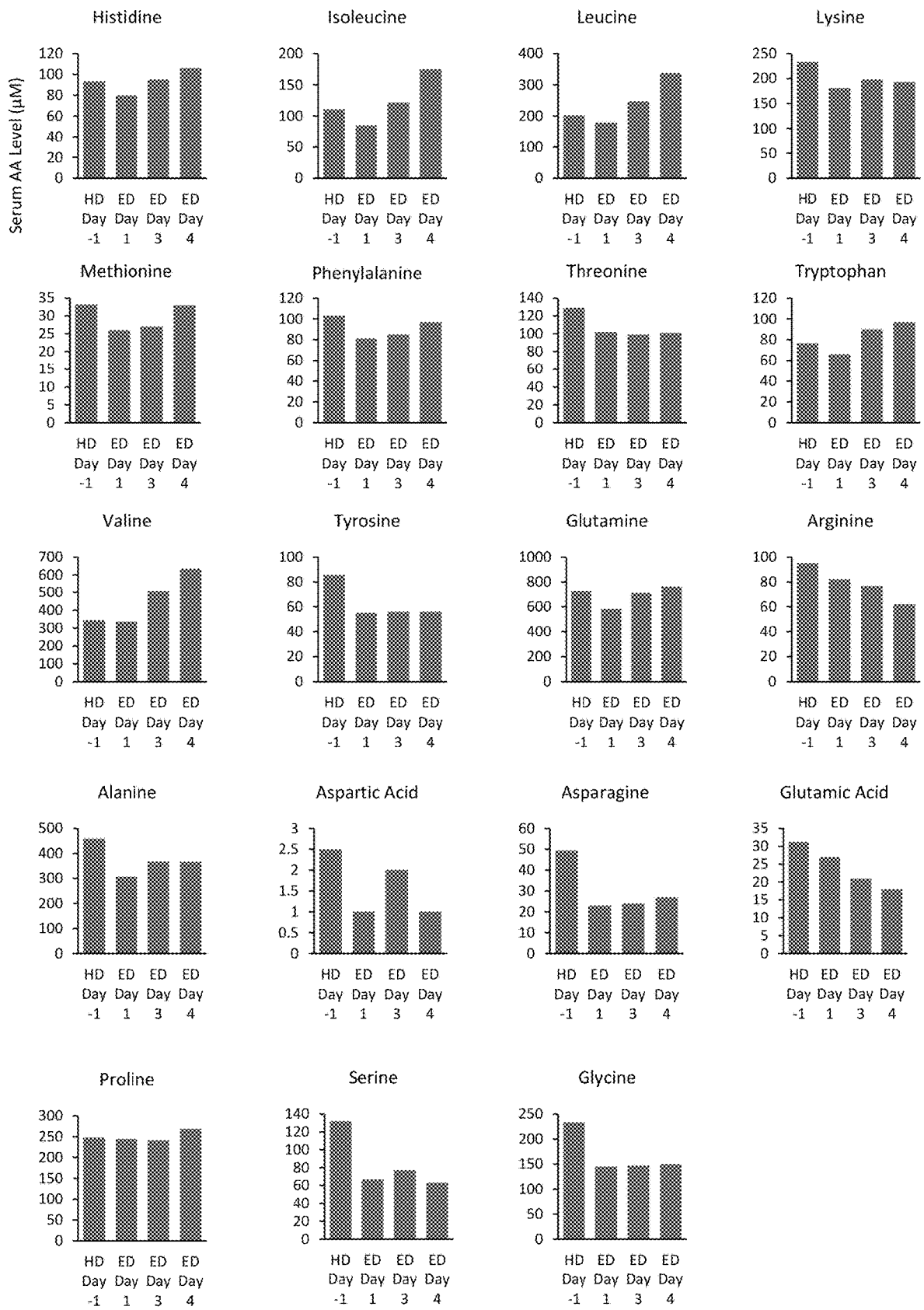
FIG. 7 provides charts illustrating serum levels of amino acids in subjects before and after administration of a diet deficient in serine and glycine as described in Example 21.

Average serum amino acid levels in the subjects as measured during consumption of their habitual diet and after commencement of the experimental diet are shown in FIG. 7 (HD=Habitual Diet; ED=Experimental Diet).

TABLE 45

Formulation lacking serine and glycine

|   | Amino acid | Milligrams (mg) per sachet | % of composition (w/w) |
|---|---|---|---|
| 1 | Histidine | 450 | 4.3 |
| 2 | Isoleucine | 500 | 4.8 |
| 3 | Leucine | 1000 | 9.7 |
| 4 | Lysine | 900 | 8.7 |
| 5 | Methionine | 300 | 2.9 |
| 6 | Phenylalanine | 600 | 5.8 |
| 7 | Threonine | 410 | 4 |
| 8 | Tryptophan | 200 | 1.9 |
| 9 | Valine | 700 | 6.8 |

TABLE 45-continued

Formulation lacking serine and glycine

|    | Amino acid    | Milligrams (mg) per sachet | % of composition (w/w) |
|----|---------------|----------------------------|------------------------|
| 10 | Cysteine      | 220                        | 2.1                    |
| 11 | Tyrosine      | 220                        | 2.1                    |
| 12 | Glutamine     | 600                        | 5.8                    |
| 13 | Arginine      | 750                        | 7.2                    |
| 14 | Alanine       | 300                        | 2.9                    |
| 15 | Aspartic Acid | 500                        | 4.8                    |
| 16 | Asparagine    | 400                        | 3.9                    |
| 17 | Glutamic acid | 1200                       | 11.6                   |
| 18 | Proline       | 1100                       | 10.6                   |
| 19 | Serine        | 0                          | 0                      |
| 20 | Glycine       | 0                          | 0                      |

Example 22: Study of Amino Acid Levels in Healthy Subject Administered Taurine-Supplemented Amino Acid Formulation Lacking Serine, Glycine, and Proline Three healthy human subjects recruited according to the criteria outlined in Example 17 were allowed to consume their habitual diet (i.e., diet typical of the subject before administration of composition) for two days to establish a baseline level of serum amino acids. The subjects were then fed a 1711 kcal/day low protein and low carbohydrate diet for 16-18 days. The diet consisted of 10 g of protein/day, ~420 mg proline/day, ~410 mg serine/day, and ~230 mg glycine/day. 9%, 2%, and 89% of the daily caloric content was derived from carbohydrates, protein, and fat, respectively. Throughout the 16-18 day period, the diet was administered in conjunction with doses of a supplemental amino acid formulation in sachet form. Each sachet contained the components listed in Table 46. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for serum amino acid content via LC-MS.

Figure 8:
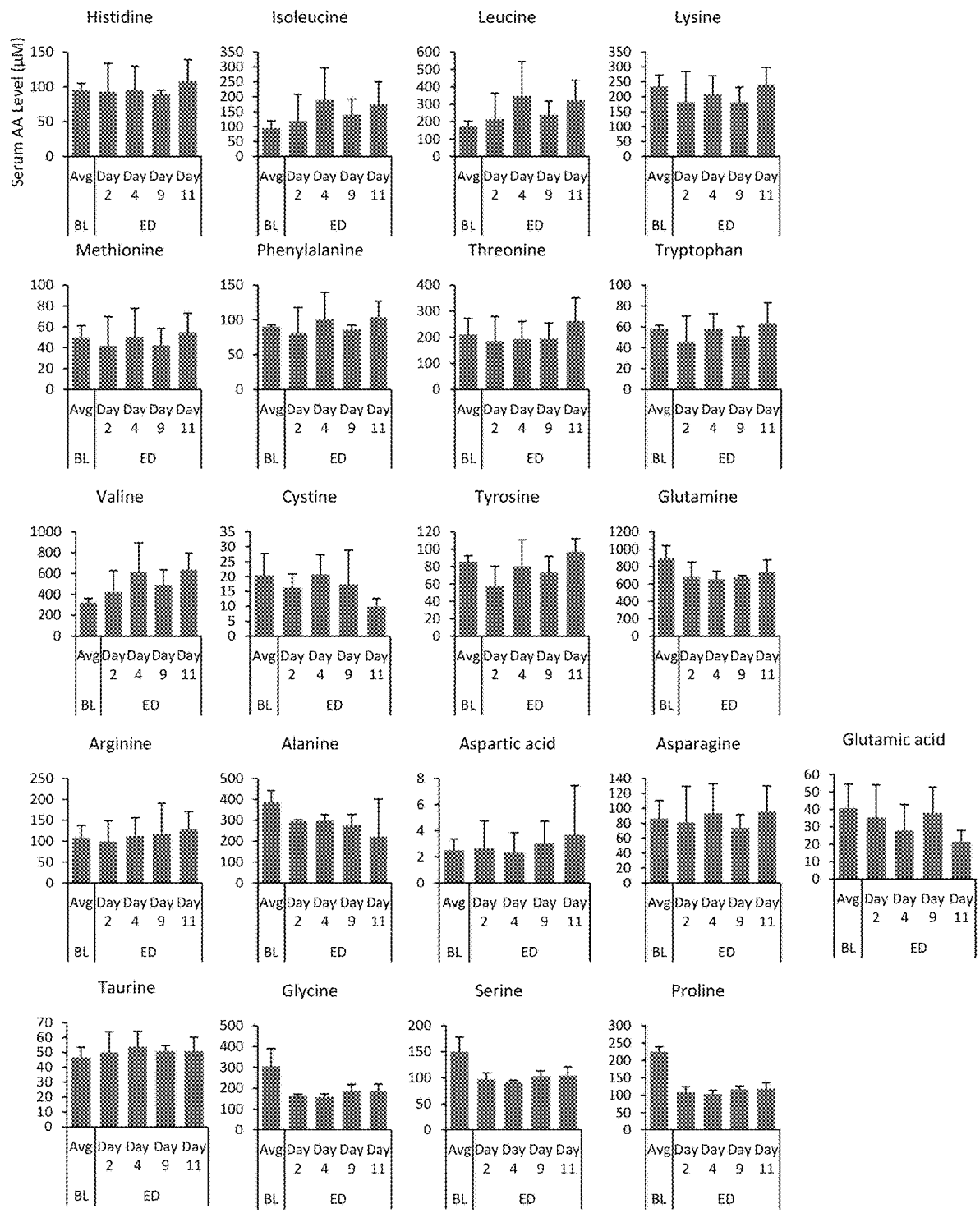
FIG. 8 provides charts illustrating serum levels of amino acids in subjects before and after administration of a diet deficient in proline, glycine, and serine as described in Example 22.
Figure 9:
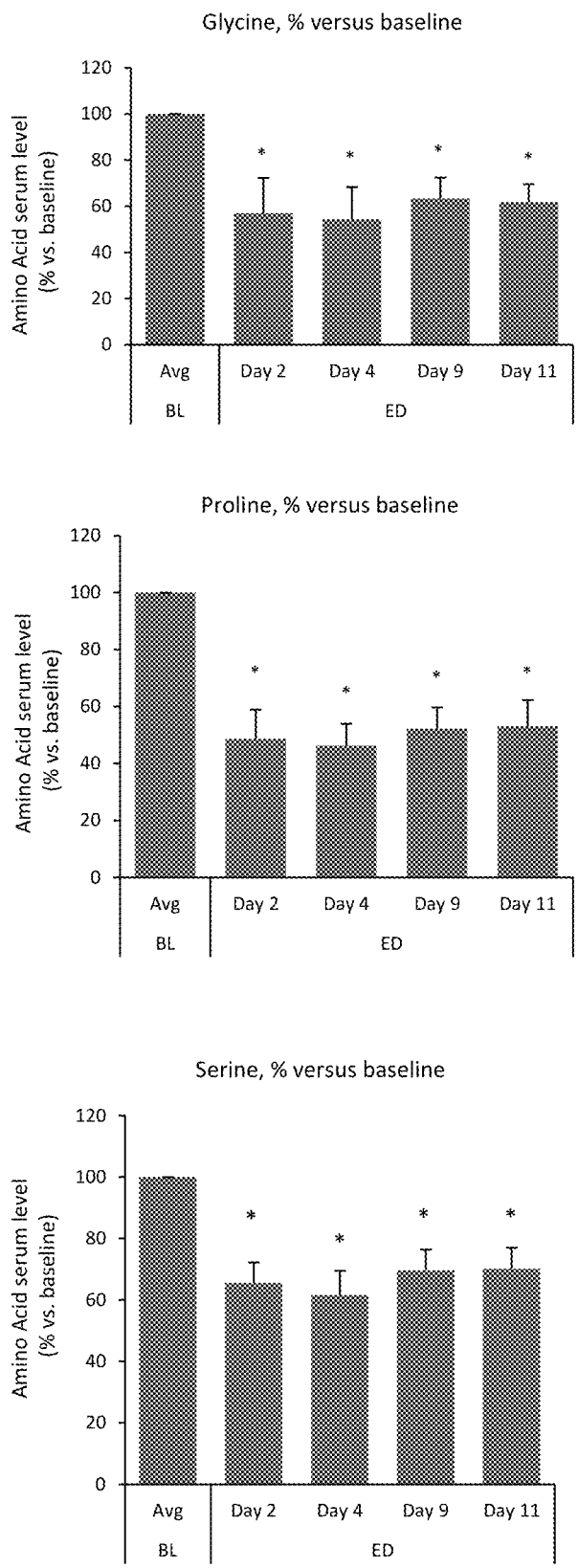
FIG. 9 provides charts illustrating serum levels of serine, proline, and glycine as a percentage of pre-diet baseline levels in subjects administered the diet described in Example 22.

Average serum amino acid levels in the subjects as measured during consumption of their habitual diet (i.e., diet typical of the subject before administration of composition) and after commencement of the experimental diet are shown in FIG. 8 (HD=Habitual Diet; ED=Experimental Diet). FIG. 9 illustrates serum levels of proline as a percentage of habitual diet baseline during consumption of the experimental diet (*=p<0.05 ANOVA, BL=Baseline (habitual diet); Avg=average).

TABLE 46

Taurine-supplemented formulation lacking proline, serine, and glycine

|    | Amino acid    | Milligrams (mg) per sachet | % of composition (w/w) |
|----|---------------|----------------------------|------------------------|
| 1  | Histidine     | 550                        | 5.2                    |
| 2  | Isoleucine    | 650                        | 6.1                    |
| 3  | Leucine       | 1,250                      | 11.7                   |
| 4  | Lysine        | 1,000                      | 9.4                    |
| 5  | Methionine    | 300                        | 2.8                    |
| 6  | Phenylalanine | 750                        | 7                      |
| 7  | Threonine     | 550                        | 5.2                    |
| 8  | Tryptophan    | 220                        | 2.1                    |
| 9  | Valine        | 900                        | 8.5                    |
| 10 | Cysteine      | 180                        | 1.7                    |
| 11 | Tyrosine      | 300                        | 2.8                    |
| 12 | Glutamine     | 300                        | 2.8                    |
| 13 | Arginine      | 950                        | 8.9                    |
| 14 | Alanine       | 550                        | 5.2                    |
| 15 | Aspartic Acid | 950                        | 8.9                    |
| 16 | Asparagine    | 600                        | 5.6                    |
| 17 | Glutamic acid | 600                        | 5.6                    |
| 18 | Proline       | 0                          | 0                      |
| 19 | Serine        | 0                          | 0                      |
| 20 | Glycine       | 0                          | 0                      |
| 21 | Taurine       | 50                         | 0.5                    |

Example 23: Study of Amino Acid Levels in Healthy Subject Administered Taurine-Supplemented Amino Acid Formulation Lacking Serine, Glycine, and Proline Two groups consisting of one healthy subject each recruited according to the criteria outlined in Example 17 were allowed to consume their habitual diet (i.e., diet typical of the subject before administration of composition) for two days to establish a baseline level of serum amino acids. The first group was then fed a 1711 kcal/day low protein and low carbohydrate diet on a daily basis for 16 days. The second group followed an identical dietary regimen, except that the second group was directed to consume their habitual diet in place of the experimental diet on day 7 and day 14 of the 16 day period. In each group, the experimental diet consisted of 10 g of protein/day, ~420 mg proline/day, ~410 mg serine/day, and ~230 mg glycine/day. 9%, 2%, and 89% of the daily caloric content was derived from carbohydrates, protein, and fat, respectively.

Throughout the 16 day period, the experimental diet was administered in conjunction with doses of a supplemental amino acid formulation in sachet form, except on days where subjects were directed to consume their habitual diets. Each sachet contained the components listed in Table 46 of Example 22. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for serum amino acid content via LC-MS.

Figure 10:
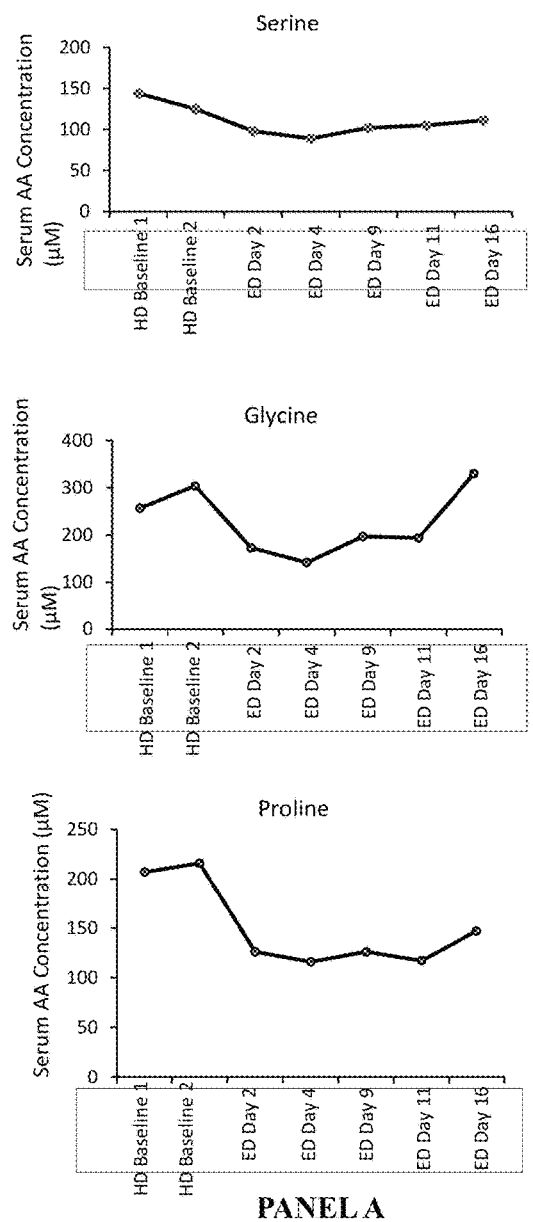
FIG. 10 provides charts illustrating serum levels of proline, glycine, and serine in subjects administered a diet deficient in serine, proline, and glycine on a daily basis (PANEL A) or intermittently (PANEL B) according to the protocol described in Example 23. PANEL C (LEFT) shows a chart comparing serum amino acid as a % of habitual diet for subjects administered a diet deficient in serine, glycine, or proline on a daily basis for 11 days or intermittently for 11 days. PANEL C (RIGHT) shows a chart comparing serum amino acid as a % of habitual diet for subjects administered a diet deficient in serine, glycine, or proline on a daily basis for 16 days or intermittently for 18 days.
Figure 10:
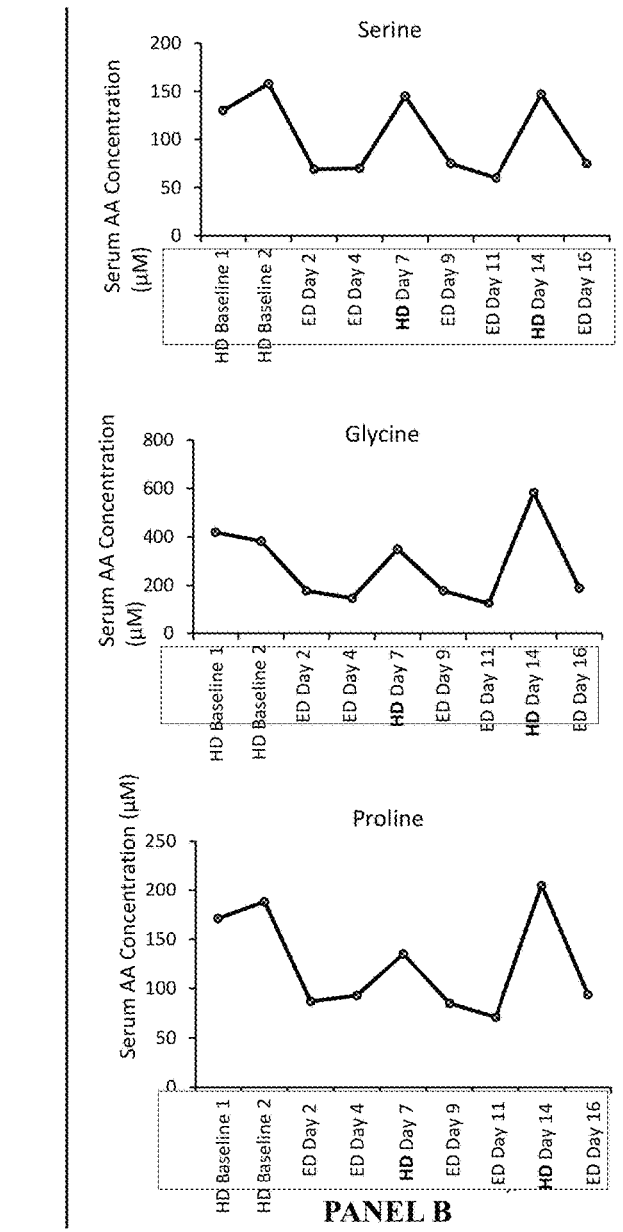
Figure 10:
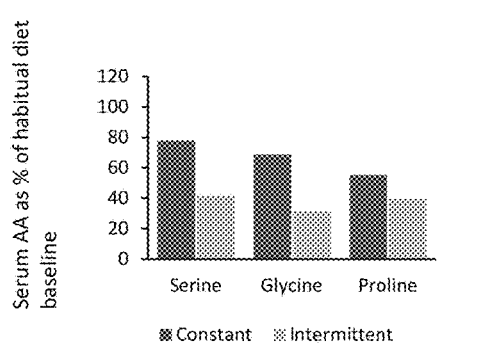
Figure 10:
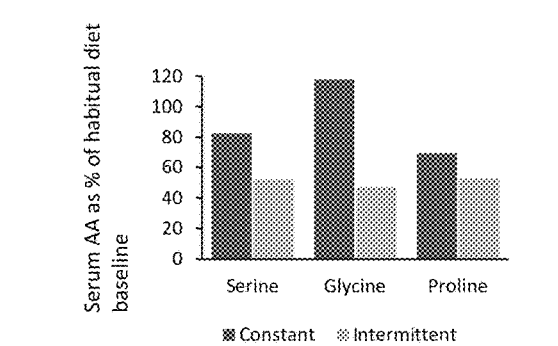

Average serum amino acid levels in the subjects as measured during consumption of their habitual diet (i.e., diet typical of the subject before administration of composition) and after commencement of the experimental diet are shown in FIG. 10, PANEL A for the first group that consumed the diet on a constant, daily basis, and in PANEL B for the second group that consumed the diet on an intermittent basis (HD=Habitual Diet; ED=Experimental Diet). FIG. 10, PANEL C illustrates serum levels of serine, glycine, and proline as a percentage of habitual diet baseline levels throughout the 21 day period in both constant and intermittent groups.

Example 24: Study of Amino Acid Levels in Healthy Subject Administered Taurine-Supplemented Amino Acid Formulation Lacking Serine, Glycine, Glutamate, Glutamine, and Cysteine Two groups of healthy human subjects consisting of two subjects each recruited according to the criteria outlined in Example 17 were allowed to consume their habitual diet (i.e., diet typical of the subject before administration of composition) for two days to establish a baseline level of serum amino acids.

In group 1, the subjects were then fed a 1613 kcal/day low-protein whole food diet for four days. The diet consisted of 9 g of protein/day and ~350 mg proline/day. 50%, 2%, and 48% of the daily caloric content was derived from carbohydrates, protein, and fat, respectively.

In group 2, subjects were then fed a 1711 kcal/day low-protein and low-carbohydrate diet for four days. The group 2 diet consisted of 10 g of protein/day, ~420 mg proline/day, ~410 mg serine/day, and ~230 mg glycine/day. 9%, 2%, and 89% of the daily caloric content was derived from carbohydrates, protein, and fat, respectively.

Throughout the four day period in each group, the diets were administered in conjunction with doses of a supplemental amino acid formulation in sachet form. Each sachet contained the components listed in Table 47. The number of sachets administered to each subject was adjusted such that each subject consumed a daily total of 0.8 grams of the supplement per kilogram body mass. Sachets and meals were consumed at typical times of day (breakfast between 07:00-08:00, lunch between 12:00-13:00, dinner between 18:00-19:00). Plain water (with or without non-caloric sweetener) was permitted ad libitum. Blood samples were collected from each subject 2 hours after lunch each day and analyzed for serum amino acid content via LC-MS.

Figure 11:
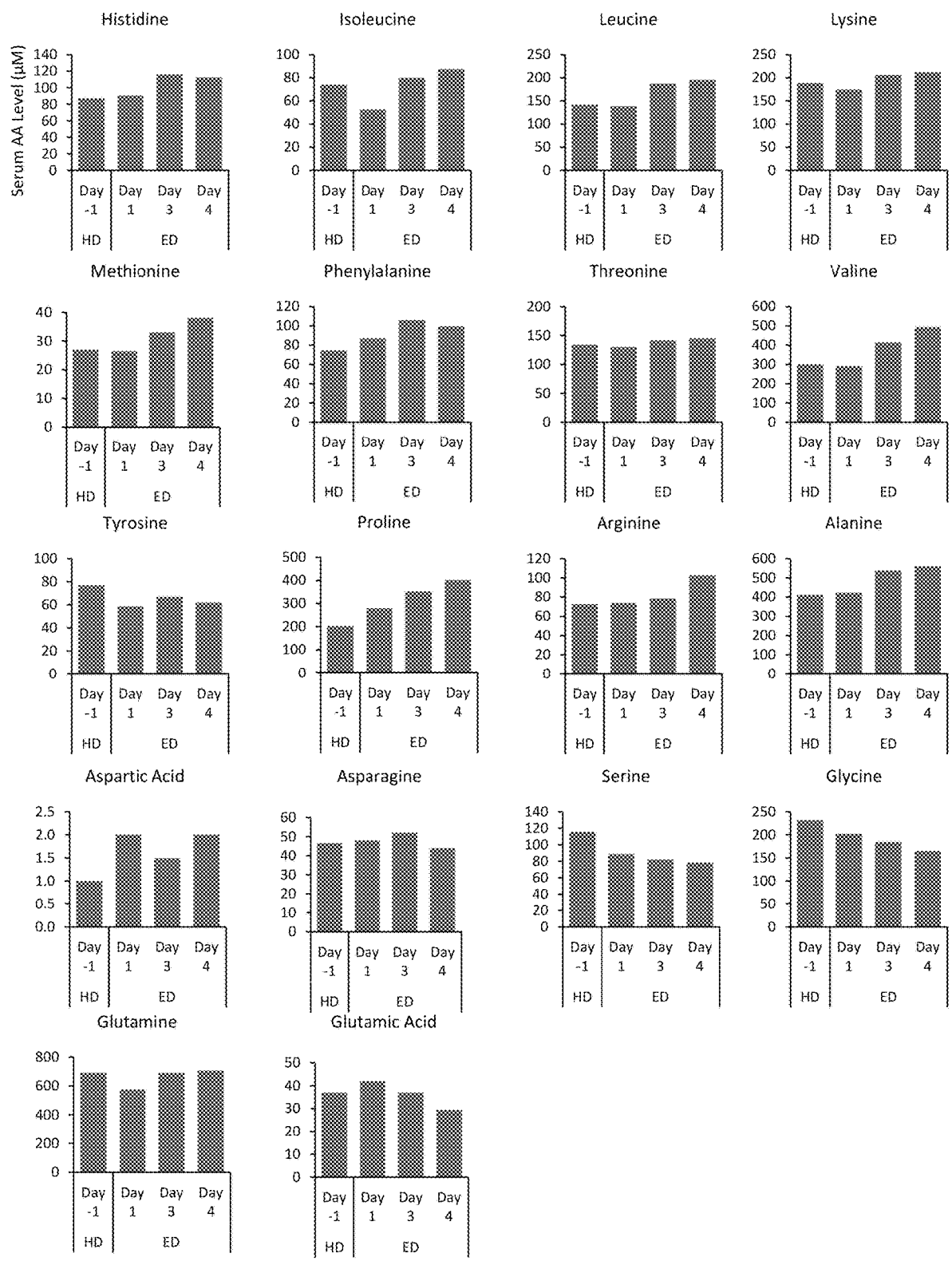
FIG. 11 provides charts illustrating serum levels of amino acids in subjects after administration of the 1613 kcal/day low-protein diet deficient in serine, glycine, glutamate, and cysteine as described in Example 24.
Figure 12:
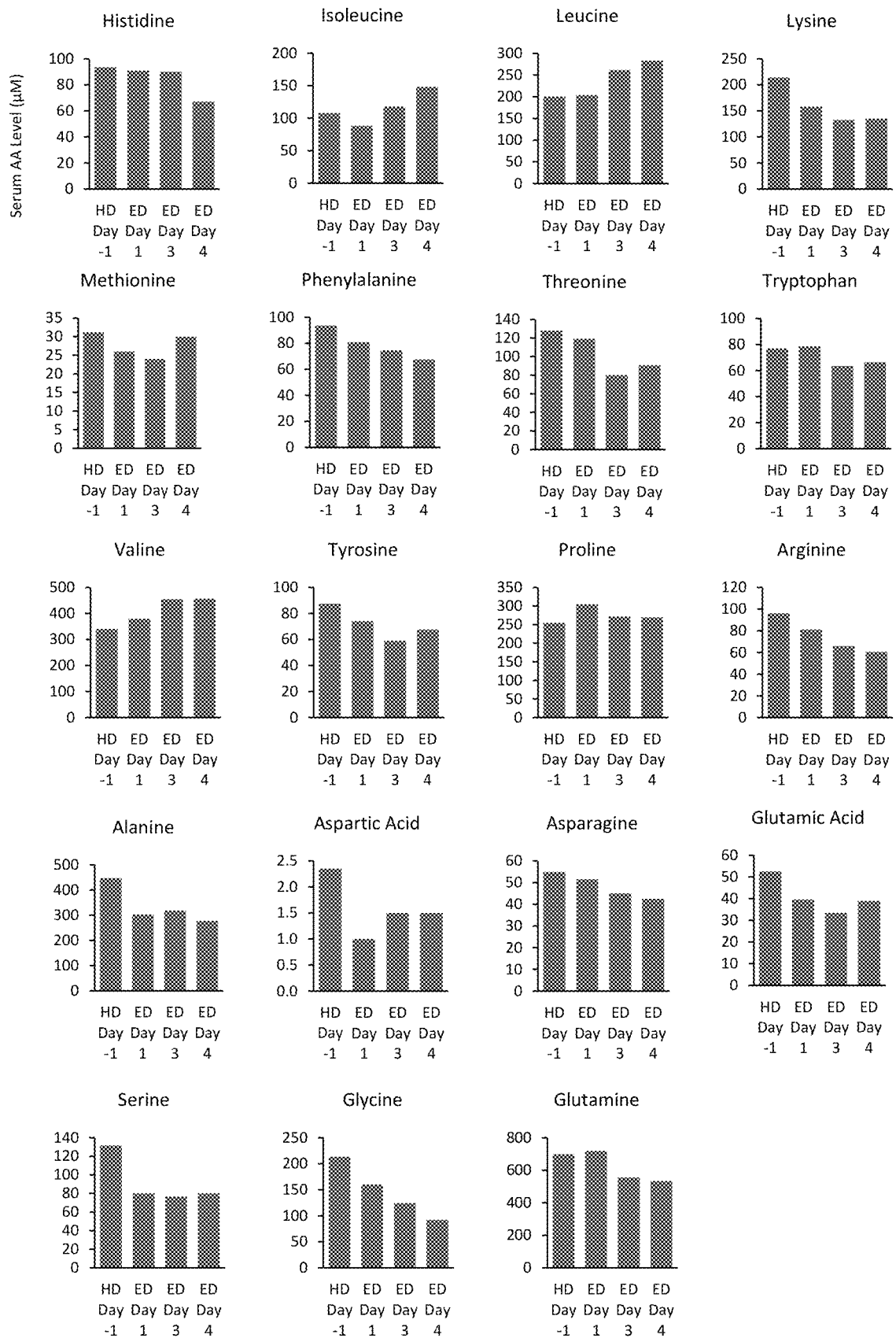
FIG. 12 provides charts illustrating serum levels of amino acids in subjects after administration of the 1711 kcal/day low-protein, low-carbohydrate diet deficient in serine, glycine, glutamate, and cysteine as described in Example 24.
Figure 13:
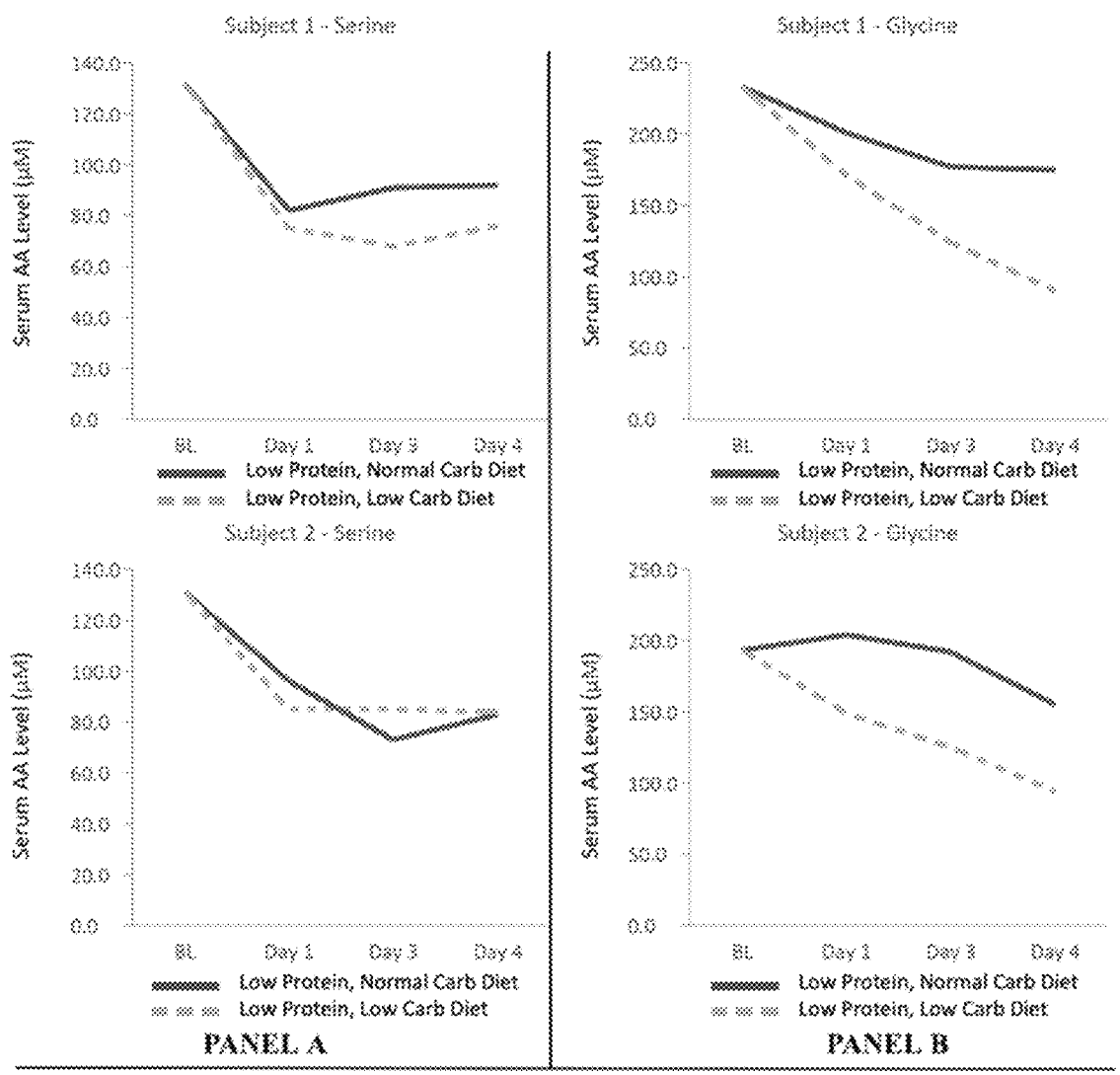
FIG. 13 provides charts illustrating serum levels of amino acids in subjects before and after administration of the 1613 kcal/day low-protein diet (PANEL A) or the 1711 kcal/day low-protein, low-carbohydrate diet (PANEL B) described in Example 24. PANEL C shows average % serum levels after administration of the low-protein diet (left) and average % serum levels after administration of the low-protein, low-carbohydrate diet (right).
Figure 13:
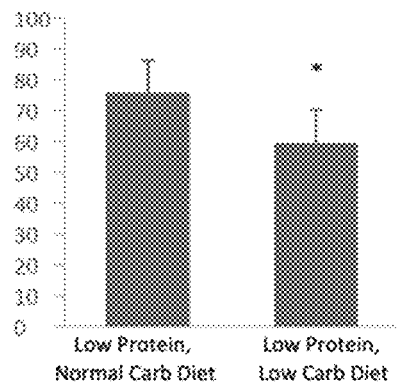

Average serum amino acid levels as measured during consumption of habitual diet and after commencement of the experimental diets are shown in FIG. 11 for the 1613 kcal/day low protein whole food group and in FIG. 12 for the 1711 kcal/day low-protein and low-carbohydrate group (HD=Habitual Diet; ED=Experimental Diet). FIG. 13 provides charts illustrating serum levels of serine and glycine in subjects before and after administration of the 1613 kcal/day low-protein diet (PANEL A) or the 1711 kcal/day low-protein, low-carbohydrate diet (PANEL B) (HD=Habitual Diet; ED=Experimental Diet; *P=0.00019, Ttest (2-sided, paired)). PANEL C shows average % serum levels after administration of the low-protein diet (left) and average % serum levels after administration of the low-protein, low-carbohydrate diet (right).

TABLE 47

Formulation lacking serine, glycine, glutamate glutamine, and cysteine

| | Amino acid | Milligrams (mg) per sachet | % of composition (w/w) |
|---|---|---|---|
| 1 | Histidine | 550 | 5.3 |
| 2 | Isoleucine | 650 | 6.3 |
| 3 | Leucine | 1250 | 12.1 |
| 4 | Lysine | 930 | 9 |

TABLE 47-continued

Formulation lacking serine, glycine, glutamate glutamine, and cysteine

| | Amino acid | Milligrams (mg) per sachet | % of composition (w/w) |
|---|---|---|---|
| 5 | Methionine | 350 | 3.4 |
| 6 | Phenylalanine | 700 | 6.8 |
| 7 | Threonine | 410 | 4 |
| 8 | Tryptophan | 240 | 2.3 |
| 9 | Valine | 920 | 8.9 |
| 10 | Cysteine | 0 | 0 |
| 11 | Tyrosine | 250 | 2.4 |
| 12 | Glutamine | 0 | 0 |
| 13 | Arginine | 850 | 8.2 |
| 14 | Alanine | 450 | 4.3 |
| 15 | Aspartic Acid | 800 | 7.7 |
| 16 | Asparagine | 500 | 4.8 |
| 17 | Glutamic acid | 0 | 0 |
| 18 | Proline | 1500 | 14.5 |
| 19 | Serine | 0 | 0 |
| 20 | Glycine | 0 | 0 |

EMBODIMENTS

The following non-limiting embodiments provide illustrative examples of the invention, but do not limit the scope of the invention.

Embodiment 1. A composition comprising in a unit dosage form: a) a non-essential amino acid or a salt thereof, wherein the non-essential amino acid or the salt thereof is not part of a polypeptide; b) a first essential amino acid or a first salt thereof and a second essential amino acid or a second salt thereof, wherein the first essential amino acid or the first salt thereof and the second essential amino acid or the second salt thereof are present in the composition in an equal amount, wherein the first essential amino acid and the first salt thereof and the second essential amino acid and the second salt thereof are not part of a polypeptide; and c) a pharmaceutically acceptable excipient.

Embodiment 2. The composition of embodiment 1, wherein the first essential amino acid or the first salt thereof is histidine, and the second essential amino acid or the second salt thereof is isoleucine.

Embodiment 3. The composition of embodiment 1 or 2, wherein the equal amount is from about 2% to about 6% (w/w).

Embodiment 4. The composition of embodiment 1, wherein the equal amount is from about 5.5% to about 8.3% (w/w).

Embodiment 5. The composition of embodiment 1, wherein the salt of the non-essential amino acid is a pharmaceutically acceptable salt, wherein the first salt is a pharmaceutically acceptable salt, and wherein the second salt is a pharmaceutically acceptable salt.

Embodiment 6. A composition comprising in a powder form: a) an essential amino acid, wherein the essential amino acid is not part of polypeptide; b) a non-essential amino acid, wherein the non-essential amino acid is not part of a polypeptide; and c) a pharmaceutically acceptable excipient, wherein the composition does not comprise serine or glycine, wherein if, in a study of a tumor volume change in a subject, then the tumor volume in a subject administered the composition is reduced by at least about 20% as compared to a subject that is not administered the composition.

Embodiment 7. A composition comprising in a unit dosage form: a) a non-essential amino acid or a salt thereof, wherein the non-essential amino acid or the salt thereof is not part of a polypeptide, b) a first essential amino acid or a first salt thereof and a second essential amino acid or a second salt thereof, wherein the first essential amino acid or the first salt thereof and the second essential amino acid or the second salt thereof are present in the composition in an equal amount, wherein the first essential amino acid and the first salt thereof and the second essential amino acid and the second salt thereof are not part of a polypeptide; and c) a pharmaceutically acceptable excipient, wherein if, in a study of a tumor volume change in a subject, then the tumor volume in a subject administered the composition is reduced by at least about 20% as compared to a subject administered a placebo.

Embodiment 8. A composition comprising in a powder form: a) an essential amino acid, wherein the essential amino acid is not part of polypeptide; b) a non-essential amino acid, wherein the non-essential is not part of a polypeptide; and c) a pharmaceutically acceptable excipient, wherein the composition does not comprise serine or glycine, and wherein if, in a study of a tumor volume change in a subject, then the tumor volume in a subject administered the composition is reduced by at least about 20% as compared to a subject administered a placebo.

Embodiment 9. The composition of any one of embodiments 1-8, wherein the composition is devoid of at least one non-essential amino acid.

Embodiment 10. The composition of any one of embodiments 1-9, wherein the composition is devoid of at least serine.

Embodiment 11. The composition of any one of embodiments 1-10, wherein the composition is devoid of at least glycine.

Embodiment 12. The composition of any one of embodiments 1-11, wherein the composition is devoid of at least proline.

Embodiment 13. The composition of any one of embodiments 1-12, wherein the composition is devoid of at least cysteine.

Embodiment 14. The composition of any one of embodiments 1-13, wherein the composition is devoid of at least tyrosine.

Embodiment 15. The composition of any one of embodiments 1-14, wherein the composition is devoid of at least arginine.

Embodiment 16. The composition of any one of embodiments 1-15, wherein the composition is a pharmaceutical composition.

Embodiment 17. The composition of any one of embodiments 1-16, wherein the unit dosage form has a weight of about 12 grams.

Embodiment 18. The composition of any one of embodiments 1-17, wherein the composition is in a powder form.

Embodiment 19. The composition of any one of embodiments 1-18, further comprising a preservative.

Embodiment 20. The composition of any one of embodiments 1-19, further comprising a pharmaceutically acceptable excipient.

Embodiment 21. The composition of any one of embodiments 1-20, further comprising a flavoring agent.

Embodiment 22. The composition of any one of embodiments 1-21, wherein the composition further comprises taurine, a hydrate thereof, or a salt thereof from about 0.05% to about 2% (w/w).

Embodiment 23. The composition of any one of embodiments 1-22, wherein the composition further comprises from about 1% to about 4% (w/w) of a $Mg^{2+}$ source.

Embodiment 24. The composition of embodiment 23, wherein the $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, or magnesium malate, magnesium orotate, or a hydrate thereof.

Embodiment 25. The composition of embodiment 23, wherein the $Mg^{2+}$ source is magnesium citrate.

Embodiment 26. The composition of embodiment 23, wherein the $Mg^{2+}$ source is magnesium aspartate, and the aspartic acid, the hydrate thereof, or the salt thereof is aspartic acid free acid.

Embodiment 27. The composition of any one of embodiments 1-26, wherein the composition further comprises from about 2% to about 5% of a $K^+$ source.

Embodiment 28. The composition of embodiment 27, wherein the $K^+$ source comprises potassium citrate, potassium phosphate, potassium chloride, potassium sulfate, potassium gluconate, potassium bicarbonate, potassium aspartate, potassium acetate, and potassium orotate.

Embodiment 29. The composition of embodiment 27, wherein the $K^+$ source is potassium chloride.

Embodiment 30. The composition of embodiment 27, wherein the $K^+$ source is potassium aspartate, and the aspartic acid, the hydrate thereof, or the hydrate thereof is aspartic acid free base.

Embodiment 31. The composition of any one of embodiments 1-30, wherein if, in a study of a tumor volume change in a subject, then the tumor volume in a subject administered the composition is reduced by at least about 20% as compared to a subject that is not administered the composition.

Embodiment 32. The composition of embodiment 31, wherein the tumor volume is measured by a caliper measurement.

Embodiment 33. A method of reducing a tumor volume in a subject, the method comprising administering to the subject a therapeutically-effective amount of a composition, wherein the composition is devoid of at least one non-essential amino acid for at least one month.

Embodiment 34. The method of embodiment 33, wherein the subject is on a modified diet, wherein the modified diet provides at least about 50% of a daily caloric content from fats.

Embodiment 35. A method of treating a cancer in a subject in need thereof, wherein the subject is on a modified diet, wherein the modified diet provides at most about 50% of a daily caloric content from carbohydrates, the method comprising administering to the subject a therapeutically-effective amount of a dietary product, wherein the dietary product is devoid of at least one non-essential amino acid.

Embodiment 36. The method of embodiment 35, wherein the cancer is pancreatic cancer.

Embodiment 37. The method of embodiment 35, wherein the cancer is colorectal cancer.

Embodiment 38. The method of embodiment 35, wherein the cancer is breast cancer.

Embodiment 39. A method of reducing an average serum amino acid level of at least one non-essential amino acid in a subject in need thereof, the method comprising: a) administering to the subject a therapeutically-effective amount of a dietary product that is devoid of the at least one non-essential amino acid for a first period of time; wherein the subject is on a modified diet that provides from at least about 1% to at most about 40% of a daily caloric content from carbohydrates during the first period of time; and b) not administering the dietary product to the subject for a second period of time, wherein the subject is on a normal diet that provides at least about 45% of a daily caloric content from carbohydrates during the second period of time.

Embodiment 40. The method of embodiment 39, wherein the first period of time is about 5 days.

Embodiment 41. The method of embodiment 39, wherein the second period of time is about 1 day.

Embodiment 42. The method of embodiment 39, wherein the second period of time is about 2 days.

Embodiment 43. The method of embodiment 39, further comprising cycling step a) and step b).

Embodiment 44. The method of embodiment 43, wherein step a) and step b) are cycled for at least about 1 week.

Embodiment 45. The method of embodiment 43, wherein step a) and step b) are cycled for at least about 1 month.

Embodiment 46. The method of any one of embodiments 39-45, wherein the average serum amino acid level is reduced by at least about 30%.

Embodiment 47. The method of any one of embodiments 39-34, wherein the average serum amino acid level is reduced by at least about 50%.

Embodiment 48. The method of any one of embodiments 39-47, wherein the reduced average serum amino acid level is sustained through the second period of time.

Embodiment 49. The method of any one of embodiments 35-48, wherein the modified diet provides at least about 50% of the daily caloric content from fats.

Embodiment 50. The method of any one of embodiments 35-48, wherein the modified diet provides at least about 80% of the daily caloric content from fats.

Embodiment 51. Embodiment 31. The method of any one of embodiments 35-50, wherein the modified diet provides at most about 30% of the daily caloric contents from carbohydrates.

Embodiment 52. The method of any one of embodiments 35-50, wherein the modified diet provides at most about 15% of the daily caloric contents from carbohydrates.

Embodiment 53. The method of any one of embodiments 35-52, wherein the modified diet provides at most about 10 g protein/day.

Embodiment 54. The method of any one of embodiments 35-52, wherein the modified diet provides at most about 9 g protein/day.

Embodiment 55. The method of any one of embodiments 35-54, wherein the modified diet provides at most about 500 mg/day of the at least one non-essential amino acid.

Embodiment 56. The method of any one of embodiments 35-55, wherein the modified diet provides at most about 500 mg/day of serine.

Embodiment 57. The method of any one of embodiments 35-55, wherein the modified diet provides at most about 500 mg/day of glycine.

Embodiment 58. The method of any one of embodiments 33-57, wherein the administering is oral.

Embodiment 59. The method of any one of embodiments 33-58, wherein the administering of the dietary product is 3 times a day.

Embodiment 60. The method of any one of embodiments 33-59, wherein the administering of the dietary product is 4 times a day.

Embodiment 61. The method of any one of embodiments 33-60, wherein the therapeutically-effective amount of the dietary product is from about 0.5 g/kg/day to about 1 g/kg/day.

Embodiment 62. The method of embodiment 61, wherein the therapeutically-effective amount of the dietary product is about 0.8 g/kg/day.

Embodiment 63. The method of any one of embodiments 33-62, wherein the dietary product further comprises from about 2% to about 5% of a $K^+$ source.

Embodiment 64. The method of embodiment 63, wherein the $K^+$ source is potassium chloride.

Embodiment 65. The method of embodiment 63, wherein the $K^+$ source is potassium aspartate, and the aspartic acid, the hydrate thereof, or the hydrate thereof is aspartic acid free base.

Embodiment 66. The method of any one of embodiments 33-65, wherein the dietary product further comprises from about 1% to about 4% (w/w) of a $Mg^{2+}$ source.

Embodiment 67. The method of embodiment 66, wherein the $Mg^{2+}$ source is magnesium citrate.

Embodiment 68. The method of embodiment 66, wherein the $Mg^{2+}$ source is magnesium aspartate, and the aspartic acid, the hydrate thereof, or the salt thereof is aspartic acid free acid.

Embodiment 69. The method of any one of embodiments 33-68, wherein the dietary product further comprises from about 0.05% to about 2% (w/w) of taurine, a hydrate thereof, or a salt thereof.

Embodiment 70. The method of any one of embodiments 33-69, wherein the dietary product further comprises glucose.

Embodiment 71. The method of any one of embodiments 33-70, wherein the at least one non-essential amino acid is proline.

Embodiment 72. The method of any one of embodiments 33-70, wherein the at least one non-essential amino acid is serine.

Embodiment 73. The method of any one of embodiments 33-70, wherein the at least one non-essential amino acid is glycine.

Embodiment 74. The method of any one of embodiments 33-70, wherein the at least one non-essential amino acid is glutamate.

Embodiment 75. The method of any one of embodiments 33-70, wherein the at least one non-essential amino acid is glutamine.

Embodiment 76. The method of any one of embodiments 33-70, wherein the at least one non-essential amino acid is cysteine.

Embodiment 77. The method of any one of embodiments 33-70, wherein the at least one non-essential amino acid is asparagine.

Embodiment 78. The method of any one of embodiments 33-70, wherein the dietary product does not comprise serine or glycine.

Embodiment 79. The method of any one of embodiments 33-70, wherein the dietary product does not comprise serine, glycine, or proline.

Embodiment 80. The method of any one of embodiments 33-70, wherein the dietary product does not comprise serine, glycine, or cysteine.

Embodiment 81. The method of any one of embodiments 33-70, wherein the dietary product does not comprise serine, glycine, proline, or cysteine.

Embodiment 82. The method of any one of embodiments 33-70, wherein the dietary product does not comprise serine, glycine, proline, or tyrosine.

Embodiment 83. The method of any one of embodiments 33-70, wherein the dietary product does not comprise serine, glycine, proline, or arginine.

Embodiment 84. The method of any one of embodiments 33-70, wherein the dietary product does not comprise serine, glycine, proline, cysteine, or tyrosine.

Embodiment 85. The method of any one of embodiments 33-70, wherein the dietary product does not comprise serine, glycine, proline, cysteine, or arginine.

Embodiment 86. The method of any one of embodiments 33-70, wherein the dietary product does not comprise serine, glycine, proline, cysteine, tyrosine, or arginine.

Embodiment 87. The method of any one of embodiments 33-70, wherein the dietary product does not comprise serine, glycine, glutamate, glutamine, or cysteine.

Embodiment 88. The method of any one of embodiments 33-87, further comprising administering a therapeutic agent.

Embodiment 89. The method of embodiment 88, wherein the therapeutic agent is a chemotherapy.

Embodiment 90. The method of embodiment 88, wherein the therapeutic agent is a radiotherapy.

Embodiment 91. The method of embodiment 88, wherein the therapeutic agent is an immunotherapy.

Embodiment 100. A composition comprising in a unit dosage form: a) histidine or a salt thereof from about 2% to about 6% (w/w); b) isoleucine or a salt thereof from about 2% to about 6% (w/w); c) leucine or a salt thereof from about 6% to about 11% (w/w); d) lysine or a salt thereof from about 5% to about 9% (w/w); e) methionine or a salt thereof from about 2% to about 4% (w/w); f) cysteine or a salt thereof from about 1% to about 3% (w/w); g) phenylalanine or a salt thereof from about 3% to about 6% (w/w); h) tyrosine or a salt thereof from about 1% to about 3% (w/w); i) threonine or a salt thereof from about 3% to about 5% (w/w); j) tryptophan or a salt thereof from about 1% to about 3% (w/w); k) valine or a salt thereof from about 5% to about 9% (w/w); l) arginine or a salt thereof from about 5% to about 9% (w/w); m) glutamine or a salt thereof from about 5% to about 11% (w/w); n) alanine or a salt thereof from about 2% to about 7% (w/w); o) aspartic acid or a salt thereof from about 6% to about 10% (w/w); p) asparagine or a salt thereof from about 3% to about 7% (w/w); q) glutamic acid or a salt thereof from about 8% to about 14% (w/w); and r) proline or a salt thereof from about 6% to about 12% (w/w).

Embodiment 102. A composition comprising in a unit dosage form: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); and m) glutamine or a salt thereof from about 7% to about 11% (w/w).

Embodiment 103. A composition comprising in a unit dosage form: a) histidine or a salt thereof from about 2% to about 5% (w/w); b) isoleucine or a salt thereof from about 2% to about 5% (w/w); c) leucine or a salt thereof from about 6% to about 10% (w/w); d) lysine or a salt thereof from about 5% to about 8% (w/w); e) methionine or a salt thereof from about 2% to about 4% (w/w); f) cysteine or a salt thereof from about 1% to about 3% (w/w); g) phenylalanine or a salt thereof from about 3% to about 5% (w/w); h) tyrosine or a salt thereof from about 1% to about 3% (w/w); i) threonine or a salt thereof from about 3% to about 5% (w/w); j) tryptophan or a salt thereof from about 1% to about 3% (w/w); k) valine or a salt thereof from about 5% to about 9% (w/w); l) arginine or a salt thereof from about 5% to about 9% (w/w); m) glutamine or a salt thereof from about 7% to about 11% (w/w); n) alanine or a salt thereof from about 4% to about 7% (w/w); o) aspartic acid or a salt thereof from about 6% to about 10% (w/w); p) asparagine or a salt thereof from about 3% to about 6% (w/w); q) glutamic acid or a salt thereof from about 8% to about 14% (w/w); and r) proline or a salt thereof from about 6% to about 10% (w/w), wherein if, in a study of a tumor volume change in a subject, then the tumor volume in a subject administered the composition is reduced by at least about 20% as compared to a subject that is administered a placebo.

Embodiment 104. The composition of embodiment 101 or 103, wherein the salt of histidine, isoleucine, leucine, lysine, methionine, cysteine, phenylalanine, tyrosine, threonine, tryptophan, valine, arginine, glutamine, alanine, aspartic acid, asparagine, glutamic acid, and proline is a pharmaceutically acceptable salt.

Embodiment 105. A composition comprising in a unit dosage form: a) histidine or a salt thereof from about 5% to about 9% (w/w); b) isoleucine or a salt thereof from about 5% to about 9% (w/w); c) leucine or a salt thereof from about 9% to about 15% (w/w); d) lysine or a salt thereof from about 7% to about 12% (w/w); e) methionine or a salt thereof from about 5% to about 8% (w/w); f) cysteine or a salt thereof from about 4% to about 7% (w/w); g) phenylalanine or a salt thereof from about 6% to about 10% (w/w); h) tyrosine or a salt thereof from about 4% to about 7% (w/w); i) threonine or a salt thereof from about 6% to about 10% (w/w); j) tryptophan or a salt thereof from about 4% to about 7% (w/w); k) valine or a salt thereof from about 8% to about 13% (w/w); l) arginine or a salt thereof from about 5% to about 9% (w/w); and m) glutamine or a salt thereof from about 7% to about 11% (w/w), wherein if a comparison study is conducted, wherein the comparison study comprises administering the composition to a first subject and administering a placebo to a second subject, then a volume of a tumor in the first subject is reduced compared to a volume of a tumor in the second subject.

Embodiment 106. The composition of embodiment 102 or 105, wherein the salt of histidine, isoleucine, leucine, lysine, methionine, cysteine, phenylalanine, tyrosine, threonine, tryptophan, valine, arginine, and glutamine is a pharmaceutically acceptable salt.

Embodiment 107. A composition comprising in a unit dosage form: a) histidine, a hydrate thereof, or a salt thereof from about 3% to about 7% (w/w); b) isoleucine, a hydrate thereof, or a salt thereof from about 3% to about 6% (w/w); c) leucine, a hydrate thereof, or a salt thereof from about 7% to about 11% (w/w); d) lysine, a hydrate thereof, or a salt thereof from about 5% to about 9% (w/w); e) methionine, a hydrate thereof, or a salt thereof from about 2% to about 4% (w/w); f) cysteine, a hydrate thereof, or a salt thereof from about 1% to about 3% (w/w); g) phenylalanine, a hydrate thereof, or a salt thereof from about 3% to about 7% (w/w); h) tyrosine, a hydrate thereof, or a salt thereof from about 1% to about 3% (w/w); i) threonine, a hydrate thereof, or a salt thereof from about 2% to about 5% (w/w); j) tryptophan, a hydrate thereof, or a salt thereof from about 1% to about 3% (w/w); k) valine, a hydrate thereof, or a salt thereof from about 5% to about 9% (w/w); l) arginine, a hydrate thereof, or a salt thereof from about 5% to about 9% (w/w); m) glutamine, a hydrate thereof, or a salt thereof from about 7% to about 11% (w/w); n) alanine, a hydrate thereof, or a salt thereof from about 3% to about 7% (w/w); o) aspartic acid, a hydrate thereof, or a salt thereof from about 6% to about 10% (w/w); p) asparagine, a hydrate thereof, or a salt thereof from about 3% to about 6% (w/w); q) glutamic acid, a hydrate thereof, or a salt thereof from about 8% to about 14% (w/w); r) serine, a hydrate thereof, or a salt thereof from about 2% to about 5% (w/w); and s) glycine, a hydrate thereof, or a salt thereof from about 3% to about 7% (w/w).

Embodiment 108. The composition of embodiment 107, wherein the salt of histidine, isoleucine, leucine, lysine, methionine, cysteine, phenylalanine, tyrosine, threonine, tryptophan, valine, arginine, glutamine, alanine, aspartic acid, asparagine, glutamic acid, serine, and glycine is a pharmaceutically acceptable salt.

Embodiment 109. A composition comprising in a unit dosage form: a) histidine, a hydrate thereof, or a salt thereof from about 3% to about 7% (w/w); b) isoleucine, a hydrate thereof, or a salt thereof from about 4% to about 8% (w/w); c) leucine, a hydrate thereof, or a salt thereof from about 9% to about 13% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 4% (w/w); g) phenylalanine, a hydrate thereof, or a salt thereof from about 5% to about 9% (w/w); h) tyrosine, a hydrate thereof, or a salt thereof from about 1% to about 5% (w/w); i) threonine, a hydrate thereof, or a salt thereof from about 4% to about 8% (w/w); j) tryptophan, a hydrate thereof, or a salt thereof from about 1% to about 4% (w/w); k) valine, a hydrate thereof, or a salt thereof from about 5% to about 10% (w/w); l) arginine, a hydrate thereof, or a salt thereof from about 1% to about 10% (w/w); m) glutamine, a hydrate thereof, or a salt thereof from about 1% to about 5% (w/w); n) alanine, a hydrate thereof, or a salt thereof from about 4% to about 8% (w/w); o) aspartic acid, a hydrate thereof, acid or a salt thereof from about 4% to about 12% (w/w); p) asparagine, a hydrate thereof, or a salt thereof from about 4% to about 8% (w/w); and q) glutamic acid, a hydrate thereof, or a salt thereof from about 5% to about 15% (w/w).

Embodiment 110. A composition comprising in a unit dosage form: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 9% to about 12% (w/w); d) lysine, a hydrate thereof, or a salt thereof from about 8% to about 12% (w/w); e) methionine, a hydrate thereof, or a salt thereof from about 1% to about 4% (w/w); f) cysteine, a hydrate thereof, or a salt thereof from about 1% to about 3% (w/w); g) phenylalanine, a hydrate thereof, or a salt thereof from about 6% to about 8% (w/w); h) tyrosine, a hydrate thereof, or a salt thereof from about 1% to about 4% (w/w); i) threonine, a hydrate thereof, or a salt thereof from about 4% to about 7% (w/w); j) tryptophan, a hydrate thereof, or a salt thereof from about 1% to about 3% (w/w); k) valine, a hydrate thereof, or a salt thereof from about 4% to about 9% (w/w); l) arginine, a hydrate thereof, or a salt thereof from about 7% to about 11% (w/w); m) glutamine, a hydrate thereof, or a salt thereof from about 2% to about 4% (w/w); n) alanine, a hydrate thereof, or a salt thereof from about 4% to about 7% (w/w); o) aspartic acid, a hydrate thereof, or a salt thereof from about 8% to about 11% (w/w); p) asparagine, a hydrate thereof, or a salt thereof from about 4% to about 7% (w/w); and q) glutamic acid, a hydrate thereof, or a salt thereof from about 4% to about 8% (w/w).

Embodiment 111. The composition of embodiment 109 or 110, wherein the salt of histidine, isoleucine, leucine, lysine, methionine, cysteine, phenylalanine, tyrosine, threonine, tryptophan, valine, arginine, glutamine, alanine, aspartic acid, asparagine, and glutamic acid is a pharmaceutically acceptable salt.

Embodiment 112. A composition comprising in a unit dosage form: a) histidine, a hydrate thereof, or a salt thereof from about 4% to about 6% (w/w); b) isoleucine, a hydrate thereof, or a salt thereof from about 5% to about 7% (w/w); c) leucine, a hydrate thereof, or a salt thereof from about 11% to about 13% (w/w); d) lysine, a hydrate thereof, or a salt thereof from about 8% to about 10% (w/w); e) methionine, a hydrate thereof, or a salt thereof from about 2% to about 4% (w/w); f) phenylalanine, a hydrate thereof, or a salt thereof from about 6% to about 8% (w/w); g) tyrosine, a hydrate thereof, or a salt thereof from about 1% to about 3% (w/w); h) threonine, a hydrate thereof, or a salt thereof from about 3% to about 5% (w/w); i) tryptophan, a hydrate thereof, or a salt thereof from about 1% to about 3% (w/w); j) valine, a hydrate thereof, or a salt thereof from about 8% to about 10% (w/w); k) arginine, a hydrate thereof, or a salt thereof from about 7% to about 9% (w/w); l) alanine, a hydrate thereof, or a salt thereof from about 3% to about 5% (w/w); m) aspartic acid, a hydrate thereof, or a salt thereof from about 4% to about 6% (w/w); n) asparagine, a hydrate thereof, or a salt thereof from about 4% to about 7% (w/w); and o) proline, a hydrate thereof, or a salt thereof from about 14% to about 17% (w/w).

Embodiment 113. The composition of embodiment 112, wherein the salt of histidine, isoleucine, leucine, lysine, methionine, phenylalanine, tyrosine, threonine, tryptophan, valine, arginine, alanine, aspartic acid, asparagine, and proline is a pharmaceutically acceptable salt.

Embodiment 114. A composition comprising in a unit dosage form: a) histidine, a hydrate thereof, or a salt thereof from about 3% to about 5% (w/w); b) isoleucine, a hydrate thereof, or a salt thereof from about 5% to about 7% (w/w); c) leucine, a hydrate thereof, or a salt thereof from about 10% to about 12% (w/w); d) lysine, a hydrate thereof, or a salt thereof from about 9% to about 11% (w/w); e) methionine, a hydrate thereof, or a salt thereof from about 2% to about 4% (w/w); f) proline, a hydrate thereof, or a salt thereof from about 9% to about 11% (w/w); g) phenylalanine, a hydrate thereof, or a salt thereof from about 6% to about 8% (w/w); h) tyrosine, a hydrate thereof, or a salt thereof from about 1% to about 4% (w/w); i) threonine, a hydrate thereof, or a salt thereof from about 5% to about 7% (w/w); j) tryptophan, a hydrate thereof, or a salt thereof from about 1% to about 3% (w/w); k) valine, a hydrate thereof, or a salt thereof from about 5% to about 7% (w/w); l) arginine, a hydrate thereof, or a salt thereof from about 1% to about 3% (w/w); m) glutamine, a hydrate thereof, or a salt thereof from about 2% to about 4% (w/w); n) alanine, a hydrate thereof, or a salt thereof from about 5% to about 7% (w/w); o) aspartic acid, a hydrate thereof, or a salt thereof from about 4% to about 12% (w/w); p) asparagine, a hydrate thereof, or a salt thereof from about 5% to about 7% (w/w); and q) glutamic acid, a hydrate thereof, or a salt thereof from about 4% to about 12% (w/w).

Embodiment 115. The composition of embodiment 114, wherein the salt of histidine, isoleucine, leucine, lysine, methionine, proline, phenylalanine, tyrosine, threonine, tryptophan, valine, arginine, glutamine, alanine, aspartic acid, asparagine, and glutamic acid is a pharmaceutically acceptable salt.

Embodiment 116. The composition of any one of embodiments 100-115, wherein the composition is a pharmaceutical composition.

Embodiment 117. The composition of any one of embodiments 100-115, wherein the composition is a medical food.

Embodiment 118. The composition of any one of embodiments 100-115, wherein the composition is a nutritional supplement.

Embodiment 119. The composition of any one of embodiments 100-118, wherein the unit dosage form has a weight of about 12 grams.

Embodiment 120. The composition of any one of embodiments 100-119, wherein the composition is in a powder form.

Embodiment 121. The composition of any one of embodiments 100-120, further comprising a preservative.

Embodiment 122. The composition of any one of embodiments 100-121, further comprising a pharmaceutically acceptable excipient.

Embodiment 123. The composition of any one of embodiments 100-122, further comprising a flavoring agent.

Embodiment 124. The composition of any one of embodiments 100-123, wherein the composition further comprises taurine, a hydrate thereof, or a salt thereof from about 0.05% to about 2% (w/w).

Embodiment 125. The composition of any one of embodiments 100-124, wherein the composition further comprises from about 1% to about 4% (w/w) of a $Mg^{2+}$ source.

Embodiment 126. The composition of embodiment 125, wherein the $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, or magnesium malate, magnesium orotate, or a hydrate thereof.

Embodiment 127. The composition of embodiment 125, wherein the $Mg^{2+}$ source is magnesium citrate.

Embodiment 128. The composition of embodiment 125, wherein the $Mg^{2+}$ source is magnesium aspartate, and the aspartic acid, the hydrate thereof, or the salt thereof is aspartic acid free acid.

Embodiment 129. The composition of any one of embodiments 100-128, wherein the composition further comprises from about 2% to about 5% of a $K^+$ source.

Embodiment 130. The composition of embodiment 129, wherein the $K^+$ source comprises potassium citrate, potassium phosphate, potassium chloride, potassium sulfate, potassium gluconate, potassium bicarbonate, potassium aspartate, potassium acetate, and potassium orotate.

Embodiment 131. The composition of embodiment 129, wherein the $K^+$ source is potassium chloride.

Embodiment 132. The composition of embodiment 129, wherein the $K^+$ source is potassium aspartate, and the aspartic acid, the hydrate thereof, or the hydrate thereof is aspartic acid free base.

Embodiment 133. The composition of any one of embodiments 100-132, wherein the histidine, the hydrate thereof, or the salt thereof is histidine hydrochloride.

Embodiment 134. The composition of any one of embodiments 100-132, wherein the lysine, the hydrate thereof, or the salt thereof is lysine hydrochloride.

Embodiment 135. The composition of any one of embodiments 100-134, wherein the lysine, the hydrate thereof, or the salt thereof is lysine monohydrate.

Embodiment 136. The composition of any one of embodiments 100-111 or 116-135, wherein the cysteine, the hydrate thereof, or the salt thereof is cysteine hydrochloride.

Embodiment 137. The composition of any one of embodiments 100- or 116-136, wherein the asparagine, the hydrate thereof, or the salt thereof is asparagine hydrate.

Embodiment 138. The composition of any one of embodiments 100-104 or 107-137, wherein the glutamic acid, the hydrate thereof, or the salt thereof is arginine glutamate, and the arginine is arginine free base.

What is claimed is:

1. A composition for treating a patient with cancer comprising in unit dosage form:
    a) a non-essential amino acid comprising glutamate or a salt thereof in an amount from about 4% to about 8% (w/w), wherein the non-essential amino acid or the salt thereof is not part of a polypeptide;
    b) a first essential amino acid comprising histidine or a salt thereof in an amount from about 3% to about 7% (w/w) and a second essential amino acid comprising isoleucine or a salt thereof in an amount from about 2% to about 6% (w/w), wherein the first essential amino acid or the salt thereof and the second essential amino acid or the salt thereof are not part of a polypeptide; and
    c) a pharmaceutically acceptable excipient,
    wherein the composition is devoid of two non-essential amino acids that are serine and salts thereof and glycine and salts thereof.

2. The composition of claim 1, further comprising a third essential amino acid or a salt thereof, wherein the third essential amino acid or the salt thereof is present in the composition in a different amount from the first essential amino acid or the salt thereof and the second essential amino acid or the salt thereof.

3. The composition of claim 1, wherein the composition is further devoid of proline and salts thereof.

4. The composition of claim 1, wherein the composition is further devoid of cysteine and salts thereof.

5. The composition of claim 1, wherein the unit dosage form has a weight of about 12 grams.

6. The composition of claim 1, wherein the composition is in a powder form.

7. The composition of claim 1, wherein the composition further comprises from about 2% to about 5% (w/w) of a $K^+$ source.

8. The composition of claim 7, wherein the $K^+$ source comprises potassium citrate, potassium phosphate, potassium chloride, potassium sulfate, potassium gluconate, potassium bicarbonate, potassium aspartate, potassium acetate, potassium orotate, potassium bromate, potassium benzoate, potassium hydroxide, potassium iodide, or a hydrate thereof.

9. The composition of claim 1, wherein the composition further comprises from about 1% to about 4% (w/w) of a $Mg^{2+}$ source.

10. The composition of claim 9, wherein the $Mg^{2+}$ source comprises magnesium citrate, magnesium fumarate, magnesium acetate, magnesium aspartate, magnesium threonate, magnesium glycinate, magnesium chloride, magnesium sulfate, magnesium oxide, magnesium malate, magnesium orotate, magnesium gluconate, magnesium stearate, magnesium carbonate, or a hydrate thereof.

11. The composition of claim 1, wherein the composition further comprises taurine, a hydrate thereof, or a salt thereof from about 0.05% to about 2% (w/w).

12. The composition of claim 1, wherein the composition is further devoid of glutamine and salts thereof.

13. The composition of claim 1, wherein the composition is further devoid of glutamine and salts thereof, and cysteine and salts thereof.

14. The composition of claim 1, wherein the composition further comprises a flavorant.

15. The composition of claim 1, wherein the composition further comprises a sweetener.

* * * * *